(12) United States Patent
da Costa e Silva et al.

(10) Patent No.: US 7,608,757 B2
(45) Date of Patent: Oct. 27, 2009

(54) SIGNAL TRANSDUCTION STRESS-RELATED PROTEINS AND METHODS OF USE IN PLANTS

(75) Inventors: Oswaldo da Costa e Silva, Apex, NC (US); Hans J. Bohnert, Tucson, AZ (US); Nocha van Thielen, Cary, NC (US); Ruoying Chen, Apex, NC (US); Manabu Ishitani, Cary, NC (US)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 11/566,246

(22) Filed: Dec. 4, 2006

(65) Prior Publication Data

US 2007/0157344 A1 Jul. 5, 2007

Related U.S. Application Data

(60) Continuation of application No. 10/770,225, filed on Feb. 2, 2004, now Pat. No. 7,166,767, which is a division of application No. 09/828,447, filed on Apr. 6, 2001, now Pat. No. 6,720,477.

(60) Provisional application No. 60/196,001, filed on Apr. 7, 2000.

(51) Int. Cl.
*C12N 15/82* (2006.01)
*C12N 15/29* (2006.01)
*A01H 5/00* (2006.01)
*A01H 5/10* (2006.01)

(52) U.S. Cl. .................. 800/289; 435/419; 435/468; 800/298; 800/320.1; 800/320.2; 800/312; 800/314; 800/306; 536/23.6

(58) Field of Classification Search .................. None
See application file for complete search history.

(56) References Cited

U.S. PATENT DOCUMENTS

2006/0236419 A1 10/2006 La Rosa et al.

OTHER PUBLICATIONS

Seelbach G. et al. Over-expression of plant 14-3-3 proteins in tobacco: enhancement of the plasmalemma K+ conductance of mesophyll cells. FEBS Lett. Aug. 18, 1997;413(2):294-8.*
Ishida Y. et al. High efficiency transformation of maize (*Zea mays* L.) mediated by Agrobacterium tumefaciens. Nat Biotechnol. Jun. 1996;14(6):745-50.*
Muller A.J. et al. High meiotic stability of a foreign gene introduced into tobacco by Agrobacterium-mediated transformation. Mol Gen Genet. Apr. 1987;207(1):171-5.*
MacRobbie E.A.C. Signal transduction and ion channels in guard cells. Philos Trans R Soc Lond B Biol Sci. Sep. 29, 1998;353(1374):1475-88. Review.*
Pilon-Smits E. et al. Improved Performance of Transgenic Fructan-Accumulating Tobacco under Drought Stress. Plant Physiol. Jan. 1995;107(1):125-130.*

* cited by examiner

*Primary Examiner*—Cynthia Collins
(74) *Attorney, Agent, or Firm*—Patricia A. McDaniels

(57) ABSTRACT

A transgenic plant transformed by a Signal Transduction Stress-Related Protein (STSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated STSRPs, and isolated nucleic acid coding STSRPs, and vectors and host cells containing the latter.

18 Claims, 9 Drawing Sheets

LB OCS3 NPTII  AtAct2-i     Super promoter    "Gene of Interest"   NOSpA   RB

PpPLC-1

WT

PpPLC-2

WT

Pp14-3-3P-1

WT

PpPLC-2

WT

SEQUENCE LISTING

<160> NUMBER OF SEQ ID NOS: 41

<210> SEQ ID NO 1
<211> LENGTH: 760
<212> TYPE: DNA
<213> ORGANISM: Physcomitrella patens

<400> SEQUENCE: 1

```
gcacgagtcc aagaaggggg atttggcgca ggatctattg ggggatgtgt tctcgactta      60
cagcgagaat gggaagctgg acgccgaggg gttgctgaag ttcttgcaga cagagcaagg     120
ggatagcaag tcctctctag atgacgccaa gcacctagtg gagttgattc ggaatgagag     180
acataagtcg aaattccctg gttcatcgt cagctcggac ctgtcgaagg gtgattttaa      240
aaactatgta ctgagcccgg atttgaatgg ggttcttgaa agcactgtgc atcaagacat     300
gacgcagccg ttatcgcact acttcatatt cactggtcac aactcgtact tgacgggtaa     360
ccagcttagc agcgacagta gcgacgttcc cattgctgct gcactgcaac gtggcgtgcg     420
ggtggtgaa ctggatttgt ggcctgacga taaaggcggc atcaaggtca ctcacggaa      480
cacactcacc agtccagttg ctttcgagaa gtgcataaaa gccatcaagg ccaacgcgtt     540
cgtctcctcg aaatatcctg tagttatcac tcttgaggat catctttcaa gtcctttaca     600
ggcccttgct gcagagactt tgacgaacat tttgggagag gacttgtact atccaccctc     660
atccgatggg tttaaagaac tgccttctcc ggaatcattg aaagggaaaa ttctaatatc     720
taccaaaccg ccgaaagaat accttgaagc cgctgtcgca                            760
```

<210> SEQ ID NO 2
<211> LENGTH: 706
<212> TYPE: DNA
<213> ORGANISM: Physcomitrella patens

```
<220> FEATURE:
<221> NAME/KEY: modified_base
<222> LOCATION: (687)
<223> OTHER INFORMATION: a, t, c, g, other or unknown

<400> SEQUENCE: 2
cggcaccagg cggcatgaag gtcacacacg gaaacacact taccaatccg gtgtcgttcc      60
aaaagtgtgt cacagccatc aagaataacg ccttcttcac ctcggagtac ccagtttgcg     120
ttactattga ggatcatctt acaagcgaat tacagggcca tgctgcagag attttagagc     180
aaattctcgg agacgccctg tattatccac ccacaactga tgcattagtg gagtttcctt     240
caccggagtc actgaagagg aagatcataa tctccaccaa accgccgaag gagtatctcg     300
aagcatgttc cacgcagaaa ttggccatgg agaacaggaa tctggtggag gagctcgaga     360
aggaagacaa attggagcag accacattcg ctcccctgga gagaaccac  atcctgggag     420
aaaatacacc atcgctgcgt aaggaagtcg aggttttaag ccaaaaggaa atgtcaacac     480
caagctgagc ttaactctag aaagtccctc ctggacctcg gggaagcaac catccacaag     540
gtatagcaaa gagcaacgat ggcaatgaca accctaaaac atttcaagta tgcccggttc     600
atcaacatcc ggctagcaaa cacgcaacgg ggacatcgtg gcgctcgcac tgccagtcga     660
tggatcagaa cggatcagcg gcgatcnatg aaaaggggaa tgccga                    706

<210> SEQ ID NO 3
<211> LENGTH: 1320
<212> TYPE: DNA
<213> ORGANISM: Physcomitrella patens

<400> SEQUENCE: 3 tttttttta attgtaaacc gcacagcccg gacacaaaac catcccactg cacgagtcag       60
atataaccgt acatgatgtt tataatgcat tgttcatttt aatattaaaa tcttagcatt     120
cctcatccta gccaacgaag gaaagaaaaa agagaaaaga aaaggacaaa agaggaaatc     180
tatgaacagc cagtctctac gcagaacaaa ataggcaaga catgtcatac aaccgccagc     240
acggaactac actacgtctc gccccggcct accaccaatc aattgaggct ctttccgaat     300
ccacccccatc agaaaagact tgattgtcgt gatcactccg cttcctccgg tctcatgtca     360
tctccctttc cctggtcgtc gcctacatcg tcctggagat ctgacgtcca taaagtcaga     420
ttatctctaa gtagttgcat gatcaatgtg ctgtccttgt acgactcctc actcaatgtg     480
tccaattcgg caattgcctc gtcgaatgct tgcttcgcca aatggcatgc ccgctcaggg     540
gagttcaaaa tctcataata aagacagag aagttcaagg ccagtcccag ccgaatcgga     600
tgagttggcg ccaagtctgt cacttgctgt attagatgca gcctggtagg ccttcaaaga     660
ttggtcagca gcttctttc  tctcagcccc agttttgaac tccgccaggt accgatagta     720
atctcccttc atttttatagt agaacacagt ggactctccc gtgctggacg aaggaatcaa     780
atgtccgtcg atgatagaca ggatatcatt gcagatcttc gacagctcct cctccacctt     840
gtgtctgtag tccttgatgc gtttaacatt ctgttcgtta cctttgctct cctccttctg     900
ttcgatggat gacatgatcc gccatgacgc cctccgggct ccgatgacat tcttataacc     960
cacggacaag agatttcgct cctctactgt cagctccaca tcaagcttgg caaccttctt    1020
catcgattcc accatctcat cgtaacgctc cgcctgctcg gcgagcttgg ccatgtacac    1080
atagctctcg cgctccttct ccgtactcat cttggcctag cacactcgtc cacgacagtc    1140
cgaaatagca gtatcgcgca ccgtccccg  agcacaaacc aagcgcagaa cggcaacaca    1200
```

```
ctatgcaatg taaaggaaac gcagacacaa gaggagacgg aaaaaacaat agaggcagga   1260
agagagtggg agagaagaga cggggagcg gggcgatgga ggagcacggt gagctggtgc    1320
```

```
<210> SEQ ID NO 4
<211> LENGTH: 482
<212> TYPE: DNA
<213> ORGANISM: Physcomitrella patens
<220> FEATURE:
<221> NAME/KEY: modified_base
<222> LOCATION: (43)
<223> OTHER INFORMATION: a, t, c, g, other or unknown
<220> FEATURE:
<221> NAME/KEY: modified_base
<222> LOCATION: (227)
<223> OTHER INFORMATION: a, t, c, g, other or unknown
<220> FEATURE:
<221> NAME/KEY: modified_base
<222> LOCATION: (266)
<223> OTHER INFORMATION: a, t, c, g, other or unknown

<400> SEQUENCE: 4
gcacgagcac tgttacatcg tcgtagatct ggtcagatac canaaccggc gagaagcatg     60
caacacaaga aaacctggag atgtaatggt tatgccgata gggtttcatt taaaacaatc    120
tacataaccc agtgctaatt gttctgggaa gtcgagcaca tatccgtacc agcctcaact    180
tagtcgcctg gacatgagtt tctattctaa gttctagtgg tcatcancat cttcgacctt    240
ggaatccttt ccttcttcac caatgncgtc ctgcatatct gaagtccata aggtaaggtt    300
atcccggagc agctgcataa tgagagtact gtctttgtag gattcctctc ctaaggtatc    360
taactcagag atagcttcat caaaagcctg cttggcaaga tggcatgctc ggtctggaga    420
aaccaaaatt tcgtagtaaa agacagaaaa attcaaagcc aatcccaatc tgatctcgtg    480
cc                                                                   482
```

```
<210> SEQ ID NO 5
<211> LENGTH: 811
<212> TYPE: DNA
<213> ORGANISM: Physcomitrella patens
<220> FEATURE:
<221> NAME/KEY: modified_base
<222> LOCATION: (722)
<223> OTHER INFORMATION: a, t, c, g, other or unknown
<220> FEATURE:
<221> NAME/KEY: modified_base
<222> LOCATION: (746)
<223> OTHER INFORMATION: a, t, c, g, other or unknown
<220> FEATURE:
<221> NAME/KEY: modified_base
<222> LOCATION: (761)
<223> OTHER INFORMATION: a, t, c, g, other or unknown
<220> FEATURE:
<221> NAME/KEY: modified_base
<222> LOCATION: (772)
<223> OTHER INFORMATION: a, t, c, g, other or unknown
<220> FEATURE:
<221> NAME/KEY: modified_base
<222> LOCATION: (785)
<223> OTHER INFORMATION: a, t, c, g, other or unknown
<220> FEATURE:
<221> NAME/KEY: modified_base
<222> LOCATION: (804)..(805)
<223> OTHER INFORMATION: a, t, c, g, other or unknown

<400> SEQUENCE: 5
gcaccaggtt ttagtaacag atgggaaata ctgcaagagc gtttggttgt tgaaagggcc     60
tacagttgta aactaggcga tcacaagtgc attgcttcat tgagctttcg catggactca    120
atccagctat tgatctcaat ctttgttttt tctaaaacat tttttcacac agatgagccg    180
```

```
gtagtagtgt cagtactaga cggctcagca attaaggctt tgctagaaga tgaagatgat      240
tttgcgatgg ttgccgagga tctgtttgag aagttagaca ctgatgagag tggcaagctg      300
agcagcaaag agcttcgacc tgccattatg cagctgggcg ttgagcaggg tgtccctcct      360
gccgcagcta ctactgaagc ggaggaattg gttaccaagt tgatcaacaa gtacggccag      420
ggaaccgagg agcttggaca agctcaattt gctgcattat tgcaagatgt ccttcaggat      480
atggccgagt ctcttgcaga gaaacctatc acaattgtac gagatgtgaa aatgctcaac      540
ggctctcatt tgcgaaagat gcttggctga tgagaaggca ttcaaaggaa atggcagata      600
acatgtttta attgacctca gatgtcaaca aaagatcaac gcttgagcaa gtgaaatcag      660
accattattt gaacaacaaa ctgagcgtgg gggtctacct cccgtggtga ttcggcacaa      720
anaatattga cgagtttcag gcgtgntcca caaacatggg nagtgaagcc gntttggatc      780
ggcanacccc gcggtttggg aacnnggggt c                                    811

<210> SEQ ID NO 6
<211> LENGTH: 2276
<212> TYPE: DNA
<213> ORGANISM: Physcomitrella patens

<400> SEQUENCE: 6
atcccgggaa tcgtcgggtg acattcctgt tcctactgct gtttggccca ttcgtccact       60
cggcccatct ccactgactt ccccaattga gatcagatgg tcttgtaagg cagagagcga      120
gcgagagaga gagagagaga gagagagaga ttgggagttg aggcgaaggg gaggtgtcgg      180 aggggatttta ttgtgccgta gctgggtttg caaaaatgtg ttctattccg ttcggtcgga      240
agaagtccaa gaaggggat ttggcgcagg atctgttggg ggatgtgttc tcgacttaca      300
gcgagaatgg gaagctggac gccgagggt tgctgaagtt cttgcagaca gagcaagggg      360
atagcaagtc ctctctagat gacgccaagc atttagtgga gttgattcgg aatgagagac      420
ataagtcgaa attccctggg ttcatcgtca gctcggacct gtcgaagggt gattttaaaa      480
actatgtact gagcccggat ttgaatgggg ttccttgaaag cactgtgcat caagacatga      540
cgcagccgtt atcgcactac ttcatattca ctggtcacaa ctcgtacttg acgggtaacc      600
agcttagcag cgacagtagc gacgttccca ttgctgctgc actgcaacgt ggcgtgcggg      660
tggtggaact ggatttgtgg cctgacgata aaggcggcat caaggtcact cacgggaaca      720
cactcaccag tccagttgct ttcgagaagt gcataaaagc catcaaggcc aacgcgttcg      780
tctcctcgaa atatcctgta gttatcactc ttgaggatca tctttcaagt cctttacagg      840
cccttgctgc agagactttg acgaacattt tgggagagga cttgtactat ccaccctcat      900
ccgatgggtt taaagaactg ccttctccgg aatcattgaa agggaaaatt ctaatatcta      960
ccaaaccgcc gaaagaatac cttgaagccg ctgtcgcaca gaagtcggcg ttgaaagatg     1020
aaaagatttt gaatgagttc aagaaggcag ataagttgca ggagcagtca actgctcctg     1080
ttaaaagccc cgttgagaaa aagattgcag ttccaccatc agagaagaca aaatccattt     1140
ccgaagagaa ggacttgagt gaaaaagttg gaaatttacg tgttgattca gagggtgaat     1200
cagctgatcc tgcccctgca agttccccg acggtaagaa agcaacattg acagcggata     1260
gtgaaagtga cgatgacgac aataagaaga atcctgagta tgctcggctt atcactatcc     1320
accaatcgaa gccttcgaaa ggaactaccg tggaagacag actgaaagtt gaagggacag     1380
tggtacggat tagtctttca gagactaagc tggagaaggt cactgaagag tttcctgaac     1440
```

-continued

| | |
|---|---|
| ttgtggtcaa gttcacgcag aggaacattc tacgtgtgta tcctgctggt aaccgagtaa | 1500 |
| actcgtccaa ctatgatcct actgcggctt ggattcacgg agctcaaatg gtggctcaaa | 1560 |
| atatgcaagg ttatggcaaa gagctctggc aagcccacgg caagttcagg ggaaatggtg | 1620 |
| gctgtggata catccttaag ccaaagtatc tattggaaga tttgcccaat ggtaaacctt | 1680 |
| ttaacccttc aggacaaagc gttccccaaa taccatttcg accttttctc gcctccagat | 1740 |
| ttcttcacta ggctgcttgt gactggagtg cctgccgatg tggcaaagtg gaaaacttcc | 1800 |
| gttatagatg acgtttggga accccactgg aacgaggatc acgagtttta ccttaaatgc | 1860 |
| cctgaacttg cactgctccg aattgaagtt agagatcacg acgaggaaag tcaagatgag | 1920 |
| ttcgaagggc aggcgtgcct tccaatgcat gaaattaaag acggctatcg atgcgtgcag | 1980 |
| atgtatgaca aaaagggcag tgtgttgaag ggcgtgaaaa tgttgttcca ttttcaaaaa | 2040 |
| cgttcgtttt ctccggtcca gtaattcatc gttttcaaaa acatttctgt ctcaatcctg | 2100 |
| caacgagtaa ttttagagaa ggaaggctaa cgcactcgag atgtctgaaa ggtgaagagt | 2160 |
| tggagggaag aagggtagct cgctgtatca ccgagctcta gtgaacttca ggtgtcattc | 2220 |
| tttgagggca gctcatcttt ctcatgcatg tggaacgctg aggtgttggt taacgc | 2276 |

<210> SEQ ID NO 7
<211> LENGTH: 2139
<212> TYPE: DNA
<213> ORGANISM: Physcomitrella patens

<400> SEQUENCE: 7

| | |
|---|---|
| atcccgggct tcgggagttt aagaggatgt cacggcgtgg gaagacgagg cggtgatgca | 60 |
| ggtttgggtg gagcttaagg ttgacggagt gtaaggggatc ggctcgtcac tgggtttgca | 120 |
| aaatgtgttc catagcatgt tgtcgaagtg gaaccccgaa aggggatccg gagcaagacc | 180 |
| tggtggggga ggtgttcaca atatacagcg agaatgagag gatgagtgcg gaggggttgc | 240 |
| tgaaattctt gcatacagag caaggggatg tcgacttcac ccttgatgac gccaagcaga | 300 |
| tcatggagcg cattcgcaag gactggaaga atccttcgg actcgcctct atcaactcag | 360 |
| acttgtcgaa ggaggctttt cggaagtact tgatgaatcc cgacttgaat ggcgtcttac | 420 |
| acaacgttgt tcaccaagac atgacgcagc cgatgtcgca ctatttcata ttcacgggcc | 480 |
| ataactcgta cctgaccggc aaccagctga gcagcgacag cagcgacaca cccatcgctg | 540 |
| cggcactgcg gcgcggcgtg cgggttgtgg aattggactt gtggcctgat gacaaaggcg | 600 |
| gcatgaaggt cacacacgga aacacactta ccaatccggt gtcgttccaa aagtgtgtca | 660 |
| cagccatcaa gaataacgcc ttcttcaccct cggagtaccc agtttgcgtt actattgagg | 720 |
| atcatcttac aagcgaatta cagggccatg ctgcagagat tttagagcaa attctcggag | 780 |
| acgccctgta ttatccaccc acaactgatg cattagtgga gtttccttca ccggagtcac | 840 |
| tgaagaggaa gatcataatc tccaccaaac cgccgaagga gtatctcgaa gcatgttcca | 900 |
| cgcagaaatt ggccatggag aacaggaatc tggtggagga gcttgagaag gaagacaaat | 960 |
| tggagcagac cacattcgct cccccttgaag agaaccacat cctgggagaa atacaccat | 1020 |
| cgctgcgtaa ggaagtcgag gttttaagcc aaaaggaaat gtcaacacca gctgagctta | 1080 |
| actctagaag tccctctgac ctcggggaag caacatccac aaggtatagc aagagcaacg | 1140 |
| atggcaatga caacccctaaa catttcaagt atgcccggct catcacaatc cggctagcaa | 1200 |
| agcacgcaaa ggggacatcg atggagcatc gactgcaagt cgatgaatca gtgaaacgga | 1260 |
| tcagtctgtc ggaatcgaag ctggaaaaag tggtggaaaa gtggcccgaa gctctggtca | 1320 |

```
aattcacgca gaagaacatt ttacgtgtgt atcctgctgc taatcgtgta aactcctcca    1380
acttctgccc tactctggct tggaactacg gagctcaaat ggtggctcaa acatgcagg     1440 gctatggtaa agagctttgg caggcatttg gcaagttcaa gggaaatggg ggatgtgggt   1500
atgttttgaa gccacagtat ctgttggaaa acttgccttc tggtgtgcct ttcaacccca   1560
catcacccag aaacacaacc ctaattctca agattaaagt tatgactacc ttgggatggg   1620
acaaggcctt ttccaaacgc catttttgacc tattctcacc tccagatttc ttcactaggg  1680
tgattgtggt gggagtgcct gctgacgagg ccaagtggaa gacatctgtg gtggacaatt   1740
catgggcacc ccattggaat gaggaccatg agtttgccct aaaatgccct gagctcgcac   1800
tacttcgcat cgaggtccga gaccatgatg atgatagcaa agatgagttt gaagggcaga   1860
catgccttcc catccatgaa gtccgggatg ggtatcggtg catgcaaatg tacgacaaga   1920
agggcaatgt actgaaaggc gtgctgatgt tgtttcattt tcaaaagtgc aaatgcacct   1980
ttcaagacac agctcctata tcctcttaaa ctcaacccgc ccacacatgg ccccattatc   2040
aattactaat gctgcttttt atgttgccat tgtcatataa ttgttggttt gtgggggga    2100 agactgacca gtttagtgtg tgcacccaag gttaacgcc                           2139

<210> SEQ ID NO 8
<211> LENGTH: 916
<212> TYPE: DNA
<213> ORGANISM: Physcomitrella patens

<400> SEQUENCE: 8
atcccgggcg gactgtcgtg gacgatgtgc taggccaaga tgagtacgga gaaggagcgc    60
gagagctatg tgtacatggc caagctcgcc gagcaggcgg agcgttacga tgagatggtg   120
gaatcgatga agaaggttgc caagcttgat gtggagctga cagtagagga gcgaaatctc   180
ttgtccgtgg gttataagaa tgtcatcgga gcccggaggg cgtcatggcg gatcatgtca   240
tccatcgaac agaaggagga gagcaaaggt aacgaacaga atgttaaacg catcaaggac   300
tacagacaca aggtggagga ggagctgtcg aagatctgca atgatatcct gtctatcatc   360
gacggacacc tgattccgtc gtccagcacg ggagagtcca ctgtgttcta ctataaaatg   420
aagggagatt actatcggta cctggcggag ttcaagaccg ggaatgagag gaaagaggcc   480
gctgaccaat ctttgaaggc ataccaggct gcatccagca ctgcagtgac ggacctggca   540
ccgacgcatc ctatccgact gggattagct ttgaacttct cggtcttttat ttatgaaatt   600 ttgaactctc ctgagagggc atgccatttg gcgaaacaag catttgacga ggcgattgct   660
gagttggata cgttaagtga ggagtcgtac aaggacagca cattgatcat gcagctactt   720
agagataatc tgaccctgtg gacatctgac cttcaggacg agggaggtga cgaccaggga   780
aagggagatg atatgaggcc cgaggaggct gagtgatgac gattaggtct tttatgtgga   840
gacgaatttg caaatcactt cactcaattg gtggtgggcc ggggcaagaa gatgtgcagt   900
tgcgtgccga gctcgc                                                   916

<210> SEQ ID NO 9
<211> LENGTH: 840
<212> TYPE: DNA
<213> ORGANISM: Physcomitrella patens

<400> SEQUENCE: 9
gcgttaactt cacaatgacg gagctacgag aggaaaatgt gtacatggct aagctcgccg    60
```

-continued

| | |
|---|---:|
| agcaggcgga gcggtacgat gagatggtgg aagccatgga gaatgtggta aaggcggtgg | 120 |
| agaacgagga gctgaccgtg gaggagcgga acctgttgtc ggtggcgttt aagaacgtga | 180 |
| ttggtgcgag gagggcgtcg tggcggatca tctcttccat cgagcagaag gaagaggcca | 240 |
| aggggtctga ggagcacgtc gctgctatta aggagtaccg atccaaagta gaggctgagt | 300 |
| tgagcaccat ctgtgacact atattgaagc ttttggactc gcacctgatc ccgtcctcca | 360 |
| cctcggggga gtcgaaggtt ttttacttga aaatgaaggg agactatcac aggtacctgg | 420 |
| ctgagttcaa agccggcgct gagagaaaag aggcagctga ggctacattg cacgcgtaca | 480 |
| agcatgcaca agacatttca acgacagagt tggcgtccac acatcctatc agattgggat | 540 |
| tggctttgaa ttttctgtc ttttactacg aaattttggt ttctccagac cgagcatgcc | 600 |
| atcttgccaa gcaggctttt gatgaagcta tctctgagtt agataccta ggagaggaat | 660 |
| cctacaaaga cagtactctc attatgcagc tgctccggga taaccttacc ttatggactt | 720 |
| cagatatgca ggacgacatt ggtgaagaag gaaaggattc caaggtcgaa gatgctgatg | 780 |
| accactagaa cttagaatag aaactcatgt ccaggcgact aagttgaggc tggagctcgc | 840 |

<210> SEQ ID NO 10
<211> LENGTH: 1800
<212> TYPE: DNA
<213> ORGANISM: Physcomitrella patens

<400> SEQUENCE: 10

| | |
|---|---:|
| atcccgggtc agctcgtgga agtgttgcag cagcgcggac gggcaggatc ggacattttg | 60 |
| agattttga cagggctatc agaggtgttc agaagggacg acaaagacca gcatgtcaac | 120 |
| agagggagga ctgcatgttc ttgatggatc tcagatcaga aatgcattac ccgatcttca | 180 |
| atcgaggaac agtttttcta agaatgatga agggtcgaaa gggtatctga caccatctga | 240 |
| gatgcggcag gctgcggaag cagaagcagc cgctcttctc ttaggtgtcc aacttttcctc | 300 |
| aaagattttt gaaaatgctg catcaaaact tccaactgaa gattctgcag agatcacgga | 360 |
| ggacgtgttt tccagtactc tgcagagtta tctaacagca attgctgatg ctttagaaga | 420 |
| tgagccggta gtagtgtcag tactagacgg ctcagcaatt aaggctttgc tagaagatga | 480 |
| agatgatttt gcgatggttg ccgaggatct gtttgagaag ttagacactg atgagagtgg | 540 |
| caagctgagc agcaaagagc ttcgacctgc cattatgcag ctgggcgttg agcagggtgt | 600 |
| ccctcctgcc gcagctacta ctgaagcgga ggaattggtt accaagttga tcaacaagta | 660 |
| cggccaggga accgaggagc ttggacaagc tcaatttgct gcattattgc aagatgtcct | 720 |
| tcaggatatg gccgagtctc ttgcagagaa acctatcaca attgtacgag atgtgaaaat | 780 |
| gctcaacggc tctcatttgc gaaagatgct ggctgatgag aaggcattca ggaaatggc | 840 |
| agataacatg tttaatgacc tagatgtcaa caaagatcaa cgcttgagca aggctgaaat | 900 |
| cagaccatta tttgaacaac aaactgcagc gtggggtcta cctcccgttg gtgattcgga | 960 |
| cacagaagaa ctatttgacg aggttttcaa ggccgttgac tcagacaaaa gtggggaagt | 1020 |
| tgaaaagcct gagtttgcag ttcttgtcaa gactctcctt gcggattttg cggaaacgtt | 1080 |
| gcggctcaac ccaatactag tggagataga aactgcctct cgttgaagca tcgagtcata | 1140 |
| gttctggggg agcgatgttt tctaaagtcg tagtccattt ttggataaga tgactttgca | 1200 |
| cccagagttc ttgtgaaacg tgacaccagg tatgatgaag gcttgatgat attttagagt | 1260 |
| gacaatttta tgtggctaga ggctcatgag gtcgtgagat cgaagtggaa atgatttgtg | 1320 |
| aaagctactt cgacctgggt agcttttcta agctaggata gttatatgaa aaagataatt | 1380 |

```
aaacttcaag cggatcaata tagctcacag aatccattct tcgtttctgt ttcctgagaa   1440
cccaccaatg tccaagttac aaaactccgt gggagaaaca gacgtgcagt gcatgcataa   1500
ggttggtgtg attgtttgcg tagtgatgtt tctggatgac ttgaatagaa tcaagtgcat   1560
agatagtcaa ttgtctcaca caagatcttc gaacaatcca ccaaccggcg ttgccagtcg   1620
tgcggagggc acggttggtg ggacggacta gcggtgcgac gcgtgtagag aatgcattgg   1680
cggctgcaga ttagacagtt gttcgcatcc gttgtaggat agatcgttag gatactcgac   1740
tcttacctgt gttcgaattc cggcatcgga agcccccgag tgaaaattgg acgagctcgc   1800
```

<210> SEQ ID NO 11
<211> LENGTH: 1054
<212> TYPE: PRT
<213> ORGANISM: Physcomitrella patens

<400> SEQUENCE: 11

```
Met Cys Ser Ile Pro Phe Gly Arg Lys Lys Ser Lys Lys Gly Asp Leu
  1               5                  10                  15

Ala Gln Asp Leu Leu Gly Asp Val Phe Ser Thr Tyr Ser Glu Asn Gly
             20                  25                  30

Lys Leu Asp Ala Glu Gly Leu Leu Lys Phe Leu Gln Thr Glu Gln Gly
         35                  40                  45

Asp Ser Lys Ser Ser Leu Asp Asp Ala Lys His Leu Val Glu Leu Ile
     50                  55                  60

Arg Asn Glu Arg His Lys Ser Lys Phe Pro Gly Phe Ile Val Ser Ser
 65                  70                  75                  80

Asp Leu Ser Lys Gly Asp Phe Lys Asn Tyr Val Leu Ser Pro Asp Leu
                 85                  90                  95

Asn Gly Val Leu Glu Ser Thr Val His Gln Asp Met Thr Gln Pro Leu
            100                 105                 110

Ser His Tyr Phe Ile Phe Thr Gly His Asn Ser Tyr Leu Thr Gly Asn
        115                 120                 125

Gln Leu Ser Ser Asp Ser Ser Asp Val Pro Ile Ala Ala Ala Leu Gln
    130                 135                 140

Arg Gly Val Arg Val Glu Leu Asp Leu Trp Pro Asp Asp Lys Gly
145                 150                 155                 160

Gly Ile Lys Val Thr His Gly Asn Thr Leu Thr Ser Pro Val Ala Phe
                165                 170                 175

Glu Lys Cys Ile Lys Ala Ile Lys Ala Asn Ala Phe Val Ser Ser Lys
            180                 185                 190

Tyr Pro Val Val Ile Thr Leu Glu Asp His Leu Ser Ser Pro Leu Gln
        195                 200                 205

Ala Leu Ala Ala Glu Thr Leu Thr Asn Ile Leu Gly Glu Asp Leu Tyr
    210                 215                 220

Tyr Pro Pro Ser Ser Asp Gly Phe Lys Glu Leu Pro Ser Pro Glu Ser
225                 230                 235                 240

Leu Lys Gly Lys Ile Leu Ile Ser Thr Lys Pro Pro Lys Glu Tyr Leu
                245                 250                 255

Glu Ala Ala Val Ala Gln Lys Ser Ala Leu Lys Asp Glu Lys Ile Leu
            260                 265                 270

Asn Glu Phe Lys Lys Ala Asp Lys Leu Gln Glu Gln Ser Thr Ala Pro
        275                 280                 285

Val Lys Ser Pro Val Glu Lys Ile Ala Val Pro Pro Ser Glu Lys
    290                 295                 300
```

```
Thr Lys Ser Ile Ser Glu Glu Lys Asp Leu Ser Glu Lys Val Gly Asn
305                 310                 315                 320

Leu Arg Val Asp Ser Glu Gly Glu Ser Ala Asp Pro Ala Pro Ala Ser
                325                 330                 335

Ser Pro Asp Gly Lys Lys Ala Thr Leu Thr Ala Asp Ser Glu Ser Asp
            340                 345                 350

Asp Asp Asp Asn Lys Lys Asn Pro Glu Tyr Ala Arg Leu Ile Thr Ile
                355                 360                 365

His Gln Ser Lys Pro Ser Lys Gly Thr Thr Val Glu Asp Arg Leu Lys
        370                 375                 380

Val Glu Gly Thr Val Arg Ile Ser Leu Ser Glu Thr Lys Leu Glu
385                 390                 395                 400

Lys Val Thr Glu Glu Phe Pro Glu Leu Val Val Lys Phe Thr Gln Arg
                405                 410                 415

Asn Ile Leu Arg Met Cys Ser Ile Pro Phe Gly Arg Lys Lys Ser Lys
            420                 425                 430

Lys Gly Asp Leu Ala Gln Asp Leu Leu Gly Asp Val Phe Ser Thr Tyr
        435                 440                 445

Ser Glu Asn Gly Lys Leu Asp Ala Glu Gly Leu Leu Lys Phe Leu Gln
    450                 455                 460

Thr Glu Gln Gly Asp Ser Lys Ser Ser Leu Asp Asp Ala Lys His Leu
465                 470                 475                 480

Val Glu Leu Ile Arg Asn Glu Arg His Lys Ser Lys Phe Pro Gly Phe
                485                 490                 495

Ile Val Ser Ser Asp Leu Ser Lys Gly Asp Phe Lys Asn Tyr Val Leu
            500                 505                 510

Ser Pro Asp Leu Asn Gly Val Leu Glu Ser Thr Val His Gln Asp Met
        515                 520                 525

Thr Gln Pro Leu Ser His Tyr Phe Ile Phe Thr Gly His Asn Ser Tyr
    530                 535                 540

Leu Thr Gly Asn Gln Leu Ser Ser Asp Ser Ser Asp Val Pro Ile Ala
545                 550                 555                 560

Ala Ala Leu Gln Arg Gly Val Arg Val Val Glu Leu Asp Leu Trp Pro
                565                 570                 575

Asp Asp Lys Gly Gly Ile Lys Val Thr His Gly Asn Thr Leu Thr Ser
            580                 585                 590

Pro Val Ala Phe Glu Lys Cys Ile Lys Ala Ile Lys Ala Asn Ala Phe
        595                 600                 605

Val Ser Ser Lys Tyr Pro Val Val Ile Thr Leu Glu Asp His Leu Ser
    610                 615                 620

Ser Pro Leu Gln Ala Leu Ala Ala Glu Thr Leu Thr Asn Ile Leu Gly
625                 630                 635                 640

Glu Asp Leu Tyr Tyr Pro Pro Ser Ser Asp Gly Phe Lys Glu Leu Pro
                645                 650                 655

Ser Pro Glu Ser Leu Lys Gly Lys Ile Leu Ile Ser Thr Lys Pro Pro
            660                 665                 670

Lys Glu Tyr Leu Glu Ala Ala Val Ala Gln Lys Ser Ala Leu Lys Asp
        675                 680                 685

Glu Lys Ile Leu Asn Glu Phe Lys Lys Ala Asp Lys Leu Gln Glu Gln
    690                 695                 700

Ser Thr Ala Pro Val Lys Ser Pro Val Glu Lys Lys Ile Ala Val Pro
705                 710                 715                 720
```

```
Pro Ser Glu Lys Thr Lys Ser Ile Ser Glu Glu Lys Asp Leu Ser Glu
            725                 730                 735

Lys Val Gly Asn Leu Arg Val Asp Ser Glu Gly Ser Ala Asp Pro
        740                 745                 750

Ala Pro Ala Ser Ser Pro Asp Gly Lys Lys Ala Thr Leu Thr Ala Asp
            755                 760                 765

Ser Glu Ser Asp Asp Asp Asn Lys Lys Asn Pro Glu Tyr Ala Arg
770                 775                 780

Leu Ile Thr Ile His Gln Ser Lys Pro Ser Lys Gly Thr Thr Val Glu
785                 790                 795                 800

Asp Arg Leu Lys Val Glu Gly Thr Val Val Arg Ile Ser Leu Ser Glu
                805                 810                 815

Thr Lys Leu Glu Lys Val Thr Glu Glu Phe Pro Glu Leu Val Val Lys
            820                 825                 830

Phe Thr Gln Arg Asn Ile Leu Arg Val Tyr Pro Ala Gly Asn Arg Val
            835                 840                 845

Asn Ser Ser Asn Tyr Asp Pro Thr Ala Ala Trp Ile His Gly Ala Gln
850                 855                 860

Met Val Ala Gln Asn Met Gln Gly Tyr Gly Lys Glu Leu Trp Gln Ala
865                 870                 875                 880

His Gly Lys Phe Arg Gly Asn Gly Gly Cys Gly Tyr Ile Leu Lys Pro
                885                 890                 895

Lys Tyr Leu Leu Glu Asp Leu Pro Asn Gly Lys Pro Phe Asn Pro Ser
            900                 905                 910

Ala Pro Gly Asp Thr Lys Met Ile Leu Lys Val Lys Val Met Thr Thr
            915                 920                 925

Met Gly Trp Asp Lys Ala Phe Pro Lys Tyr His Phe Asp Leu Phe Ser
930                 935                 940

Pro Pro Asp Phe Phe Thr Arg Leu Leu Val Thr Gly Val Pro Ala Asp
945                 950                 955                 960

Val Ala Lys Trp Lys Thr Ser Val Ile Asp Asp Val Trp Glu Pro His
                965                 970                 975

Trp Asn Glu Asp His Glu Phe Tyr Leu Lys Cys Pro Glu Leu Ala Leu
            980                 985                 990

Leu Arg Ile Glu Val Arg Asp His Asp Glu Glu Ser Gln Asp Glu Phe
            995                 1000                1005

Glu Gly Gln Ala Cys Leu Pro Met His Glu Ile Lys Asp Gly Tyr Arg
    1010                1015                1020

Cys Val Gln Met Tyr Asp Lys Lys Gly Ser Val Leu Lys Gly Val Lys
1025                1030                1035                1040

Met Leu Phe His Phe Gln Lys Arg Ser Phe Ser Pro Val Gln
                1045                1050

<210> SEQ ID NO 12
<211> LENGTH: 628
<212> TYPE: PRT
<213> ORGANISM: Physcomitrella patens

<400> SEQUENCE: 12

Met Cys Ser Ile Ala Cys Cys Arg Ser Gly Thr Pro Lys Gly Asp Pro
1               5                   10                  15

Glu Gln Asp Leu Val Gly Glu Val Phe Thr Ile Tyr Ser Glu Asn Glu
            20                  25                  30

Arg Met Ser Ala Glu Gly Leu Leu Lys Phe Leu His Thr Glu Gln Gly
        35                  40                  45
```

```
Asp Val Asp Phe Thr Leu Asp Asp Ala Lys Gln Ile Met Glu Arg Ile
 50                  55                  60

Arg Lys Asp Trp Lys Lys Ser Phe Gly Leu Ala Ser Ile Asn Ser Asp
 65                  70                  75                  80

Leu Ser Lys Glu Ala Phe Arg Lys Tyr Leu Met Asn Pro Asp Leu Asn
                 85                  90                  95

Gly Val Leu His Asn Val Val His Gln Asp Met Thr Gln Pro Met Ser
             100                 105                 110

His Tyr Phe Ile Phe Thr Gly His Asn Ser Tyr Leu Thr Gly Asn Gln
             115                 120                 125

Leu Ser Ser Asp Ser Ser Asp Thr Pro Ile Ala Ala Leu Arg Arg
130                 135                 140

Gly Val Arg Val Val Glu Leu Asp Leu Trp Pro Asp Lys Gly Gly
145                 150                 155                 160

Met Lys Val Thr His Gly Asn Thr Leu Thr Asn Pro Val Ser Phe Gln
                 165                 170                 175

Lys Cys Val Thr Ala Ile Lys Asn Asn Ala Phe Phe Thr Ser Glu Tyr
             180                 185                 190

Pro Val Cys Val Thr Ile Glu Asp His Leu Thr Ser Glu Leu Gln Gly
         195                 200                 205

His Ala Ala Glu Ile Leu Glu Gln Ile Leu Gly Asp Ala Leu Tyr Tyr
210                 215                 220

Pro Pro Thr Thr Asp Ala Leu Val Glu Phe Pro Ser Pro Glu Ser Leu
225                 230                 235                 240

Lys Arg Lys Ile Ile Ile Ser Thr Lys Pro Pro Lys Glu Tyr Leu Glu
                 245                 250                 255

Ala Cys Ser Thr Gln Lys Leu Ala Met Glu Asn Arg Asn Leu Val Glu
             260                 265                 270

Glu Leu Glu Lys Glu Asp Lys Leu Glu Gln Thr Thr Phe Ala Pro Leu
         275                 280                 285

Glu Glu Asn His Ile Leu Gly Glu Asn Thr Pro Ser Leu Arg Lys Glu
290                 295                 300

Val Glu Val Leu Ser Gln Lys Glu Met Ser Thr Pro Ala Glu Leu Asn
305                 310                 315                 320

Ser Arg Ser Pro Ser Asp Leu Gly Glu Ala Thr Ser Thr Arg Tyr Ser
                 325                 330                 335

Lys Ser Asn Asp Gly Asn Asp Asn Pro Lys His Phe Lys Tyr Ala Arg
             340                 345                 350

Leu Ile Thr Ile Arg Leu Ala Lys His Ala Lys Gly Thr Ser Met Glu
         355                 360                 365

His Arg Leu Gln Val Asp Glu Ser Val Lys Arg Ile Ser Leu Ser Glu
370                 375                 380

Ser Lys Leu Glu Lys Val Val Glu Lys Trp Pro Glu Ala Leu Val Lys
385                 390                 395                 400

Phe Thr Gln Lys Asn Ile Leu Arg Val Tyr Pro Ala Ala Asn Arg Val
                 405                 410                 415

Asn Ser Ser Asn Phe Cys Pro Thr Leu Ala Trp Asn Tyr Gly Ala Gln
             420                 425                 430

Met Val Ala Gln Asn Met Gln Gly Tyr Gly Lys Glu Leu Trp Gln Ala
         435                 440                 445

Phe Gly Lys Phe Lys Gly Asn Gly Gly Cys Gly Tyr Val Leu Lys Pro
450                 455                 460
```

```
Gln Tyr Leu Leu Glu Asn Leu Pro Ser Gly Val Pro Phe Asn Pro Thr
465                 470                 475                 480

Ser Pro Arg Asn Thr Thr Leu Ile Leu Lys Ile Lys Val Met Thr Thr
            485                 490                 495

Leu Gly Trp Asp Lys Ala Phe Ser Lys Arg His Phe Asp Leu Phe Ser
        500                 505                 510

Pro Pro Asp Phe Phe Thr Arg Val Ile Val Gly Val Pro Ala Asp
        515                 520                 525

Glu Ala Lys Trp Lys Thr Ser Val Val Asp Asn Ser Trp Ala Pro His
    530                 535                 540

Trp Asn Glu Asp His Glu Phe Ala Leu Lys Cys Pro Glu Leu Ala Leu
545                 550                 555                 560

Leu Arg Ile Glu Val Arg Asp His Asp Asp Ser Lys Asp Glu Phe
                565                 570                 575

Glu Gly Gln Thr Cys Leu Pro Ile His Glu Val Arg Asp Gly Tyr Arg
                580                 585                 590

Cys Met Gln Met Tyr Asp Lys Lys Gly Asn Val Leu Lys Gly Val Leu
                595                 600                 605

Met Leu Phe His Phe Gln Lys Cys Lys Cys Thr Phe Gln Asp Thr Ala
    610                 615                 620

Pro Ile Ser Ser
625

<210> SEQ ID NO 13
<211> LENGTH: 258
<212> TYPE: PRT
<213> ORGANISM: Physcomitrella patens

<400> SEQUENCE: 13

Met Ser Thr Glu Lys Glu Arg Glu Ser Tyr Val Tyr Met Ala Lys Leu
1               5                   10                  15

Ala Glu Gln Ala Glu Arg Tyr Asp Glu Met Val Glu Ser Met Lys Lys
                20                  25                  30

Val Ala Lys Leu Asp Val Glu Leu Thr Val Glu Glu Arg Asn Leu Leu
            35                  40                  45

Ser Val Gly Tyr Lys Asn Val Ile Gly Ala Arg Arg Ala Ser Trp Arg
        50                  55                  60

Ile Met Ser Ser Ile Glu Gln Lys Glu Glu Ser Lys Gly Asn Glu Gln
65                  70                  75                  80

Asn Val Lys Arg Ile Lys Asp Tyr Arg His Lys Val Glu Glu Glu Leu
                85                  90                  95

Ser Lys Ile Cys Asn Asp Ile Leu Ser Ile Ile Asp Gly His Leu Ile
            100                 105                 110

Pro Ser Ser Ser Thr Gly Glu Ser Thr Val Phe Tyr Tyr Lys Met Lys
        115                 120                 125

Gly Asp Tyr Tyr Arg Tyr Leu Ala Glu Phe Lys Thr Gly Asn Glu Arg
    130                 135                 140

Lys Glu Ala Ala Asp Gln Ser Leu Lys Ala Tyr Gln Ala Ala Ser Ser
145                 150                 155                 160

Thr Ala Val Thr Asp Leu Ala Pro Thr His Pro Ile Arg Leu Gly Leu
                165                 170                 175

Ala Leu Asn Phe Ser Val Phe Tyr Tyr Glu Ile Leu Asn Ser Pro Glu
            180                 185                 190

Arg Ala Cys His Leu Ala Lys Gln Ala Phe Asp Glu Ala Ile Ala Glu
        195                 200                 205
```

```
Leu Asp Thr Leu Ser Glu Glu Ser Tyr Lys Asp Ser Thr Leu Ile Met
    210                 215                 220
Gln Leu Leu Arg Asp Asn Leu Thr Leu Trp Thr Ser Asp Leu Gln Asp
225                 230                 235                 240
Glu Gly Gly Asp Asp Gln Gly Lys Gly Asp Met Arg Pro Glu Glu
                245                 250                 255
Ala Glu
```

<210> SEQ ID NO 14
<211> LENGTH: 257
<212> TYPE: PRT
<213> ORGANISM: Physcomitrella patens

<400> SEQUENCE: 14

```
Met Thr Glu Leu Arg Glu Glu Asn Val Tyr Met Ala Lys Leu Ala Glu
 1               5                  10                  15
Gln Ala Glu Arg Tyr Asp Glu Met Val Glu Ala Met Glu Asn Val Val
                20                  25                  30
Lys Ala Val Glu Asn Glu Glu Leu Thr Val Glu Glu Arg Asn Leu Leu
            35                  40                  45
Ser Val Ala Phe Lys Asn Val Ile Gly Ala Arg Arg Ala Ser Trp Arg
        50                  55                  60
Ile Ile Ser Ser Ile Glu Gln Lys Glu Glu Ala Lys Gly Ser Glu Glu
 65                 70                  75                  80
His Val Ala Ile Lys Glu Tyr Arg Ser Lys Val Glu Ala Glu Leu
                85                  90                  95
Ser Thr Ile Cys Asp Thr Ile Leu Lys Leu Leu Asp Ser His Leu Ile
            100                 105                 110
Pro Ser Ser Thr Ser Gly Glu Ser Lys Val Phe Tyr Leu Lys Met Lys
        115                 120                 125
Gly Asp Tyr His Arg Tyr Leu Ala Glu Phe Lys Ala Gly Ala Glu Arg
    130                 135                 140
Lys Glu Ala Ala Glu Ala Thr Leu His Ala Tyr Lys His Ala Gln Asp
145                 150                 155                 160
Ile Ser Thr Thr Glu Leu Ala Ser Thr His Pro Ile Arg Leu Gly Leu
                165                 170                 175
Ala Leu Asn Phe Ser Val Phe Tyr Tyr Glu Ile Leu Val Ser Pro Asp
            180                 185                 190
Arg Ala Cys His Leu Ala Lys Gln Ala Phe Asp Glu Ala Ile Ser Glu
        195                 200                 205
Leu Asp Thr Leu Gly Glu Glu Ser Tyr Lys Asp Ser Thr Leu Ile Met
    210                 215                 220
Gln Leu Leu Arg Asp Asn Leu Thr Leu Trp Thr Ser Asp Met Gln Asp
225                 230                 235                 240
Asp Ile Gly Glu Glu Gly Lys Asp Ser Lys Val Glu Asp Ala Asp Asp
                245                 250                 255
His
```

<210> SEQ ID NO 15
<211> LENGTH: 337
<212> TYPE: PRT
<213> ORGANISM: Physcomitrella patens

<400> SEQUENCE: 15

```
Met Ser Thr Glu Gly Gly Leu His Val Leu Asp Gly Ser Gln Ile Arg
```

```
                1               5              10              15
Asn Ala Leu Pro Asp Leu Gln Ser Arg Asn Ser Phe Ser Lys Asn Asp
                       20                  25                  30

Glu Gly Ser Lys Gly Tyr Leu Thr Pro Ser Glu Met Arg Gln Ala Ala
           35                  40                  45

Glu Ala Glu Ala Ala Leu Leu Gly Val Gln Leu Ser Ser Lys
           50                  55                  60

Ile Phe Glu Asn Ala Ala Ser Lys Leu Pro Thr Glu Asp Ser Ala Glu
 65                  70                  75                  80

Ile Thr Glu Asp Val Phe Ser Ser Thr Leu Gln Ser Tyr Leu Thr Ala
                    85                  90                  95

Ile Ala Asp Ala Leu Glu Asp Glu Pro Val Val Ser Val Leu Asp
                   100                 105                 110

Gly Ser Ala Ile Lys Ala Leu Leu Glu Asp Glu Asp Phe Ala Met
               115                 120                 125

Val Ala Glu Asp Leu Phe Glu Lys Leu Asp Thr Asp Glu Ser Gly Lys
               130                 135                 140

Leu Ser Ser Lys Glu Leu Arg Pro Ala Ile Met Gln Leu Gly Val Glu
145                 150                 155                 160

Gln Gly Val Pro Pro Ala Ala Ala Thr Thr Glu Ala Glu Glu Leu Val
                   165                 170                 175

Thr Lys Leu Ile Asn Lys Tyr Gly Gln Gly Thr Glu Glu Leu Gly Gln
                   180                 185                 190

Ala Gln Phe Ala Ala Leu Leu Gln Asp Val Leu Gln Asp Met Ala Glu
                   195                 200                 205

Ser Leu Ala Glu Lys Pro Ile Thr Ile Val Arg Asp Val Lys Met Leu
                   210                 215                 220

Asn Gly Ser His Leu Arg Lys Met Leu Ala Asp Glu Lys Ala Phe Lys
225                 230                 235                 240

Glu Met Ala Asp Asn Met Phe Asn Asp Leu Asp Val Asn Lys Asp Gln
                   245                 250                 255

Arg Leu Ser Lys Ala Glu Ile Arg Pro Leu Phe Glu Gln Gln Thr Ala
                   260                 265                 270

Ala Trp Gly Leu Pro Pro Val Gly Asp Ser Asp Thr Glu Glu Leu Phe
                   275                 280                 285

Asp Glu Val Phe Lys Ala Val Asp Ser Asp Lys Ser Gly Glu Val Glu
                   290                 295                 300

Lys Pro Glu Phe Ala Val Leu Val Lys Thr Leu Leu Ala Asp Phe Ala
305                 310                 315                 320

Glu Thr Leu Arg Leu Asn Pro Ile Leu Val Glu Ile Glu Thr Ala Ser
                   325                 330                 335

Arg
```

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 16
caggaaacag ctatgacc                                                   18

<210> SEQ ID NO 17
<211> LENGTH: 19

```
<212> TYPE: DNA
<213> ORGANISM: Artificial Sequence
<220> FEATURE:
<223> OTHER INFORMATION: Description of Artificial Sequence: Primer

<400> SEQUENCE: 17
ctaaagggaa caaaagctg                                                    19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 18
tgtaaaacga cggccagt                                                     18

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 19
caggtccgag ctgacgatga acccag                                            26

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 20
atcccgggca atcgtcgggt gacattcctg ttc                                    33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 21
gcgttaacca acacctcagc gttccacatg cat                                    33

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 22
cgagctcctc caccagattc ctgttc                                            26

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 23
```

```
atcccgggct tcgggagttt aagaggatgt cacg                          34

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 24
gcgttaacct tgggtgcaca cactaaactg gtc                           33

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 25
atcccgggcg gactgtcgtg gacgagtgtg ctag                          34

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 26
gcgagctcgg cacgcaactg cacatcttct tgc                           33

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 27
accagcctca acttagtcgc ctggac                                   26

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 28
gcgttaactt cacaatgacg gagctacgag agga                          34

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 29
gcgagctcca gcctcaactt agtcgcctgg aca                           33

<210> SEQ ID NO 30
<211> LENGTH: 26
<212> TYPE: DNA
<213> ORGANISM: Artificial Sequence
```

```
<220> FEATURE:
<223> OTHER INFORMATION: Description of Artificial Sequence: Primer

<400> SEQUENCE: 30
ccctgctcaa cgcccagctg cataat                                          26

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 31
atcccgggtc agctcgtgga agtgttgcag ca                                   32

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 32
gcgagctcgt ccaattttca ctcgggggct tcc                                  33

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 33
gcgctgcaga tttcatttgg agaggacacg                                      30

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 34
cgcggccggc ctcagaagaa ctcgtcaaga aggcg                                35

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 35
gctgacacgc caagcctcgc tagtc                                           25

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 36
ccagcttagc agcgacagta gcgacgt                                         27
```

```
<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 37
cagtctgtct tccacggtag ttcct                                           25

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 38
ggccatggag aacaggaatc tggtgg                                          26

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 39
gctccgtagt tccaagccag agtag                                           25

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 40
gacactgatg agagtggcaa gctgag                                          26

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 41
gactcgatgc ttcaacgaga ggcag                                           25
```

SIGNAL TRANSDUCTION STRESS-RELATED PROTEINS AND METHODS OF USE IN PLANTS

CROSS REFERENCE TO RELATED APPLICATIONS

This application is a continuation application of allowed U.S. Nonprovisional patent application Ser. No. 10/770,225, filed Feb. 2, 2004 now U.S. Pat. No. 7,166,767, which is a divisional application of U.S. Nonprovisional patent application Ser. No. 09/828,447 filed Apr. 6, 2001 and now U.S. Pat. No. 6,720,477, which claims the priority benefit of U.S. Provisional Application Ser. No. 60/196,001 filed Apr. 7, 2000, each of which is hereby incorporated herein in its entirety.

BACKGROUND OF THE INVENTION

1. Field of the Invention

This invention relates generally to nucleic acid sequences encoding proteins that are associated with abiotic stress responses and abiotic stress tolerance in plants. In particular, this invention relates to nucleic acid sequences encoding proteins that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as rice, maize (corn) and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on plant development, growth and yield of most crop plants are profound. Furthermore, most of the crop plants are very susceptible to higher salt concentrations in the soil. Continuous exposure to drought and high salt causes major alterations in the plant metabolism. These great changes in metabolism ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold and salt tolerance in model, drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerance plants using biotechnological methods.

Therefore, what is needed is the identification of the genes and proteins involved in these multi-component processes leading to stress tolerance. Elucidating the function of genes expressed in stress tolerant plants will not only advance our understanding of plant adaptation and tolerance to environmental stresses, but also may provide important information for designing new strategies for crop improvement.

Expression and function of abiotic stress-inducible genes have been well studied at a molecular level. Complex mechanisms seem to be involved in gene expression and signal transduction in response to the stress. These include the sensing mechanisms of abiotic stress, modulation of the stress signals to cellular signals, transduction to the nucleus, second messengers involved in the stress signal transduction, transcriptional control of stress-inducible genes and the function and cooperation of stress-inducible genes.

In animal cells, phosphatidylinositol-specific phospholipase C (PI-PLC) plays a key role in early stages of various signal-transduction pathways. Extracellular stimuli such as hormones and growth factors activate PI-PLCs. PI-PLC hydrolyzes phosphatidylinositol 4,5-biphosphate ($PIP_2$) and generates two second messengers, inositol, 4,5-triphosphate ($IP_3$) and 1,2-diacylglycerol (DG). $IP_3$ induces the release of intracellular $Ca^{2+}$ into the cytoplasm, which in turn causes various responses therein. DG and $PIP_2$ also function as second messengers and control various cellular responses.

In plants, similar systems are thought to function in abiotic stress response. It is clearly demonstrated that phospholipases A, C or D (PLA, PLC or PLD), depending upon their site of cleavage, play a role in the early signal transduction events that promote the cell volume changes associated with osmotic stress and osmoregulation in plants which is important for plant stress tolerance (Wang X. et at., 2000, Biochemical Society Transactions. 28; 813-816; Chapman K D, 1998 Tre. Plant Sci. 3:419-426). For example, in guard cells, abscisic acid (ABA)-induced stomatal closure is mediated by rapid activation of PIP2-PLC. This leads to an increase in $IP_3$ levels, a rise in cytosolic calcium, and the subsequent inhibition of K+ channels. Recently, a gene for phospholipase C, AtPLC was demonstrated to be rapidly induced by drought and salt stresses in *Arabidopsis thaliana* (Hirayama, T. et al., 1995 Proc. Natl. Acad. Sci. 92:3903-3907).

As mentioned above, $Ca^{2+}$ ions play important roles as second messengers in various signal-transduction pathways in plants. Marked increase in intracellular $Ca^{2+}$ concentration has been observed upon stimulation by wind, touch, abiotic stresses (cold, drought and salinity) or fungal elicitors. Several genes for $Ca^{2+}$ binding proteins with a conserved EF-hand domain have been isolated and showed increased expression level upon abiotic stress treatment (Frandsen G. et al., 1996 J Biol. Chem. 271:343-348; Takahashi S. et al., 2000 Pant Cell Physiol. 41:898-903).

The enigmatically named 14-3-3 proteins have been also the subject of considerable attention in recent years since they have been implicated in the regulation of diverse physiological processes in eukaryotes ranging from slime moulds to higher plants. In plants, many biological roles for 14-3-3 proteins have been suggested. The most significant of these include roles in the import of nuclear encoded chloroplast proteins, in the assembly of transcription factor complexes and in the regulation of enzyme activity in response to intracellular signal transduction cascades (Chung H J. et al., 1999 Tre. Plant Sci. 4:367-371). The native 14-3-3 proteins are homo- or heterodimers and, as each monomer has a binding site, a dimer can potentially bind two targets, promoting their association. Alternatively, target proteins may have more than one 14-3-3-binding site.

Several functions have been proposed for the 14-3-3 proteins in terms of involvement of plant stress tolerance. The 14-3-3 proteins could function as regulators in stress signal transduction. For example, RCI14A and RCI14B genes are induced by cold treatment in *Arabidopsis* and are highly homologous to the 14-3-3 proteins. The rise in the RCI transcript levels observed in response to cold treatment suggests a role for the RCI proteins in the stress signaling transduction pathway (Jarillo J A et al., 1994 Plant Mol. Biol. 25:693-704)

Due to the commercial consequences of environmental damage to crops, there is an interest in understanding the stress response signal transduction mechanisms in plants and how these can be manipulated to improve a plant's response to environmental damage. There is a need, therefore, to identify genes expressed in stress tolerant plants that have the capacity to confer stress resistance to its host plant and to other plant species. Newly generated stress tolerant plants will have many advantages, such as increasing the range that crop plants can be cultivated by, for example, decreasing the water requirements of a plant species.

SUMMARY OF THE INVENTION

This invention fulfills in part the need to identify new, unique signal transduction proteins capable of conferring stress tolerance to plants upon over-expression. The present invention provides a transgenic plant cell transformed by a Signal Transduction Stress-Related Protein (STSRP) coding nucleic acid, wherein expression of the nucleic acid sequence in the plant cell results in increased tolerance to environmental stress as compared to a wild type variety of the plant cell. Namely, described herein are the transcription factors 1) Phospholipase C-1 (PLC-1); 2) Phospholipase C-2 (PLC-2); 3) 14-3-3 Protein-1 (14-3-3P-1); 4) 14-3-3 Protein-1 (14-3-3P-2); and 5) $Ca^{2+}$ Binding Protein-1 (CBP-1), all from *Physcomitrella patens*.

The invention provides in some embodiments that the STSRP and coding nucleic acid are that found in members of the genus *Physcomitrella*. In another preferred embodiment, the nucleic acid and protein are from a *Physcomitrella patens*. The invention provides that the environmental stress can be salinity, drought, temperature, metal, chemical, pathogenic and oxidative stresses, or combinations thereof. In preferred embodiments, the environmental stress can be drought or cold temperature.

The invention further provides a seed produced by a transgenic plant transformed by a STSRP coding nucleic acid, wherein the plant is true breeding for increased tolerance to environmental stress as compared to a wild type variety of the plant. The invention further provides a seed produced by a transgenic plant expressing a STSRP, wherein the plant is true breeding for increased tolerance to environmental stress as compared to a wild type variety of the plant.

The invention further provides an agricultural product produced by any of the below-described transgenic plants, plant parts or seeds. The invention further provides an isolated STSRP as described below. The invention further provides an isolated STSRP coding nucleic acid, wherein the STSRP coding nucleic acid codes for a STSRP as described below.

The invention further provides an isolated recombinant expression vector comprising a STSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a STSRP coding nucleic acid, wherein expression of the nucleic acid in the plant results in increased tolerance to environmental stress as compared to a wild type variety of the plant comprising: (a) transforming a plant cell with an expression vector comprising a STSRP coding nucleic acid, and (b) generating from the plant cell a transgenic plant with an increased tolerance to environmental stress as compared to a wild type variety of the plant. In preferred embodiments, the STSRP and STSRP coding nucleic acid are as described below.

The present invention further provides a method of identifying a novel STSRP, comprising (a) raising a specific antibody response to a STSRP, or fragment thereof, as described above; (b) screening putative STSRP material with the antibody, wherein specific binding of the antibody to the material indicates the presence of a potentially novel STSRP; and (c) identifying from the bound material a novel STSRP in comparison to known STSRP. Alternatively, hybridization with nucleic acid probes as described below can be used to identify novel STSRP nucleic acids.

The present invention also provides methods of modifying stress tolerance of a plant comprising, modifying the expression of a STSRP in the plant, wherein the STSRP is as described below. The invention provides that this method can be performed such that the stress tolerance is either increased or decreased. Preferably, stress tolerance is increased in a plant via increasing expression of a STSRP.

DETAILED DESCRIPTION OF THE INVENTION

Figure 1:
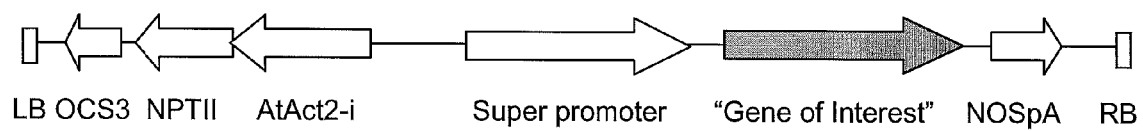
FIG. 1 shows a diagram of the plant expression vector pBPSSC022 containing the super promoter driving the expression of SEQ ID NO: 6, 7, 8, 9, or 10 ("Desired Gene"). The components are: NPTII kanamycin resistance gene (Bevan M, Nucleic Acids Res. 26: 8711-21, 1984), AtAct2-i promoter (An Y Q et al., Plant J 10: 107-121 1996), OCS3 terminator (During K, Transgenic Res. 3: 138-140, 1994), NOSpA terminator (Jefferson et al., EMBO J 6:3901-7 1987).
Figure 2:
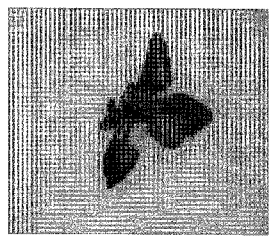
FIG. 2 shows the results of a drought stress test with over-expressing PpPLC-1 transgenic plants and wild-type *Arabidopsis* lines. The transgenic lines display a tolerant phenotype. Individual transformant lines are shown.
Figure 2:
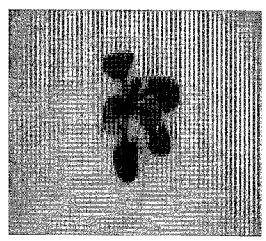
Figure 2:
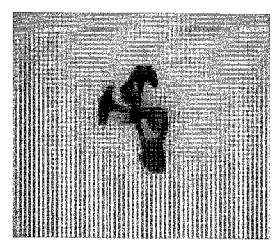
Figure 2:
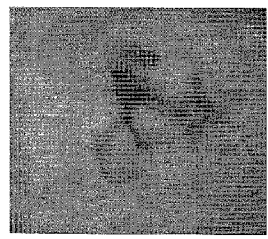
Figure 2:
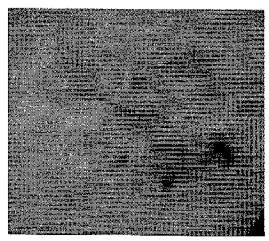
Figure 2:
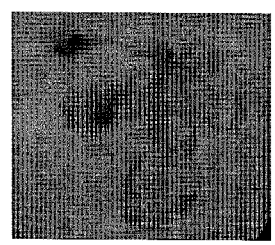
Figure 3:
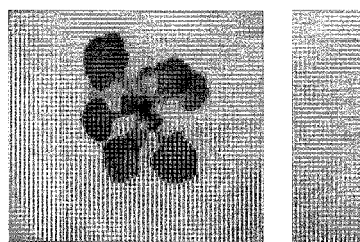
FIG. 3 shows the results of a drought stress test with over-expressing PpPLC-2 transgenic plants and wild-type *Arabidopsis* lines. The transgenic lines display a tolerant phenotype. Individual transformant lines are shown.
Figure 3:
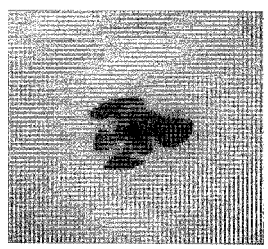
Figure 3:
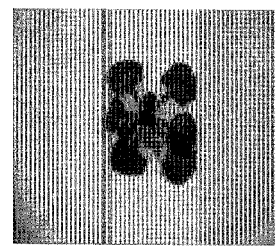
Figure 3:
Figure 3:
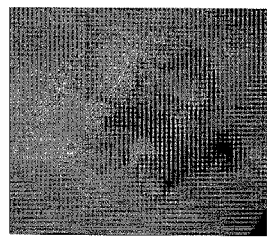
Figure 3:
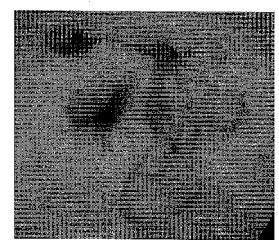
Figure 4:
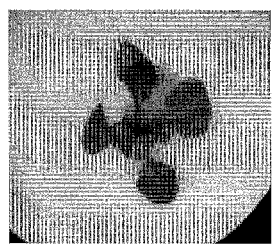
FIG. 4 shows the results of a drought stress test with over-expressing Pp14-3-3P-1 transgenic plants and wild-type *Arabidopsis* lines. The transgenic lines display a tolerant phenotype. Individual transformant lines are shown.
Figure 4:
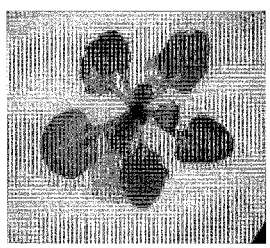
Figure 4:
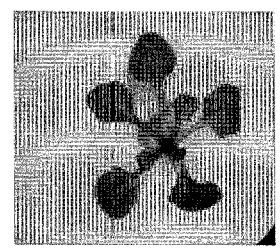
Figure 4:
Figure 4:
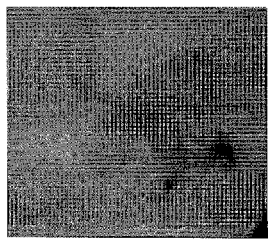
Figure 4:
Figure 5:
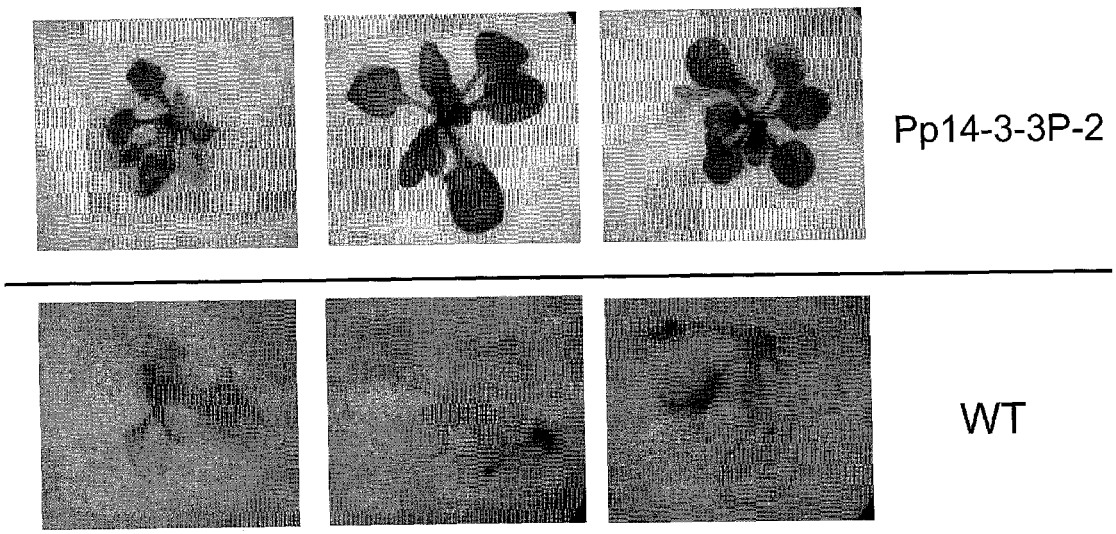
FIG. 5 shows the results of a drought stress test with over-expressing Pp14-3-3P-2 transgenic plants and wild-type *Arabidopsis* lines. The transgenic lines display a tolerant phenotype. Individual transformant lines are shown.
Figure 6:
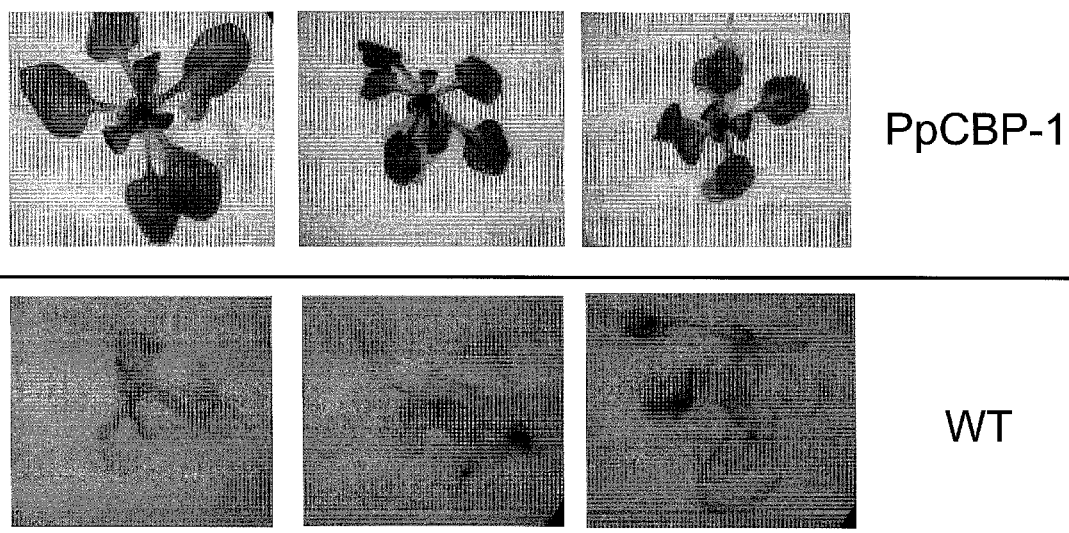
FIG. 6 shows the results of a drought stress test with over-expressing PpCBP-1 transgenic plants and wild-type *Arabidopsis* lines. The transgenic lines display a tolerant phenotype. Individual transformant lines are shown.
Figure 7:
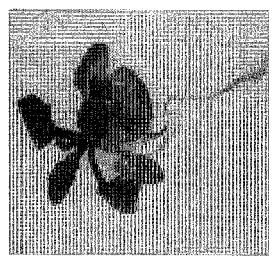
FIG. 7 shows the results of a freezing stress test with over-expressing PpPLC-2 transgenic plants and wild-type *Arabidopsis* lines. The transgenic lines display a tolerant phenotype. Individual transformant lines are shown.
Figure 7:
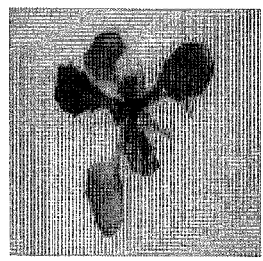
Figure 7:
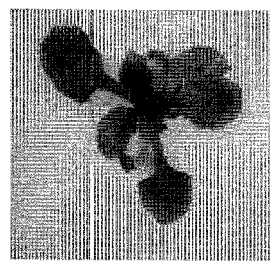
Figure 7:
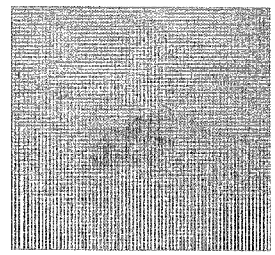
Figure 7:
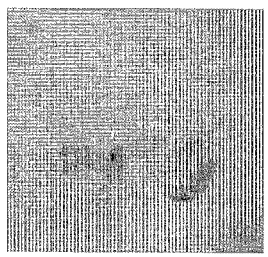
Figure 7:
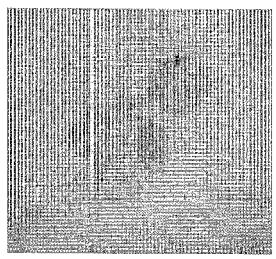
Figure 8:
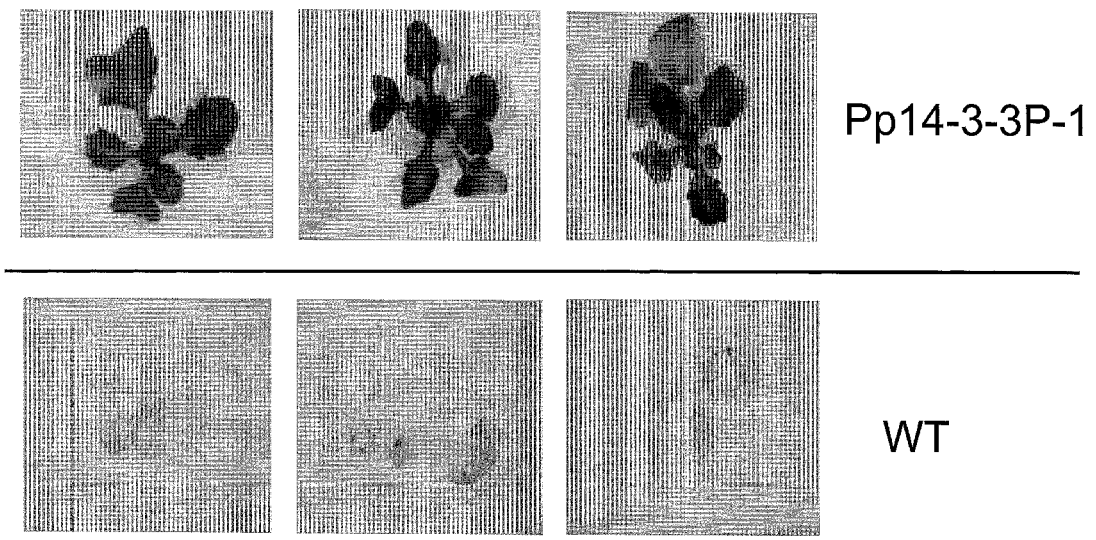
FIG. 8 shows the results of a freezing stress test with over-expressing Pp14-3-3P-1 transgenic plants and wild-type *Arabidopsis* lines. The transgenic lines display a tolerant phenotype. Individual transformant lines are shown.
Figure 9:
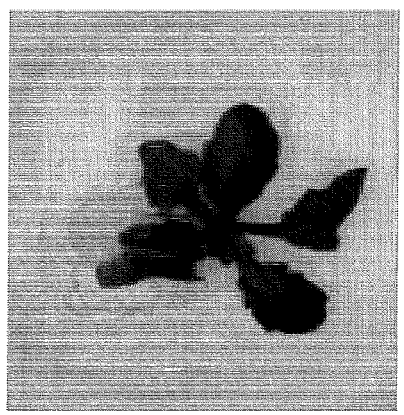
FIG. 9 shows the results of a freezing stress test with over-expressing PpCBP-1 transgenic plants and wild-type *Arabidopsis* lines. The transgenic lines display a tolerant phenotype. Individual transformant lines are shown.
Figure 9:
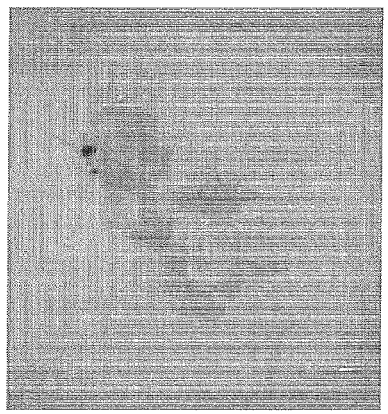
Figure 9:
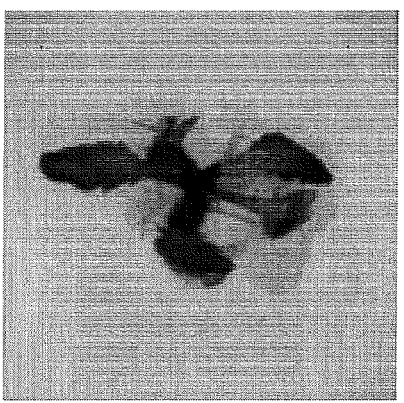
Figure 9:
Figure 9:
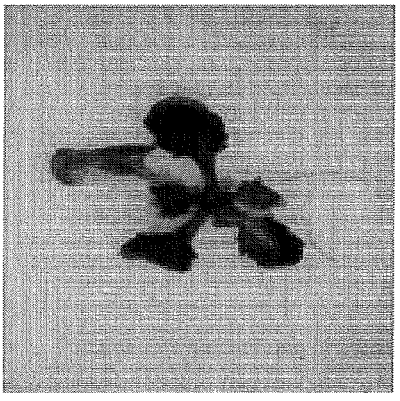
Figure 9:
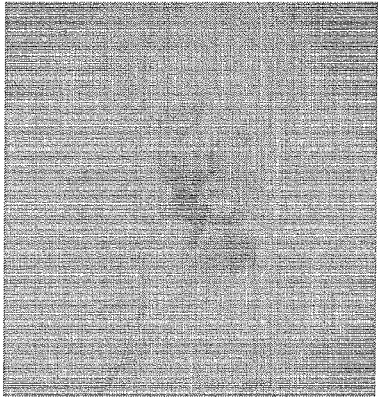

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as protein "Signal Transduction Stress-Related Proteins" (STSRPs), in no way limits the functionality of those sequences.

The present invention provides a transgenic plant cell transformed by a STSRP coding nucleic acid, wherein expression of the nucleic acid sequence in the plant cell results in increased tolerance to environmental stress as compared to a wild type variety of the plant cell. The invention further provides transgenic plant parts and transgenic plants containing the plant cells described herein. Also provided is a plant seed produced by a transgenic plant transformed by a STSRP coding nucleic acid, wherein the seed contains the STSRP coding nucleic acid, and wherein the plant is true breeding for increased tolerance to environmental stress as compared to a wild type variety of the plant. The invention further provides a seed produced by a transgenic plant expressing a STSRP, wherein the seed contains the STSRP, and wherein the plant is true breeding for increased tolerance to environmental stress as compared to a wild type variety of the plant. The invention also provides an agricultural product produced by any of the below-described transgenic plants, plant parts and plant seeds.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* STSRPs, PLC-1, PLC-2, 14-3-3P-1, 14-3-3P-2 and CBP-1, are useful for increasing a plant's tolerance to environmental stress. Accordingly, the present invention provides isolated STSRPs selected from the group consisting of PLC-1, PLC-2, 14-3-3P-1, 14-3-3P-2 and CBP-1, and homologs thereof. In preferred embodiments, the STSRP is selected from 1) a Phospholipase C-1 (PLC-1) protein as defined in SEQ ID NO:11; 2) a Phospholipase C-2 (PLC-2) protein as defined in SEQ ID NO:12; 3) a 14-3-3 Protein-1 (14-3-3P-1) protein as defined in SEQ ID NO:13; 4) a 14-3-3 Protein-1 (14-3-3P-2) protein as defined in SEQ ID NO:14; and 5) a $Ca^{2+}$ Binding Protein-1 (CBP-1) protein as defined in SEQ ID NO:15, and homologs and orthologs thereof. Homologs and orthologs of the amino acid sequences are defined below.

The STSRPs of the present invention are preferably produced by recombinant DNA techniques. For example, a nucleic acid molecule encoding the protein is cloned into an expression vector (as described above), the expression vector is introduced into a host cell (as described above) and the STSRP is expressed in the host cell. The STSRP can then be isolated from the cells by an appropriate purification scheme using standard protein purification techniques. Alternative to recombinant expression, a STSRP polypeptide, or peptide can be synthesized chemically using standard peptide synthesis techniques. Moreover, native STSRP can be isolated from cells (e.g., *Physcomitrella patens*), for example using an anti-STSRP antibody, which can be produced by standard techniques utilizing a STSRP or fragment thereof.

The invention further provides an isolated STSRP coding nucleic acid. The present invention includes STSRP coding nucleic acids that encode STSRPs as described herein. In preferred embodiments, the STSRP coding nucleic acid is selected from 1) a Phospholipase C-1 (PLC-1) nucleic acid as defined in SEQ ID NO:6; 2) a Phospholipase C-2 (PLC-2) nucleic acid as defined in SEQ ID NO:7; 3) a 14-3-3 Protein-1 (14-3-3P-1) nucleic acid as defined in SEQ ID NO:8; 4) a 14-3-3 Protein-1 (14-3-3P-2) nucleic acid as defined in SEQ ID NO:9; and 5) a $Ca^{2+}$ Binding Protein-1 (CBP-1) nucleic acid as defined in SEQ ID NO:10 and homologs and orthologs thereof. Homologs and orthologs of the nucleotide sequences are defined below. In one preferred embodiment, the nucleic acid and protein are isolated from the plant genus *Physcomitrella*. In another preferred embodiment, the nucleic acid and protein are from a *Physcomitrella patens* (*P. patens*) plant.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, or temperature, or combinations thereof, and in particular, can be high salinity, low water content or low temperature. It is also to be understood that as used in the specification and in the claims, "a" or "an" can mean one or more, depending upon the context in which it is used. Thus, for example, reference to "a cell" can mean that at least one cell can be utilized.

As also used herein, the terms "nucleic acid" and "nucleic acid molecule" are intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA.

An "isolated" nucleic acid molecule is one that is substantially separated from other nucleic acid molecules which are present in the natural source of the nucleic acid. Preferably, an "isolated" nucleic acid is free of some of the sequences which naturally flank the nucleic acid (i.e., sequences located at the 5' and 3' ends of the nucleic acid) in the genomic DNA of the organism from which the nucleic acid is derived. For example, in various embodiments, the isolated STSRP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Physcomitrella patens* cell). Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A nucleic acid molecule of the present invention, e.g., a nucleic acid molecule having a nucleotide sequence of SEQ ID NO:6, SEQ ID NO:7, SEQ ID NO:8, SEQ ID NO:9, SEQ ID NO:10, or a portion thereof, can be isolated using standard molecular biology techniques and the sequence information provided herein. For example, a *P. patens* STSRP cDNA can be isolated from a *P. patens* library using all or portion of one of the sequences of SEQ ID NO:1, SEQ ID NO:2, SEQ ID NO:3, SEQ ID NO:4 or SEQ ID NO:5. Moreover, a nucleic acid molecule encompassing all or a portion of one of the sequences of SEQ ID NO:1, SEQ ID NO:2, SEQ ID NO:3, SEQ ID NO:4 and SEQ ID NO:5 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:2, SEQ ID NO:3, SEQ ID NO:4 and SEQ ID NO:5. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a STSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:6, SEQ ID NO:7, SEQ ID NO:8, SEQ ID NO:9 and SEQ ID NO:10. These cDNAs comprise sequences encoding the STSRPs (i.e., the "coding region", indicated in Table 1), as well as 5' untranslated sequences and 3' untranslated sequences. It is to be understood that SEQ ID NO:6, SEQ ID NO:7, SEQ ID NO:8, SEQ ID NO:9 and SEQ ID NO:10 comprise both coding regions and 5' and 3' untranslated regions. Alternatively, the nucleic acid molecules of the present invention can comprise only the coding region of any of the sequences in SEQ ID NO:6, SEQ ID NO:7, SEQ ID NO:8, SEQ ID NO:9 or SEQ ID NO:10 or can contain whole genomic fragments isolated from genomic DNA. A coding region of these sequences is indicated as "ORF position". The present invention also includes STSRP coding nucleic acids that encode STSRPs as described herein. Preferred is a STSRP coding nucleic acid that encodes a STSRP selected from the group consisting of, PLC-1 (SEQ ID NO:11); PLC-2 (SEQ ID NO:12); 14-3-3P-1 (SEQ ID NO:13); 14-3-3P-2 (SEQ ID NO:14) and CBP-1 (SEQ ID NO:15).

Moreover, the nucleic acid molecule of the invention can comprise only a portion of the coding region of one of the sequences in SEQ ID NO:6, SEQ ID NO:7, SEQ ID NO:8, SEQ ID NO:9 and SEQ ID NO:10, for example, a fragment which can be used as a probe or primer or a fragment encoding a biologically active portion of a STSRP. The nucleotide sequences determined from the cloning of the STSRP genes from *P. patens* allow for the generation of probes and primers designed for use in identifying and/or cloning STSRP homologs in other cell types and organisms, as well as STSRP homologs from other mosses and related species.

Portions of proteins encoded by the STSRP nucleic acid molecules of the invention are preferably biologically active portions of one of the STSRPs described herein. As used herein, the term "biologically active portion of" a STSRP is intended to include a portion, e.g., a domain/motif, of a STSRP that participates in a stress tolerance response in a plant, has an activity as set forth in Table 1, or participates in the transcription of a protein involved in a stress tolerance response in a plant. To determine whether a STSRP, or a biologically active portion thereof, can participate in transcription of a protein involved in a stress tolerance response in a plant, or whether repression of a STSRP results in increased stress tolerance in a plant, a stress analysis of a plant comprising the STSRP may be performed. Such analysis methods are well known to those skilled in the art, as detailed in Example 7. More specifically, nucleic acid fragments encoding biologically active portions of a STSRP can be prepared by isolating a portion of one of the sequences in SEQ ID NO:11, SEQ ID NO:12, SEQ ID NO:13, SEQ ID NO:14 and SEQ ID NO:15, expressing the encoded portion of the STSRP or peptide (e.g., by recombinant expression in vitro) and assessing the activity of the encoded portion of the STSRP or peptide.

Biologically active portions of a STSRP are encompassed by the present invention and include peptides comprising amino acid sequences derived from the amino acid sequence of a STSRP, e.g., an amino acid sequence of SEQ ID NO:11, SEQ ID NO:12, SEQ ID NO:13, SEQ ID NO:14 or SEQ ID NO:15, or the amino acid sequence of a protein homologous to a STSRP, which include fewer amino acids than a full length STSRP or the full length protein which is homologous to a STSRP, and exhibit at least one activity of a STSRP. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a STSRP. Moreover, other biologically active portions in which other regions of the protein are deleted, can be prepared by recombinant techniques and evaluated for one or more of the activities described herein. Preferably, the biologically active portions of a STSRP include one or more selected domains/motifs or portions thereof having biological activity.

The invention also provides STSRP chimeric or fusion proteins. As used herein, a STSRP "chimeric protein" or "fusion protein" comprises a STSRP polypeptide operatively linked to a non-STSRP polypeptide. A STSRP polypeptide refers to a polypeptide having an amino acid sequence corresponding to a STSRP, whereas a non-STSRP polypeptide refers to a polypeptide having an amino acid sequence corresponding to a protein which is not substantially homologous to the STSRP, e.g., a protein that is different from the STSRP and is derived from the same or a different organism. Within the fusion protein, the term "operatively linked" is intended to indicate that the STSRP polypeptide and the non-STSRP polypeptide are fused to each other so that both sequences fulfill the proposed function attributed to the sequence used. The non-STSRP polypeptide can be fused to the N-terminus or C-terminus of the STSRP polypeptide. For example, in one embodiment, the fusion protein is a GST-STSRP fusion protein in which the STSRP sequences are fused to the C-terminus of the GST sequences. Such fusion proteins can facilitate the purification of recombinant STSRPs. In another embodiment, the fusion protein is a STSRP containing a heterologous signal sequence at its N-terminus. In certain host cells (e.g., mammalian host cells), expression and/or secretion of a STSRP can be increased through use of a heterologous signal sequence.

Preferably, a STSRP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, Eds. Ausubel et al. John Wiley & Sons: 1992). Moreover, many expression vectors are commercially available that already encode a fusion moiety (e.g., a GST polypeptide). A STSRP encoding nucleic acid can be cloned into such an expression vector such that the fusion moiety is linked in-frame to the STSRP.

In addition to fragments and fusion proteins of the STSRPs described herein, the present invention includes homologs and analogs of naturally occurring STSRPs and STSRP encoding nucleic acids in a plant. "Homologs" are defined herein as two nucleic acids or proteins that have similar, or "homologous", nucleotide or amino acid sequences, respectively. Homologs include allelic variants, orthologs, paralogs, agonists and antagonists of STSRPs as defined hereafter. The term "homolog" further encompasses nucleic acid molecules that differ from one of the nucleotide sequences shown in SEQ ID NO:6, SEQ ID NO:7, SEQ ID NO:8, SEQ ID NO:9 and SEQ ID NO:10 (and portions thereof) due to degeneracy of the genetic code and thus encode the same STSRP as that encoded by the nucleotide sequences shown in SEQ ID NO:6, SEQ ID NO:7, SEQ ID NO:8, SEQ ID NO:9 or SEQ ID NO:10. As used herein a "naturally occurring" STSRP refers to a STSRP amino acid sequence that occurs in nature. Preferably, a naturally occurring STSRP comprises an amino acid sequence selected from the group consisting of SEQ ID NO:11, SEQ ID NO:12, SEQ ID NO:13, SEQ ID NO:14 and SEQ ID NO:15.

An agonist of the STSRP can retain substantially the same, or a subset, of the biological activities of the STSRP. An antagonist of the STSRP can inhibit one or more of the activities of the naturally occurring form of the STSRP. For example, the STSRP antagonist can competitively bind to a downstream or upstream member of the cell membrane component metabolic cascade that includes the STSRP, or bind to a STSRP that mediates transport of compounds across such membranes, thereby preventing translocation from taking place.

Nucleic acid molecules corresponding to natural allelic variants and analogs, orthologs and paralogs of a STSRP cDNA can be isolated based on their identity to the *Physcomitrella patens* STSRP nucleic acids described herein using STSRP cDNAs, or a portion thereof, as a hybridization probe according to standard hybridization techniques under stringent hybridization conditions. In an alternative embodiment, homologs of the STSRP can be identified by screening combinatorial libraries of mutants, e.g., truncation mutants, of the STSRP for STSRP agonist or antagonist activity. In one embodiment, a variegated library of STSRP variants is generated by combinatorial mutagenesis at the nucleic acid level and is encoded by a variegated gene library. A variegated library of STSRP variants can be produced by, for example, enzymatically ligating a mixture of synthetic oligonucleotides into gene sequences such that a degenerate set of potential STSRP sequences is expressible as individual polypeptides, or alternatively, as a set of larger fusion proteins (e.g., for phage display) containing the set of STSRP sequences therein. There are a variety of methods that can be used to produce libraries of potential STSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential STSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477).

In addition, libraries of fragments of the STSRP coding regions can be used to generate a variegated population of STSRP fragments for screening and subsequent selection of homologs of a STSRP. In one embodiment, a library of coding sequence fragments can be generated by treating a double stranded PCR fragment of a STSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the STSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of STSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify STSRP homologs (Arkin and Yourvan, 1992 PNAS 89:7811-7815; Delgrave et al., 1993 Protein Engineering 6(3):327-331). In another embodiment, cell based assays can be exploited to analyze a variegated STSRP library, using methods well known in the art. The present invention further provides a method of identifying a novel STSRP, comprising (a) raising a specific antibody response to a STSRP, or a fragment thereof, as described above; (b) screening putative STSRP material with the antibody, wherein specific binding of the antibody to the material indicates the presence of a potentially novel STSRP; and (c) analyzing the bound material in comparison to known STSRP, to determine its novelty.

To determine the percent homology of two amino acid sequences (e.g., one of the sequences of SEQ ID NO:11, SEQ ID NO:12, SEQ ID NO:13, SEQ ID NO:14 and SEQ ID NO:15 and a mutant form thereof), the sequences are aligned for optimal comparison purposes (e.g., gaps can be introduced in the sequence of one protein or nucleic acid for optimal alignment with the other protein or nucleic acid). The amino acid residues at corresponding amino acid positions are then compared. When a position in one sequence (e.g., one of the sequences of SEQ ID NO:11, SEQ ID NO:12, SEQ ID NO:13, SEQ ID NO:14 and SEQ ID NO:15) is occupied by the same amino acid residue as the corresponding position in the other sequence (e.g., a mutant form of the sequence selected from the polypeptide of SEQ ID NO:11, SEQ ID NO:12, SEQ ID NO:13, SEQ ID NO:14 and SEQ ID NO:15), then the molecules are homologous at that position (i.e., as used herein amino acid or nucleic acid "homology" is equivalent to amino acid or nucleic acid "identity"). The same type of comparison can be made between two nucleic acid sequences.

The percent homology between the two sequences is a function of the number of identical positions shared by the sequences (i.e., % homology=numbers of identical positions/total numbers of positions×100). Preferably, the amino acid sequences included in the present invention are at least about 50-60%, preferably at least about 60-70%, and more preferably at least about 70-80%, 80-90%, 90-95%, and most preferably at least about 96%, 97%, 98%, 99% or more homologous to an entire amino acid sequence shown in SEQ ID NO:11, SEQ ID NO:12, SEQ ID NO:13, SEQ ID NO:14 or SEQ ID NO:15. In yet another embodiment, at least about 50-60%, preferably at least about 60-70%, and more preferably at least about 70-80%, 80-90%, 90-95%, and most preferably at least about 96%, 97%, 98%, 99% or more homologous to an entire amino acid sequence encoded by a nucleic acid sequence shown in SEQ ID NO:6, SEQ ID NO:7, SEQ ID NO:8, SEQ ID NO:9 or SEQ ID NO:10. In other embodiments, the preferable length of sequence comparison for proteins is at least 15 amino acid residues, more preferably at least 25 amino acid residues, and most preferably at least 35 amino acid residues.

In another preferred embodiment, an isolated nucleic acid molecule of the invention comprises a nucleotide sequence which is at least about 50-60%, preferably at least about 60-70%, more preferably at least about 70-80%, 80-90%, or 90-95%, and even more preferably at least about 95%, 96%, 97%, 98%, 99% or more homologous to a nucleotide sequence shown in SEQ ID NO:6, SEQ ID NO:7, SEQ ID NO:8, SEQ ID NO:9 or SEQ ID NO:10, or a portion thereof. The preferable length of sequence comparison for nucleic acids is at least 75 nucleotides, more preferably at least 100 nucleotides and most preferably the entire length of the coding region.

It is also preferable that the homologous nucleic acid molecule of the invention encodes a protein or portion thereof which includes an amino acid sequence which is sufficiently homologous to an amino acid sequence of SEQ ID NO:11, SEQ ID NO:12, SEQ ID NO:13, SEQ ID NO:14 or SEQ ID NO:15 such that the protein or portion thereof maintains the same or a similar function as the amino acid sequence to which it is compared. Functions of the STSRP amino acid sequences of the present invention include the ability to participate in a stress tolerance response in a plant, or more particularly, to participate in the transcription of a protein involved in a stress tolerance response in a *Physcomitrella patens* plant. Examples of such activities are described in Table 1.

In addition to the above described methods, a determination of the percent homology between two sequences can be accomplished using a mathematical algorithm. A preferred, non-limiting example of a mathematical algorithm utilized for the comparison of two sequences is the algorithm of Karlin and Altschul (1990 Proc. Natl. Acad. Sci. USA 90:5873-5877). Such an algorithm is incorporated into the NBLAST and XBLAST programs of Altschul, et al. (1990 J. Mol. Biol. 215:403-410).

BLAST nucleic acid searches can be performed with the NBLAST program, score=100, wordlength=12 to obtain nucleic acid sequences homologous to the STSRP nucleic acid molecules of the invention. Additionally, BLAST protein searches can be performed with the XBLAST program, score=50, wordlength=3 to obtain amino acid sequences homologous to STSRPs of the present invention. To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used to obtain amino acid sequences homologous to the STSRPs of the present invention. To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM 120 weight residue table, a gap length penalty of 12 and a gap penalty of 4 can be used.

Finally, homology between nucleic acid sequences can also be determined using hybridization techniques known to those of skill in the art. Accordingly, an isolated nucleic acid molecule of the invention comprises a nucleotide sequence which hybridizes, e.g., under stringent conditions, to one of the nucleotide sequences shown in SEQ ID NO:6, SEQ ID NO:7, SEQ ID NO:8, SEQ ID NO:9 and SEQ ID NO:10, or a portion thereof. More particularly, an isolated nucleic acid molecule of the invention is at least 15 nucleotides in length and hybridizes under stringent conditions to the nucleic acid molecule comprising a nucleotide sequence of SEQ ID NO:6, SEQ ID NO:7, SEQ ID NO:8, SEQ ID NO:9 or SEQ ID NO:10. In other embodiments, the nucleic acid is at least 30, 50, 100, 250 or more nucleotides in length.

As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, 6.3.1-6.3.6, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a sequence of SEQ ID NO:6, SEQ ID NO:7, SEQ ID NO:8, SEQ ID NO:9 or SEQ ID NO:10 corresponds to a naturally occurring nucleic acid molecule. As used herein, a "naturally occurring" nucleic acid molecule refers to an RNA or DNA molecule having a nucleotide sequence that occurs in nature (e.g., encodes a natural protein). In one embodiment, the nucleic acid encodes a naturally occurring *Physcomitrella patens* STSRP.

Using the above-described methods, and others known to those of skill in the art, one of ordinary skill in the art can isolate homologs of the STSRPs comprising amino acid sequences shown in SEQ ID NO:11, SEQ ID NO:12, SEQ ID NO:13, SEQ ID NO:14 or SEQ ID NO:15. One subset of these homologs is allelic variants. As used herein, the term "allelic variant" refers to a nucleotide sequence containing polymorphisms that lead to changes in the amino acid sequences of a STSRP and that exist within a natural population (e.g., a plant species or variety). Such natural allelic variations can typically result in 1-5% variance in a STSRP nucleic acid. Allelic variants can be identified by sequencing the nucleic acid sequence of interest in a number of different plants, which can be readily carried out by using hybridization probes to identify the same STSRP genetic locus in those plants. Any and all such nucleic acid variations and resulting amino acid polymorphisms or variations in a STSRP that are the result of natural allelic variation and that do not alter the functional activity of a STSRP, are intended to be within the scope of the invention.

Moreover, nucleic acid molecules encoding STSRPs from the same or other species such as STSRP analogs, orthologs and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode proteins having the same or similar functions. As also used herein, the term "paralogs" refers to two nucleic acids that are related by duplication within a genome. Paralogs usually have different functions, but these functions may be related (Tatusov, R. L. et al. 1997 Science 278(5338):631-637). Analogs, orthologs and paralogs of a naturally occurring STSRP can differ from the naturally occurring STSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably 90%, and most preferably 95%, 96%, 97%, 98% or even 99% identity or homology with all or part of a naturally occurring STSRP amino acid sequence and will exhibit a function similar to a STSRP. Orthologs of the present invention are also preferably capable of participating in the stress response in plants. In one embodiment, the STSRP orthologs maintain the ability to participate in the metabolism of compounds necessary for the construction of cellular membranes in *Physcomitrella patens*, or in the transport of molecules across these membranes.

In addition to naturally-occurring variants of a STSRP sequence that may exist in the population, the skilled artisan will further appreciate that changes can be introduced by mutation into a nucleotide sequence of SEQ ID NO:6, SEQ ID NO:7, SEQ ID NO:8, SEQ ID NO:9 or SEQ ID NO:10, thereby leading to changes in the amino acid sequence of the encoded STSRP, without altering the functional ability of the STSRP. For example, nucleotide substitutions leading to amino acid substitutions at "non-essential" amino acid residues can be made in a sequence of SEQ ID NO:6, SEQ ID NO:7, SEQ ID NO:8, SEQ ID NO:9 or SEQ ID NO:10. A "non-essential" amino acid residue is a residue that can be altered from the wild-type sequence of one of the STSRPs without altering the activity of said STSRP, whereas an "essential" amino acid residue is required for STSRP activity. Other amino acid residues, however, (e.g., those that are not conserved or only semi-conserved in the domain having STSRP activity) may not be essential for activity and thus are likely to be amenable to alteration without altering STSRP activity.

Accordingly, another aspect of the invention pertains to nucleic acid molecules encoding STSRPs that contain changes in amino acid residues that are not essential for STSRP activity. Such STSRPs differ in amino acid sequence from a sequence contained in SEQ ID NO:11, SEQ ID NO:12, SEQ ID NO:13, SEQ ID NO:14 or SEQ ID NO:15, yet retain at least one of the STSRP activities described herein. In one embodiment, the isolated nucleic acid molecule comprises a nucleotide sequence encoding a protein, wherein the protein comprises an amino acid sequence at least about 50% homologous to an amino acid sequence of SEQ ID NO:11, SEQ ID NO:12, SEQ ID NO:13, SEQ ID NO:14 or SEQ ID NO:15. Preferably, the protein encoded by the nucleic acid molecule is at least about 50-60% homologous to one of the sequences of SEQ ID NO:11, SEQ ID NO:12, SEQ ID NO:13, SEQ ID NO:14 and SEQ ID NO:15, more preferably at least about 60-70% homologous to one of the sequences of SEQ ID NO:11, SEQ ID NO:12, SEQ ID NO:13, SEQ ID NO:14 and SEQ ID NO:15, even more preferably at least about 70-80%, 80-90%, 90-95% homologous to one of the sequences of SEQ ID NO:11, SEQ ID NO:12, SEQ ID NO:13, SEQ ID NO:14 and SEQ ID NO:15, and most preferably at least about 96%, 97%, 98%, or 99% homologous to one of the sequences of SEQ ID NO:11, SEQ ID NO:12, SEQ ID NO:13, SEQ ID NO:14 and SEQ ID NO:15. The preferred STSRP homologs of the present invention are preferably capable of participating in the a stress tolerance response in a plant, or more particularly, participating in the transcription of a protein involved in a stress tolerance response in a *Physcomitrella patens* plant, or have one or more activities set forth in Table 1.

An isolated nucleic acid molecule encoding a STSRP homologous to a protein sequence of SEQ ID NO:11, SEQ ID NO:12, SEQ ID NO:13, SEQ ID NO:14 or SEQ ID NO:15 can be created by introducing one or more nucleotide substitutions, additions or deletions into a nucleotide sequence of SEQ ID NO:6, SEQ ID NO:7, SEQ ID NO:8, SEQ ID NO:9 or SEQ ID NO:10 such that one or more amino acid substitutions, additions or deletions are introduced into the encoded protein. Mutations can be introduced into one of the sequences of SEQ ID NO:6, SEQ ID NO:7, SEQ ID NO:8, SEQ ID NO:9 and SEQ ID NO:10 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a STSRP is preferably replaced with another amino acid residue from the same side chain family. Alternatively, in another embodiment, mutations can be introduced randomly along all or part of a STSRP coding sequence, such as by saturation mutagenesis, and the resultant mutants can be screened for a STSRP activity described herein to identify mutants that retain STSRP activity. Following mutagenesis of one of the sequences of SEQ ID NO:6, SEQ ID NO:7, SEQ, ID NO:8, SEQ ID NO:9 and SEQ ID NO:10, the encoded protein can be expressed recombinantly and the activity of the protein can be determined by analyzing the stress tolerance of a plant expressing the protein as described in Example 7.

In addition to the nucleic acid molecules encoding the STSRPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire STSRP coding strand, or to only a portion thereof. In one embodiment, an antisense nucleic acid molecule is antisense to a "coding region" of the coding strand of a nucleotide sequence encoding a STSRP. The term "coding region" refers to the region of the nucleotide sequence comprising codons that are translated into amino acid residues (e.g., the entire coding region of ,,,,, comprises nucleotides 1 to . . . ). In another embodiment, the antisense nucleic acid molecule is antisense to a "noncoding region" of the coding strand of a nucleotide sequence encoding a STSRP. The term "noncoding region" refers to 5' and 3' sequences that flank the coding region that are not translated into amino acids (i.e., also referred to as 5' and 3' untranslated regions).

In a preferred embodiment, an isolated nucleic acid molecule of the invention comprises a nucleic acid molecule which is a complement of one of the nucleotide sequences shown in SEQ ID NO:6, SEQ ID NO:7, SEQ ID NO:8, SEQ ID NO:9 and SEQ ID NO:10, or a portion thereof. A nucleic acid molecule that is complementary to one of the nucleotide sequences shown in SEQ ID NO:6, SEQ ID NO:7, SEQ ID NO:8, SEQ ID NO:9 and SEQ ID NO:10 is one which is sufficiently complementary to one of the nucleotide sequences shown in SEQ ID NO:6, SEQ ID NO:7, SEQ ID NO:8, SEQ ID NO:9 and SEQ ID NO:10 such that it can hybridize to one of the nucleotide sequences shown in SEQ ID NO:6, SEQ ID NO:7, SEQ ID NO:8, SEQ ID NO:9 and SEQ ID NO:10, thereby forming a stable duplex.

Given the coding strand sequences encoding the STSRPs disclosed herein (e.g., the sequences set forth in SEQ ID NO:6, SEQ ID NO:7, SEQ ID NO:8, SEQ ID NO:9 and SEQ ID NO:10), antisense nucleic acids of the invention can be designed according to the rules of Watson and Crick base pairing. The antisense nucleic acid molecule can be complementary to the entire coding region of STSRP mRNA, but more preferably is an oligonucleotide which is antisense to only a portion of the coding or noncoding region of STSRP mRNA. For example, the antisense oligonucleotide can be complementary to the region surrounding the translation start site of STSRP mRNA. An antisense oligonucleotide can be, for example, about 5, 10, 15, 20, 25, 30, 35, 40, 45 or 50 nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a STSRP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

In yet another embodiment, the antisense nucleic acid molecule of the invention is an α-anomeric nucleic acid molecule.

An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625-6641). The antisense nucleic acid molecule can also comprise a 2'-o-methylribonucleotide (Inoue et al., 1987 Nucleic Acids Res. 15:6131-6148) or a chimeric RNA-DNA analogue (Inoue et al., 1987 FEBS Lett. 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes described in Haselhoff and Gerlach, 1988 Nature 334:585-591) can be used to catalytically cleave STSRP mRNA transcripts to thereby inhibit translation of STSRP mRNA. A ribozyme having specificity for a STSRP-encoding nucleic acid can be designed based upon the nucleotide sequence of a STSRP cDNA, as disclosed herein (i.e., SEQ ID NO:6, SEQ ID NO:7, SEQ ID NO:8, SEQ ID NO:9 or SEQ ID NO:10) or on the basis of a heterologous sequence to be isolated according to methods taught in this invention. For example, a derivative of a *Tetrahymena* L-19 IVS RNA can be constructed in which the nucleotide sequence of the active site is complementary to the nucleotide sequence to be cleaved in a STSRP-encoding mRNA. See, e.g., Cech et al. U.S. Pat. No. 4,987,071 and Cech et al. U.S. Pat. No. 5,116,742. Alternatively, STSRP mRNA can be used to select a catalytic RNA having a specific ribonuclease activity from a pool of RNA molecules. See, e.g., Bartel, D. and Szostak, J. W., 1993 Science 261:1411-1418.

Alternatively, STSRP gene expression can be inhibited by targeting nucleotide sequences complementary to the regulatory region of a STSRP nucleotide sequence (e.g., a STSRP promoter and/or enhancer) to form triple helical structures that prevent transcription of a STSRP gene in target cells. See generally, Helene, C., 1991 Anticancer Drug Des. 6(6):569-84; Helene, C. et al., 1992 Ann. N.Y. Acad. Sci. 660:27-36; and Maher, L. J., 1992 Bioassays 14(12):807-15.

In addition to the STSRP nucleic acids and proteins described above, the present invention encompasses these nucleic acids and proteins attached to a moiety. These moieties include, but are not limited to, detection moieties, hybridization moieties, purification moieties, delivery moieties, reaction moieties, binding moieties, and the like. One typical group of nucleic acids attached to a moiety include probes and primers. The probes and primers comprise a region of nucleotide sequence that hybridizes under stringent conditions to at least about 12, preferably about 25, more preferably about 40, 50 or 75 consecutive nucleotides of a sense strand of one of the sequences set forth in SEQ ID NO:6, SEQ ID NO:7, SEQ ID NO:8, SEQ ID NO:9 and SEQ ID NO:10, an anti-sense sequence of one of the sequences set forth in SEQ ID NO:6, SEQ ID NO:7, SEQ ID NO:8, SEQ ID NO:9 and SEQ ID NO:10, or naturally occurring mutants thereof. Primers based on a nucleotide sequence of SEQ ID NO:6, SEQ ID NO:7, SEQ ID NO:8, SEQ ID NO:9 or SEQ ID NO:10 can be used in PCR reactions to clone STSRP homologs. Probes based on the STSRP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a STSRP, such as by measuring a level of a STSRP-encoding nucleic acid, in a sample of cells, e.g., detecting STSRP mRNA levels or determining whether a genomic STSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: N.Y.). This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317-326. To assess the presence or relative quantity of protein translated from this mRNA, standard techniques, such as a Western blot, may be employed. These techniques are well known to one of ordinary skill in the art. (See, for example, Ausubel et al., 1988 Current Protocols in Molecular Biology, Wiley: N.Y.).

The invention further provides an isolated recombinant expression vector comprising a STSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., STSRPs, mutant forms of STSRPs, fusion proteins, etc.).

The recombinant expression vectors of the invention can be designed for expression of STSRPs in prokaryotic or eukaryotic cells. For example, STSRP genes can be expressed in bacterial cells such as *C. glutamicum*, insect cells (using baculovirus expression vectors), yeast and other fungal cells (see Romanos, M. A. et al., 1992 Foreign gene expression in yeast: a review, Yeast 8:423-488; van den Hondel, C. A. M. J. J. et al., 1991 Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J., 1991 Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999 Marine Biotechnology 1(3):239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella,* and *Stylonychia*, especially of the genus *Stylonychia lemnae* with vectors following a transformation method as described in WO 98/01572 and multicellular plant cells (see Schmidt, R. and Willmitzer, L., 1988 High efficiency *Agrobacterium tumefaciens*-mediated transformation of *Arabidopsis thaliana* leaf and cotyledon explants, Plant Cell Rep. 583-586); Plant Molecular Biology and Biotechnology, C Press, Boca Raton, Fla., chapter 6/7, S.71-119 (1993); F. F. White, B. Jenes et al., Techniques for Gene Transfer, in: Transgenic Plants, Vol. 1, Engineering and Utilization, eds. Kung und R. Wu, 128-43, Academic Press: 1993; Potrykus, 1991 Annu. Rev. Plant Physiol. Plant Molec. Biol. 42:205-225 and references cited therein) or mammalian cells. Suitable host cells are discussed further in Goeddel, *Gene Expression Technology: Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of a recombinant protein; 2) to increase the solubility of a recombinant protein; and 3) to aid in the purification of a recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S., 1988 Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the STSRP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant STSRP unfused to GST can be recovered by cleavage of the fusion protein with thrombin.

Examples of suitable inducible non-fusion *E. coli* expression vectors include pTrc (Amann et al., 1988 Gene 69:301-315) and pET 11d (Studier et al., *Gene Expression Technology. Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, S., *Gene Expression Technology. Methods in Enzymology* 185, Academic Press, San Diego, Calif. (1990) 119-128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992 Nucleic Acids Res. 20:2111-2118). Such alteration of nucleic acid sequences of the invention can be carried out by standard DNA synthesis techniques.

In another embodiment, the STSRP expression vector is a yeast expression vector. Examples of vectors for expression in yeast *S. cerevisiae* include pYepSec1 (Baldari, et al., 1987 EMBO J. 6:229-234), pMFa (Kurjan and Herskowitz, 1982 Cell 30:933-943), pJRY88 (Schultz et al., 1987 Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge.

Alternatively, the STSRPs of the invention can be expressed in insect cells using baculovirus expression vectors. Baculovirus vectors available for expression of proteins in cultured insect cells (e.g., Sf 9 cells) include the pAc series (Smith et al., 1983 Mol. Cell Biol. 3:2156-2165) and the pVL series (Lucklow and Summers, 1989 Virology 170:31-39).

In yet another embodiment, a STSRP nucleic acid of the invention is expressed in mammalian cells using a mammalian expression vector. Examples of mammalian expression vectors include pCDM8 (Seed, B., 1987 Nature 329:840) and pMT2PC (Kaufman et al., 1987 EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd ed., Cold Spring Harbor Laboratory,* Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987 Genes Dev. 1:268-277), lymphoid-specific promoters (Calame and Eaton, 1988 Adv. Immunol. 43:235-275), in particular promoters of T cell receptors (Winoto and Baltimore, 1989 EMBO J. 8:729-733) and immunoglobulins (Banerji et al., 1983 Cell 33:729-740; Queen and Baltimore, 1983 Cell 33:741-748), neuron-specific promoters (e.g., the neurofilament promoter; Byrne and Ruddle, 1989 *PNAS* 86:5473-5477), pancreas-specific promoters (Edlund et al., 1985 Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, 1990 Science 249:374-379) and the fetoprotein promoter (Campes and Tilghman, 1989 Genes Dev. 3:537-546).

In another embodiment, the STSRPs of the invention may be expressed in unicellular plant cells (such as algae) (see Falciatore et al., 1999 Marine Biotechnology 1(3):239-251 and references therein) and plant cells from higher plants (e.g., the spermatophytes, such as crop plants). Examples of plant expression vectors include those detailed in: Becker, D., Kemper, E., Schell, J. and Masterson, R., 1992 New plant binary vectors with selectable markers located proximal to the left border, Plant Mol. Biol. 20: 1195-1197; and Bevan, M. W., 1984 Binary *Agrobacterium* vectors for plant transformation, Nucl. Acid. Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38.

A plant expression cassette preferably contains regulatory sequences capable of driving gene expression in plant cells and operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., 1987 Nucl. Acids Research 15:8693-8711).

Plant gene expression has to be operably linked to an appropriate promoter conferring gene expression in a timely, cell or tissue specific manner. Preferred are promoters driving constitutive expression (Benfey et al., 1989 EMBO J. 8:2195-2202) like those derived from plant viruses like the 35S CAMV (Franck et al., 1980 Cell 21:285-294), the 19S CaMV (see also U.S. Pat. No. 5,352,605 and PCT Application No. WO 8402913) or plant promoters like those from Rubisco small subunit described in U.S. Pat. No. 4,962,028.

Other preferred sequences for use in plant gene expression cassettes are targeting-sequences necessary to direct the gene product in its appropriate cell compartment (for review see Kermode, 1996 Crit. Rev. Plant Sci. 15(4):285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (for review see Gatz, 1997 Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992 Plant J. 2:397-404) and an ethanol inducible promoter (PCT Application No. WO 93/21334).

Also, suitable promoters responding to biotic or abiotic stress conditions are those such as the pathogen inducible PRP1-gene promoter (Ward et al., 1993 Plant. Mol. Biol. 22:361-366), the heat inducible hsp80-promoter from tomato (U.S. Pat. No. 5,187,267), cold inducible alpha-amylase promoter from potato (PCT Application No. WO 96/12814) or the wound-inducible pinII-promoter (European Patent No. 375091). For other examples of drought, cold, and salt-inducible promoters, such as the RD29A promoter, see Yamaguchi-Shinozalei et al. (1993 Mol. Gen. Genet. 236:331-340).

Especially preferred are those promoters that confer gene expression in specific tissues and organs, such as guard cells and the root hair cells. Suitable promoters include the napin-gene promoter from rapeseed (U.S. Pat. No. 5,608,152), the USP-promoter from *Vicia faba* (Baeumlein et al., 1991 Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980) or the legumin B4 promoter (LeB4; Baeumlein et al., 1992 Plant Journal, 2(2):233-9) as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, maize zein gene, oat glutelin gene, Sorghum kasirin-gene and rye secalin gene).

Also especially suited are promoters that confer plastid-specific gene expression since plastids are the compartment where lipid biosynthesis occurs. Suitable promoters are the viral RNA-polymerase promoter described in PCT Application No. WO 95/16783 and PCT Application No. WO 97/06250 and the clpP-promoter from *Arabidopsis* described in PCT Application No. WO 99/46394.

The invention further provides a recombinant expression vector comprising a STSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a STSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus wherein antisense nucleic acids are produced under the control of a high efficiency regulatory region. The activity of the regulatory region can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986 and Mol et al., 1990 FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a STSRP can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

Vector DNA can be introduced into prokaryotic or eukaryotic cells via conventional transformation or transfection techniques. As used herein, the terms "transformation", "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer and electroporation. Suitable methods for transforming or transfecting host cells including plant cells can be found in Sambrook, et al. (Molecular Cloning: A Laboratory Manual. $2^{nd}$, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses and forage crops, these crop plants are also preferred target plants for a genetic engineering as one further embodiment of the present invention.

In particular, the invention provides a method of producing a transgenic plant with a STSRP coding nucleic acid, wherein expression of the nucleic acid(s) in the plant results in increased tolerance to environmental stress as compared to a wild type variety of the plant comprising: (a) transforming a plant cell with an expression vector comprising a STSRP nucleic acid, and (b) generating from the plant cell a transgenic plant with a increased tolerance to environmental stress as compared to a wild type variety of the plant. The invention also provides a method of increasing expression of a gene of interest within a host cell as compared to a wild type variety of the host cell, wherein the gene of interest is transcribed in response to a STSRP, comprising: (a) transforming the host cell with an expression vector comprising a STSRP coding nucleic acid, and (b) expressing the STSRP within the host cell, thereby increasing the expression of the gene transcribed in response to the STSRP, as compared to a wild type variety of the host cell.

For such plant transformation, binary vectors such as pBinAR can be used (Höfgen and Willmitzer, 1990 Plant Science 66:221-230). Construction of the binary vectors can be performed by ligation of the cDNA in sense or antisense orientation into the T-DNA. 5-prime to the cDNA a plant promoter activates transcription of the cDNA. A polyadenylation sequence is located 3-prime to the cDNA. Tissue-specific expression can be achieved by using a tissue specific promoter. For example, seed-specific expression can be achieved by cloning the napin or LeB4 or USP promoter 5-prime to the cDNA. Also, any other seed specific promoter element can be used. For constitutive expression within the whole plant, the CaMV 35S promoter can be used. The expressed protein can be targeted to a cellular compartment using a signal peptide, for example for plastids, mitochondria or endoplasmic reticulum (Kermode, 1996 Crit. Rev. Plant Sci. 4 (15):285-423). The signal peptide is cloned 5-prime in frame to the cDNA to archive subcellular localization of the fusion protein. Additionally, promoters that are responsive to abiotic stresses can be used with, such as the *Arabidopsis* promoter RD29A, the nucleic acid sequences disclosed herein. One skilled in the art will recognize that the promoter used should be operatively linked to the nucleic acid such that the promoter causes transcription of the nucleic acid which results in the synthesis of an mRNA which encodes a polypeptide. Alternatively, the RNA can be an antisense RNA for use in affecting subsequent expression of the same or another gene or genes.

Alternate methods of transfection include the direct transfer of DNA into developing flowers via electroporation or *Agrobacterium* mediated gene transfer. *Agrobacterium* mediated plant transformation can be performed using for example the GV3101(pMP90) (Konez and Schell, 1986 Mol. Gen. Genet. 204:383-396) or LBA4404 (Clontech) *Agrobacterium tumefaciens* strain. Transformation can be performed by standard transformation and regeneration techniques (Deblaere et al., 1994 Nucl. Acids. Res. 13:4777-4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993.—360 S., ISBN 0-8493-5164-2). For example, rapeseed can be transformed via cotyledon or hypocotyl transformation (Moloney et al., 1989 Plant cell Report 8:238-242; De Block et al., 1989 Plant Physiol. 91:694-701). Use of antibiotica for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994 Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: N.Y. (1993) ISBN 3-540-97826-7). A specific example of maize transformation is found in U.S. Pat. No. 5,990,387 and a specific example of wheat transformation can be found in PCT Application No. WO 93/07256.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate or in plants that confer resistance towards a herbicide such as glyphosate or glufosinate. Nucleic acid molecules encoding a selectable marker can be introduced into a host cell on the same vector as that encoding a STSRP or can be introduced on a separate vector. Cells stably transfected with the introduced nucleic acid molecule can be identified by, for example, drug selection (e.g., cells that have incorporated the selectable marker gene will survive, while the other cells die).

To create a homologous recombinant microorganism, a vector is prepared which contains at least a portion of a STSRP gene into which a deletion, addition or substitution has been introduced to thereby alter, e.g., functionally disrupt, the STSRP gene. Preferably, the STSRP gene is a *Physcomitrella patens* STSRP gene, but it can be a homolog from a related plant or even from a mammalian, yeast, or insect source. In a preferred embodiment, the vector is designed such that, upon homologous recombination, the endogenous STSRP gene is functionally disrupted (i.e., no longer encodes a functional protein; also referred to as a knock-out vector). Alternatively, the vector can be designed such that, upon homologous recombination, the endogenous STSRP gene is mutated or otherwise altered but still encodes a functional protein (e.g., the upstream regulatory region can be altered to thereby alter the expression of the endogenous STSRP). To create a point mutation via homologous recombination, DNA-RNA hybrids can be used in a technique known as chimeraplasty (Cole-Strauss et al., 1999 Nucleic Acids Research 27(5):1323-1330 and Kmiec, 1999 Gene therapy American Scientist. 87(3):240-247). Homologous recombination procedures in *Physcomitrella patens* are also well known in the art and are contemplated for use herein.

Whereas in the homologous recombination vector, the altered portion of the STSRP gene is flanked at its 5' and 3' ends by an additional nucleic acid molecule of the STSRP gene to allow for homologous recombination to occur between the exogenous STSRP gene carried by the vector and an endogenous STSRP gene, in a microorganism or plant. The additional flanking STSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95 (8):4368-4373 for cDNA based recombination in *Physcomitrella patens*). The vector is introduced into a microorganism or plant cell (e.g., via polyethylene glycol mediated DNA), and cells in which the introduced STSRP gene has homologously recombined with the endogenous STSRP gene are selected using art-known techniques.

In another embodiment, recombinant microorganisms can be produced that contain selected systems which allow for regulated expression of the introduced gene. For example, inclusion of a STSRP gene on a vector placing it under control of the lac operon permits expression of the STSRP gene only in the presence of IPTG. Such regulatory systems are well known in the art.

A host cell of the invention, such as a prokaryotic or eukaryotic host cell in culture, can be used to produce (i.e., express) a STSRP. Accordingly, the invention further provides methods for producing STSRPs using the host cells of the invention. In one embodiment, the method comprises culturing the host cell of invention (into which a recombinant expression vector encoding a STSRP has been introduced, or into which genome has been introduced a gene encoding a wild-type or altered STSRP ) in a suitable medium until STSRP is produced. In another embodiment, the method further comprises isolating STSRPs from the medium or the host cell.

Another aspect of the invention pertains to isolated STSRPs, and biologically active portions thereof. An "isolated" or "purified" protein or biologically active portion thereof is free of some of the cellular material when produced by recombinant DNA techniques, or chemical precursors or other chemicals when chemically synthesized. The language "substantially free of cellular material" includes preparations of STSRP in which the protein is separated from some of the cellular components of the cells in which it is naturally or recombinantly produced. In one embodiment, the language "substantially free of cellular material" includes preparations of a STSRP having less than about 30% (by dry weight) of non-STSRP material (also referred to herein as a "contaminating protein"), more preferably less than about 20% of non-STSRP material, still more preferably less than about 10% of non-STSRP material, and most preferably less than about 5% non-STSRP material.

When the STSRP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of STSRP in which the protein is separated from chemical precursors or other chemicals that are involved in the synthesis of the protein. In one embodiment, the language "substantially free of chemical precursors or other chemicals" includes preparations of a STSRP having less than about 30% (by dry weight) of chemical precursors or non-STSRP chemicals, more preferably less than about 20% chemical precursors or non-STSRP chemicals, still more preferably less than about 10% chemical precursors or non-STSRP chemicals, and most preferably less than about 5% chemical precursors or non-STSRP chemicals. In preferred embodiments, isolated proteins, or biologically active portions thereof, lack contaminating proteins from the same organism from which the STSRP is derived. Typically, such proteins are produced by recombinant expression of, for example, a *Physcomitrella patens* STSRP in plants other than *Physcomitrella patens* or microorganisms such as *C. glutamicum*, ciliates, algae or fungi.

The nucleic acid molecules, proteins, protein homologs, fusion proteins, primers, vectors, and host cells described herein can be used in one or more of the following methods: identification of *Physcomitrella patens* and related organisms; mapping of genomes of organisms related to *Physcomitrella patens*; identification and localization of *Physcomi-*

*trella patens* sequences of interest; evolutionary studies; determination of STSRP regions required for function; modulation of a STSRP activity; modulation of the metabolism of one or more cell functions; modulation of the transmembrane transport of one or more compounds; and modulation of stress resistance.

The moss *Physcomitrella patens* represents one member of the mosses. It is related to other mosses such as *Ceratodon purpureus* which is capable of growth in the absence of light. Mosses like *Ceratodon* and *Physcomitrella* share a high degree of homology on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The STSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a STSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass and forage crops, for example.

In particular, the present invention describes using the expression of PLC-1, PLC-2, 14-3-3P-1, 14-3-3P-2 and CBP-1 of *Physcomitrella patens* to engineer drought-tolerant, salt-tolerant and/or cold-tolerant plants. This strategy has herein been demonstrated for *Arabidopsis thaliana*, Rapeseed/Canola, soybeans, corn and wheat but its application is not restricted to these plants. Accordingly, the invention provides a transgenic plant containing a STSRP selected from PLC-1 (SEQ ID NO:11); PLC-2 (SEQ ID NO:12); 14-3-3P-1 (SEQ ID NO:13); 14-3-3P-2 (SEQ ID NO:14) and CBP-1 (SEQ ID NO:15), wherein the environmental stress is drought, increased salt or decreased or increased temperature. In preferred embodiments, the environmental stress is drought or decreased temperature.

The present invention also provides methods of modifying stress tolerance of a plant comprising, modifying the expression of a STSRP in the plant. The invention provides that this method can be performed such that the stress tolerance is either increased or decreased. In particular, the present invention provides methods of producing a transgenic plant having an increased tolerance to environmental stress as compared to a wild type variety of the plant comprising increasing expression of a STSRP in a plant.

The methods of increasing expression of STSRPs can be used wherein the plant is either transgenic or not transgenic. In cases when the plant is transgenic, the plant can be transformed with a vector containing any of the above described STSRP coding nucleic acids, or the plant can be transformed with a promoter that directs expression of native STSRP in the plant, for example. The invention provides that such a promoter can be tissue specific. Furthermore, such a promoter can be developmentally regulated. Alternatively, non-transgenic plants can have native STSRP expression modified by inducing a native promoter.

The expression of PLC-1 (SEQ ID NO:1); PLC-2 (SEQ ID NO:12); 14-3-3P-1 (SEQ ID NO:13); 14-3-3P-2 (SEQ ID NO:14) or CBP-1 (SEQ ID NO:15) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657). The later case involves identification of the PLC-1 (SEQ ID NO:11); PLC-2 (SEQ ID NO:12); 14-3-3P-1 (SEQ ID NO:13); 14-3-3P-2 (SEQ ID NO:14) or CBP-1 (SEQ ID NO:15) homologs in the target plant as well as from its promoter. Zinc-finger-containing recombinant transcription factors are engineered to specifically interact with the PLC-1 (SEQ ID NO:11); PLC-2 (SEQ ID NO:12); 14-3-3P-1 (SEQ ID NO:13); 14-3-3P-2 (SEQ ID NO:14) or CBP-1 (SEQ ID NO:15) homolog and transcription of the corresponding gene is activated.

In addition to introducing the STSRP nucleic acid sequences into transgenic plants, these sequences can also be used to identify an organism as being *Physcomitrella patens* or a close relative thereof. Also, they may be used to identify the presence of *Physcomitrella patens* or a relative thereof in a mixed population of microorganisms. The invention provides the nucleic acid sequences of a number of *Physcomitrella patens* genes; by probing the extracted genomic DNA of a culture of a unique or mixed population of microorganisms under stringent conditions with a probe spanning a region of a *Physcomitrella patens* gene which is unique to this organism, one can ascertain whether this organism is present.

Further, the nucleic acid and protein molecules of the invention may serve as markers for specific regions of the genome. This has utility not only in the mapping of the genome, but also in functional studies of *Physcomitrella patens* proteins. For example, to identify the region of the genome to which a particular *Physcomitrella patens* DNA-binding protein binds, the *Physcomitrella patens* genome could be digested, and the fragments incubated with the DNA-binding protein. Those fragments that bind the protein may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related mosses.

The STSRP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein that are essential for the functioning of the enzyme. This type of determination is of value for protein engineering studies and may give an indication of what the protein can tolerate in terms of mutagenesis without losing function.

Manipulation of the STSRP nucleic acid molecules of the invention may result in the production of STSRPs having functional differences from the wild-type STSRPs. These proteins may be improved in efficiency or activity, may be present in greater numbers in the cell than is usual, or may be decreased in efficiency or activity.

There are a number of mechanisms by which the alteration of a STSRP of the invention may directly affect stress response and/or stress tolerance. In the case of plants expressing STSRPs, increased transport can lead to improved salt and/or solute partitioning within the plant tissue and organs. By either increasing the number or the activity of transporter molecules which export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim; Belter, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their tolerance to drought, salt, and temperature stress.

The engineering of one or more STSRP genes of the invention may also result in STSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226-235). While these products are typically excreted, cells can be genetically altered to transport more products than is typical for a wild-type cell. By optimizing the activity of one or more STSRPs of the invention which are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998 The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation see U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246-252.

The aforementioned mutagenesis strategies for STSRPs resulting in increased stress resistance are not meant to be limiting; variations on these strategies will be readily apparent to one skilled in the art. Using such strategies, and incorporating the mechanisms disclosed herein, the nucleic acid and protein molecules of the invention may be utilized to generate algae, ciliates, plants, fungi or other microorganisms like *C. glutamicum* expressing mutated STSRP nucleic acid and protein molecules such that the stress tolerance is improved.

The present invention also provides antibodies that specifically bind to a STSRP, or a portion thereof, as encoded by a nucleic acid described herein. Antibodies can be made by many well-known methods (See, e.g. *Harlow and Lane*, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163-167; Bebbington et al., 1992 Bio/Technology 10:169-175).

The phrases "selectively binds" and "specifically binds" with the polypeptide refer to a binding reaction that is determinative of the presence of the protein in a heterogeneous population of proteins and other biologics. Thus, under designated immunoassay conditions, the specified antibodies bound to a particular protein do not bind in a significant amount to other proteins present in the sample. Selective binding of an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See *Harlow and Lane* "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *Physcomitrella patens* (Hedw.) B.S.G. from the collection of the genetic studies section of the University of Hamburg were used. They originate from the strain 16/14 collected by H.L.K. Whitehouse in Gransden Wood, Huntingdonshire (England), which was subcultured from a spore by Engel (1968, Am. J. Bot. 55, 438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol $s^{-1}m^{-2}$ (white light; Philips TL 65W/25 fluorescent tube) and a light/dark change of 16/8 hours. The moss was either modified in liquid culture using Knop medium according to Reski and Abel (1985, Planta 165:354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of $H_2O$+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and Poly-(A)+ RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al. 1994, Mol. Gen. Genet., 244:352-359). The Poly(A)+ RNA was isolated using Dyna Beads® (Dynal, Oslo, Norway) following the instructions of the manufacturers protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (see Sambrook et al. 1989 Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'      SEQ ID NO:16

5'-CTAAAGGGAACAAAAGCTG-3'     SEQ ID NO:17

5'-TGTAAAACGACGGCCAGT-3'      SEQ ID NO:18
```

Sequences were processed and annotated using the software package EST-MAX commercially provided by Bio-Max (Munich, Germany). The program incorporates practically all bioinformatics methods important for functional and structural characterization of protein sequences. For reference the website at pedant.mips.biochem.mpg.de. The most important algorithms incorporated in EST-MAX are: FASTA: Very sensitive sequence database searches with estimates of statistical significance; Pearson W. R. (1990) Rapid and sensitive sequence comparison with FASTP and FASTA. Methods Enzymol. 183:63-98; BLAST: Very sensitive sequence database searches with estimates of statistical significance. Altschul S. F., Gish W., Miller W., Myers E. W., and Lipman D. J. Basic local alignment search tool. Journal of Molecular Biology 215:403-10; PREDATOR: High-accuracy secondary structure prediction from single and multiple sequences. Frishman, D. and Argos, P. (1997) 75% accuracy in protein secondary structure prediction. Proteins, 27:329-335; CLUSTALW: Multiple sequence alignment. Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680; TMAP: Transmembrane region prediction from multiply aligned sequences. Persson, B. and Argos, P. (1994) Prediction of transmembrane segments in proteins utilizing multiple sequence alignments. J. Mol. Biol. 237:182-192; ALOM2: Transmembrane region prediction from single sequences. Klein, P., Kanehisa, M., and DeLisi, C. Prediction of protein function from sequence properties: A discriminate analysis of a database. Biochim. Biophys. Acta 787:221-226 (1984). Version 2 by Dr. K. Nakai; PROSEARCH: Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919-921; BLIMPS: Similarity searches against a database of ungapped blocks. J. C. Wallace and Henikoff S., (1992); PATMAT: A searching and extraction program for sequence, pattern and block queries and databases, CABIOS 8:249-254. Written by Bill Alford.

Example 5

Identification of *Physcomitrella patens* ORFs Corresponding to PLC-1, PLC-2, 14-3-3P-1, 14-3-3P-2 and CBP-1

The *Physcomitrella patens* partial cDNAs (ESTs) shown in Table 1 below were identified in the *Physcomitrella patens* EST sequencing program using the program EST-MAX through BLAST analysis. The Sequence Identification Numbers corresponding to these ESTs are as follows: PLC-1 (SEQ ID NO:1); PLC-2 (SEQ ID NO:2); 14-3-3P-1 (SEQ ID NO:3); 14-3-3P-2 (SEQ ID NO:4) and CBP-1 (SEQ ID NO:5).

TABLE 1

| Name | Functional categories | Function | Sequence code | ORF position |
|---|---|---|---|---|
| PpPLC-1 | Signal transduction | phosphoinositide-specific phospholipase C | c_pp004040301r | 1–759 |
| PpPLC-2 | Signal transduction | phosphoinositide-specific phospholipase C | c_pp004041126r | 2–484 |
| Pp14-3-3P-1 | Signal transduction | 14-3-3 protein | c_pp002015016r | 1115–555 |
| Pp14-3-3-P-2 | Signal transduction | 14-3-3 brain protein homolog | s_pp001097008r | 479–216 |
| CBP-1 | Signal transduction | EF-Hand containing protein-like | c_pp004076327r | 1–566 |

TABLE 2

Degree of amino acid identity and similarity of PpPLC-1 and other homologous proteins (Pairwise comparison program was used: gap penalty: 10; gap extension penalty: 0.1; score matrix: blosum62)

| | Swiss-Prot # | | | | |
|---|---|---|---|---|---|
| | Q43442 | P93341 | Q43439 | O49902 | Q43443 |
| Protein name | PHOSPHOINOSITIDE-SPECIFIC PHOSPHOLIPASE C P12 | PHOSPHOINOSITIDE-SPECIFIC PHOSPHOLIPASE C | PHOSPHATIDYLINOSITOL-SPECIFIC PHOSPHOLIPASE C | 1-PHOSPHATIDYLINOSITOL-4,5-BISPHOSPHATE PHOSPHODIESTERASE | PHOSPHOINOSITIDE-SPECIFIC PHOSPHOLIPASE C P13 |

TABLE 2-continued

Degree of amino acid identity and similarity of PpPLC-1 and other homologous proteins (Pairwise comparison program was used: gap penalty: 10; gap extension penalty: 0.1; score matrix: blosum62)

| | Swiss-Prot # | | | | |
|---|---|---|---|---|---|
| | Q43442 | P93341 | Q43439 | O49902 | Q43443 |
| Species | Glycine max (Soybean) | Nicotiana rustica (Aztec tobacco) | Glycine max (Soybean) | Nicotiana rustica (Aztec tobacco) | Glycine max (Soybean) |
| Identity % | 46% | 43% | 43% | 43% | 43% |
| Similarity % | 57% | 54% | 53% | 53% | 53% |

TABLE 3

Degree of amino acid identity and similarity of PpPLC-2 and other homologous proteins (Pairwise comparison program was used: gap penalty: 10; gap extension penalty: 0.1; score matrix: blosum62)

| | Swiss-Prot # | | | | |
|---|---|---|---|---|---|
| | Q43442 | O49902 | Q43443 | P93341 | Q43439 |
| Protein name | PHOSPHO-INOSITIDE-SPECIFIC PHOSPHO-LIPASE C P12 | 1-PHOSPHATIDYLINOSITOL-4,5-BISPHOSPHATE PHOSPHODIESTERASE | PHOSPHOINOSITIDE-SPECIFIC PHOSPHOLIPASE C P13 | PHOSPHOINOSITIDE-SPECIFIC PHOSPHOLIPASE C | PHOSPHATIDYLINOSITOL-SPECIFIC PHOSPHOLIPASE C |
| Species | Glycine max (Soybean) | Nicotiana rustica (Aztec tobacco) | Glycine max (Soybean) | Nicotiana rustica (Aztec tobacco) | Glycine max (Soybean) |
| Identity % | 44% | 41% | 42% | 40% | 42% |
| Similarity % | 54% | 53% | 53% | 52% | 53% |

TABLE 4

Degree of amino acid identity and similarity of Pp14-3-3P-1 and other homologous proteins (Pairwise comparison program was used: gap penalty: 10; gap extension penalty: 0.1; score matrix: blosum62)

| | Swiss-Prot # | | | | |
|---|---|---|---|---|---|
| | Q9LKK9 | Q9M5W3 | Q96453 | O49152 | P42654 |
| Protein name | 14-3-3 PROTEIN | 14-3-3-LIKE PROTEIN | 14-3-3-LIKE PROTEIN D | 14-3-3 PROTEIN HOMOLOG | 14-3-3-LIKE PROTEIN B |
| Species | Populus alba x Populus tremula | Euphorbia esula (Leafy spurge) | Glycine max (Soybean) | Maackia amurensis | Vicia faba (Broad bean) |
| Identity % | 80% | 80% | 78% | 78% | 77% |
| Similarity % | 90% | 88% | 87% | 88% | 88% |

TABLE 5

Degree of amino acid identity and similarity of Pp14-3-3P-2 and other homologous proteins (Pairwise comparison program was used: gap penalty: 10; gap extension penalty: 0.1; score matrix: blosum62)

| | Swiss-Prot # | | | | |
|---|---|---|---|---|---|
| | Q9SP07 | P93785 | O24222 | O49082 | Q9XEW8 |
| Protein name | 14-3-3-LIKE PROTEIN | 14-3-3 PROTEIN | GF14-C PROTEIN | GF14 PROTEIN | 14-3-3 PROTEIN |
| Species | Lilium longiflorum (Trumpet lily) | Solanum tuberosum (Potato) | Oryza sativa (Rice) | Fritillaria agrestis | Picea glauca (White spruce) |
| Identity % | 79% | 80% | 80% | 79% | 80% |
| Similarity % | 86% | 87% | 88% | 87% | 88% |

TABLE 6

Degree of amino acid identity and similarity of PpCBP-1 and other homologous proteins (Pairwise comparison program was used: gap penalty: 10; gap extension penalty: 0.1; score matrix: blosum62)

| | Swiss-Prot # | | | | |
|---|---|---|---|---|---|
| | Q9T0I9 | O82062 | O64866 | Q42438 | Q9SQI4 |
| Protein name | EF-HAND CONTAINING PROTEIN-LIKE | 39 KDA EF-HAND CONTAINING PROTEIN | F4I1.12 PROTEIN | CALCIUM-DEPENDENT PROTEIN KINASE | CENTRIN |
| Species | Arabidopsis thaliana (Mouse-ear cress) | Solanum tuberosum (Potato) | Arabidopsis thaliana (Mouse-ear cress) | Arabidopsis thaliana (Mouse-ear cress) | Nicotiana tabacum (Common tobacco) |
| Identity % | 19% | 20% | 24% | 10% | 16% |
| Similarity % | 34% | 35% | 41% | 21% | 28% |

Example 6

Cloning of the Full-Length Physcomitrella patens cDNA Encoding for PLC-1, PLC-2, 14-3-3P-1, 14-3-3P-2 and CBP-1

To isolate the clones encoding PLC-1, PLC-2, 14-3-3P-2 and CBP-1 from *Physcomitrella patens*, cDNA libraries were created with SMART RACE cDNA Amplification kit (Clontech Laboratories) following manufacturer's instructions. Total RNA isolated as described in Example 3 was used as the template. The cultures were treated prior to RNA isolation as follows: Salt Stress: 2, 6, 12, 24, 48 hours with 1-M NaCl-supplemented medium; Cold Stress: 4° C. for the same time points as for salt; Drought Stress: cultures were incubated on dry filter paper for the same time points as for salt.

5' RACE Protocol

The EST sequences PLC-1 (SEQ ID NO:1), PLC-2 (SEQ ID NO:2), 14-3-3P-2 (SEQ ID NO:4) and CBP-1 (SEQ ID NO:5) identified from the database search as described in Example 5 were used to design oligos for RACE (see Table 7). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions. The sequences obtained from the RACE reactions corresponded to full-length coding regions of PLC-1, PLC-2, 14-3-3P-2 and CBP-1 were used to design oligos for full-length cloning of the respective genes (see below full-length amplification).

Full-Length Amplification

Full-length clones corresponding PLC-1 (SEQ ID NO:1); PLC-2 (SEQ ID NO:2); 14-3-3P-1 (SEQ ID NO:3); 14-3-3P-2 (SEQ ID NO:4) and CBP-1 (SEQ ID NO:5) were obtained by performing polymerase chain reaction (PCR) with gene-specific primers (see Table 7) and the original EST as the template. The conditions for the reaction were standard conditions with PWO DNA polymerase (Roche). PCR was performed according to standard conditions and to manufacturer's protocols (Sambrook et al., 1989 Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C. followed by five cycles of one minute at 94° C., one minute at 50° C. and 1.5 minutes at 72° C. This was followed by twenty five cycles of one minute at 94° C., one minute at 65° C. and 1.5 minutes at 72° C.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al. 1989. Molecular Cloning, A Laboratory Manual. 2nd Edition. Cold Spring Harbor Laboratory Press. Cold Spring Harbor, N.Y.). Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989 Molecular Cloning, A Laboratory Manual. 2nd Edition. Cold Spring Harbor Laboratory Press. Cold Spring Harbor, N.Y.).

TABLE 7

| Gene | Sites in the final product | Isolation Method | Primers Race | Primer Full-length PCR |
|---|---|---|---|---|
| PpPLC-1 | XmaI/HpaI | 5' RACE and RT-PCR for Full-length clone | RC204: (SEQ ID NO:19) CAGGTCCGAG CTGACGATGA ACCCAG | RC642: (SEQ ID NO:20) ATCCCGGGCAATCGTCG GGTGACATTCCTGTTC RC643: |

TABLE 7-continued

| Gene | Sites in the final product | Isolation Method | Primers Race | Primer Full-length PCR |
|---|---|---|---|---|
| | | | | (SEQ ID NO:21) AGCGTTCCACATGCAT |
| PpPLC-2 | XmaI/HpaI | 5' RACE and RT-PCR for Full-length clone | RC203: (SEQ ID NO:22) CGAGCTCCTCC ACCAGATTCCT GTTC | RC608: (SEQ ID NO:23) ATCCCGGGCTTCGGGA GTTTAAGAGGATGTCAC G RC609: (SEQ ID NO:24) GCGTTAACCTTGGGTGC ACACACTAAACTGGTC |
| Pp14-3-3P-1 | XmaI/SacI | RT-PCR for Full-length clone | | RC399: (SEQ ID NO:25) ATCCCGGGCGGACTGTC GTGGACGAGTGTGCTA G RC400: (SEQ ID NO:26) GCGAGCTCGGCACGCA ACTGCACATCTTCTTGC |
| Pp14-3-3P-2 | HpaI/SacI | 5' RACE and RT-PCR for Full-length clone | RC195: (SEQ ID NO:27) ACCAGCCTCA ACTTAGTCGCC TGGAC | RC548: (SEQ ID NO:28) GCGTTAACTTCACAATG ACGGAGCTACGAGAGG A RC549: (SEQ ID NO:29) GCGAGCTCCAGCCTCA ACTTAGTCGCCTGGACA |
| PpCBP-1 | XmaI/SacI | 5' RACE and RT-PCR for Full-length clone | RC197: (SEQ ID NO:30) CCCTGCTCAAC GCCCAGCTGC ATAAT | RC654: (SEQJDNO:31) ATCCCGGGTCAGCTCGT GGAAGTGTTGCAGCA RC655: (SEQ ID NO:32) GCGAGCTCGTCCAATTT TCACTCGGGGCTTCC |

Example 7

Engineering Stress-Tolerant *Arabidopsis* Plants by Over-Expressing the Genes PLC-1, PLC-2, 14-3-3P-1, 14-3-3P-2 and CBP-1

Binary Vector Construction: pACGH101

The plasmid construct pACGH101 was digested with PstI (Roche) and FseI (NEB) according to manufacturers' instructions. The fragment was purified by agarose gel and extracted via the Qiaex II DNA Extraction kit (Qiagen). This resulted in a vector fragment with the *Arabidopsis* Actin2 promoter with internal intron and the OCS3 terminator. Primers for PCR amplification of the NPTII gene were designed as follows:

5'NPT-Pst:
(SEQ ID NO:33)
GCG-CTG-CAG-ATT-TCA-TTT-GGA-GAG-GAC-ACG

3'NPT-Fse:
(SEQ ID NO:34)
CGC-GGC-CGG-CCT-CAG-AAG-AAC-TCG-TCA-AGA-AGG-CG.

The 0.9 kilobase NPTII gene was amplified via PCR from pCambia 2301 plasmid DNA [94° C. 60 sec, {94° C. 60 sec, 61° C. (−0.1° C. per cycle) 60 sec, 72° C. 2 min}×25 cycles, 72° C. 10 min on Biometra T-Gradient machine], and purified via the Qiaquick PCR Extraction kit (Qiagen) as per manufacturer's instructions. The PCR DNA was then subcloned into the pCR-BluntII TOPO vector (Invitrogen) pursuant to the manufacturer's instructions (NPT-Topo construct). These ligations were transformed into Top10 cells (Invitrogen) and grown on LB plates with 50 ug/ml kanamycin sulfate overnight at 37° C. Colonies were then used to inoculate 2 ml LB media with 50 ug/ml kanamycin sulfate and grown overnight at 37° C. Plasmid DNA was recovered using the Qiaprep Spin Miniprep kit (Qiagen) and sequenced in both the 5' and 3' directions using standard conditions. Subsequent analysis of the sequence data using VectorNTI software revealed no PCR errors present in the NPTII gene sequence.

The NPT-Topo construct was then digested with PstI (Roche) and FseI (NEB) according to manufacturers' instructions. The 0.9 kilobase fragment was purified on agarose gel and extracted by Qiaex II DNA Extraction kit (Qiagen). The Pst/Fse insert fragment from NPT-Topo and the Pst/Fse vector fragment from pACGH101 were then ligated together using T4 DNA Ligase (Roche) following manufacturer's instructions. The ligation was then transformed into Top10 cells (Invitrogen) under standard conditions, creating pBPSsc019 construct. Colonies were selected on LB plates with 50 ug/ml kanamycin sulfate and grown overnight at 37° C. These colonies were then used to inoculate 2 ml LB media with 50 ug/ml overnight at 37° C. These colonies were then used to inoculate 2 ml LB media with 50 ug/ml kanamycin sulfate and grown overnight at 37° C. Plasmid DNA was recovered using the Qiaprep Spin Miniprep kit (Qiagen) following the manufacturer's instructions.

The pBPSSC019 construct was digested with KpnI and BsaI (Roche) according to manufacturer's instructions. The fragment was purified via agarose gel and then extracted via the Qiaex II DNA Extraction kit (Qiagen) as per its instructions, resulting in a 3 kilobase Act-NPT cassette, which included the *Arabidopsis* Actin2 promoter with internal intron, the NPTII gene and the OCS3 terminator.

The pBPSJH001 vector was digested with SpeI and ApaI (Roche) and blunt-end filled with Klenow enzyme and 0.1 mM dNTPs (Roche) according to manufacture's instructions. This produced a 10.1 kilobase vector fragment minus the Gentamycin cassette, which was recircularized by self-ligating with T4 DNA Ligase (Roche), and transformed into Top10 cells (Invitrogen) via standard conditions. Transformed cells were selected for on LB agar containing 50 μg/ml kanamycin sulfate and grown overnight at 37° C. Colonies were then used to inoculate 2 ml of liquid LB containing 50 μg/ml kanamycin sulfate and grown overnight at 37° C. Plasmid DNA was extracted using the QIAprep Spin Miniprep Kit (Qiagen) following manufacture's instructions. The recircularized plasmid was then digested with KpnI (Roche) and extracted from agarose gel via the Qiaex II DNA Extraction kit (Qiagen) as per manufacturers' instructions.

The Act-NPT Kpn-cut insert and the Kpn-cut pBPSJH001 recircularized vector were then ligated together using T4 DNA Ligase (Roche) and transformed into Top10 cells (Invitrogen) as per manufacturers' instructions. The resulting construct, pBPSsc022, now contained the Super Promoter, the GUS gene, the NOS terminator, and the Act-NPT cassette. Transformed cells were selected for on LB agar containing 50 μg/ml kanamycin sulfate and grown overnight at 37° C. Colonies were then used to inoculate 2 ml of liquid LB containing 50 μg/ml kanamycin sulfate and grown overnight at 37° C. Plasmid DNA was extracted using the QIAprep Spin Miniprep Kit (Qiagen) following manufacturer's instructions. After confirmation of ligation success via restriction digests, pBPSsc022 plasmid DNA was further propigated and recovered using the Plasmid Midiprep Kit (Qiagen) following the manufacturer's instructions.

Subcloning of PLC-1, PLC-2, 14-3-3P-1, 14-3-3P-2 and CBP-1 Into the Binary Vector The fragments containing the different *Physcomitrella patens* signal transduction factors were subcloned from the recombinant PCR2.1 TOPO vectors by double digestion with restriction enzymes (see Table 8) according to manufacturer's instructions. The subsequence fragment was excised from agarose gel with a QIAquick Gel Extraction Kit (QIAgen) according to manufacturer's instructions and ligated into the binary vector pBPSsc022, cleaved with appropriate enzymes (see Table 8) and dephosphorylated prior to ligation. The resulting recombinant pBPSsc022 vector contained the corresponding transcription factor in the sense orientation under the control of the constitutive super promoter.

TABLE 8

Listed are the names of the various constructs of the *Physcomitrella patens* transcription factors used for plant transformation

| Gene | Enzymes used to generate gene fragment | Enzymes used to restrict pBPSJH001 | Binary Vector Construct |
| --- | --- | --- | --- |
| PpPLC-1 | XmaI/HpaI | XmaI/Ecl136 | pBPSSY009 |
| PpPLC-2 | XmaI/HpaI | XmaI/Ecl136 | pBPSJYW009 |
| Pp14-3-3P-1 | XmaI/SacI | SmaI/SacI | pBPSJYW018 |
| Pp14-3-3P-2 | HpaI/SacI | SmaI/SacI | pBPSSY031 |
| PpCBP-1 | XmaI/SacI | XmaI/SacI | PBPSLVM182 |

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold 1993, Acad. Sci. Paris. 316:1194-1199; Bent et al. 1994, Science 265:1856-1860).

Screening of Transformed Plants

T1 seeds were sterilized according to standard protocols (Xiong et al. 1999, Plant Molecular Biology Reporter 17: 159-170). Seeds were plated on ½ Murashige and Skoog media (MS) (Sigma-Aldrich) pH 5.7 with KOH, 0.6% agar and supplemented with 1% sucrose, 0.5 g/L 2-[N-Morpholino]ethansulfonic acid (MES) (Sigma-Aldrich), 50 μg/ml kanamycin (Sigma-Aldrich), 500 μg/ml carbenicillan (Sigma-Aldrich) and 2 μg/ml benomyl (Sigma-Aldrich). Seeds on plates were vernalized for four days at 4° C. The seeds were germinated in a climatic chamber at an air temperature of 22° C. and light intensity of 40 micromol $s^{-1}m^{-2}$ (white light; Philips TL 65W/25 fluorescent tube) and 16 hours light and 8 hours dark day length cycle. Transformed seedlings were selected after 14 days and transferred to ½ MS media pH 5.7 with KOH 0.6% agar plates supplemented with 0.6% agar, 1% sucrose, 0.5 gAL MES (Sigma-Aldrich), and 2 μg/ml benomyl (Sigma-Aldrich) and allowed to recover for five-seven days.

Drought Tolerance Screening

T1 seedlings were transferred to dry, sterile filter paper in a petri dish and allowed to desiccate for two hours at 80% RH (relative humidity) in a Percieval Growth Cabinet MLR-350H, micromole $s^{-1}m^{-2}$ (white light; Philips TL 65W/25 fluorescent tube). The RH was then decreased to 60% and the seedlings were desiccated further for eight hours. Seedlings were then removed and placed on ½ MS 0.6% agar plates supplemented with 2 μg/ml benomyl (Sigma-Aldrich) and 0.5 g/L MES (Sigma-Aldrich) and scored after five days.

Under drought stress conditions, PpPLC-1 over-expressing *Arabidopsis thaliana* plants showed a 70% (7 survivors from 10 stressed plants) survival rate to the stress screening; PpPLC-2, 98% (50 survivors from 51 stressed plants); Pp14-3-3P-1, 80% (12 survivors from 15 stressed plants); Pp14-3-3P-2, 100% (22 survivors from 22 stressed plants); and PpCBP-1, 100% (52 survivors from 52 stressed plants), whereas the untransformed control only showed a 28% survival rate. It is noteworthy that the analyses of these transgenic lines were performed with T1 plants, and therefore, the results will be better when a homozygous, strong expresser is found.

TABLE 9

Summary of the drought stress tests

| Gene Name | Drought Stress Test | | |
|---|---|---|---|
| | Number of survivors | Total number of plants | Percentage of survivors |
| PpPLC-1 | 7 | 10 | 70% |
| PpPLC-2 | 50 | 51 | 98% |
| Pp14-3-3P-1 | 12 | 15 | 80% |
| Pp14-3-3P-2 | 22 | 22 | 100% |
| PpCBP-1 | 52 | 52 | 100% |
| Control | 16 | 57 | 28% |

Freezing Tolerance Screening

Seedlings were moved to petri dishes containing ½ MS 0.6% agar supplemented with 2% sucrose and 2 μg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C. decreasing 1° C./hour. The seedlings were then incubated at −5.0° C. for 24 hours and then allowed to thaw at 5° C. for 12 hours. The water was poured off and the seedlings were scored after 5 days.

Under freezing stress conditions, PpPLC-2 over-expressing *Arabidopsis thaliana* plants showed a 78% (18 survivors from 23 stressed plants) survival rate; Pp14-3-3P-1, 100% (6 survivor from 6 stressed plants) and PpCBP-1, 78% (18 survivor from 23 stressed plants), whereas the untransformed control only showed a 2% (1 survivors from 48 tested plants) survival rate. It is noteworthy that the analyses of these transgenic lines were performed with T1 plants, and therefore, the results will be better when a homozygous, strong expresser is found.

TABLE 10

Summary of the freezing stress tests

| Gene Name | Freezing Stress Test | | |
|---|---|---|---|
| | Number of survivors | Total number of plants | Percentage of survivors |
| PpPLC-2 | 18 | 23 | 78% |
| Pp14-3-3P-1 | 6 | 6 | 100% |
| PpCBP-1 | 25 | 37 | 68% |
| Control | 1 | 48 | 2% |

Salt Tolerance Screening

Seedlings were transferred to filter paper soaked in ½ MS and placed on ½ MS 0.6% agar supplemented with 2 μg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 μg/ml benomyl. The seedlings were scored after 5 days.

The transgenic plants are screened for their improved salt tolerance demonstrating that transgene expression confers salt tolerance.

Example 8

Detection of the PLC-1, PLC-2, 14-3-3P-1, 14-3-3P-2 and CBP-1 Transgenes in the Transgenic *Arabidopsis* Lines To check for the presence of the PpPLC-1, PpPLC-2, Pp14-3-3P-1, Pp14-3-3P-2 and PpCBP-1 transgenes in transgenic *Arabidopsis* lines, PCR was performed on genomic DNA which contaminates the RNA samples taken as described in Example 9 below. 2.5 μl of RNA sample was used in a 50 μl PCR reaction using Taq DNA polymerase (Roche Molecular Biochemicals) according to the manufacturer's instructions. The primer for the binary vector region (5'GCTGACACGC-CAAGCCTCGCTAGTC3') (SEQ ID NO:35) and the gene specific 3' primer for each transgene which was used for the full-length RT-PCR (see Table 7) were used for the PCR. The PCR program was as following: 30 cycles of 1 minute at 94° C., 1 minute at 62° C. and 4 minutes at 70° C., followed by 10 minutes at 72° C. Binary vector plasmid with the transgenes cloned in was used as positive control, and the wild type C24 genomic DNA was used as negative control in the PCR reactions. 10 μl PCR reaction was analyzed on 0.8% agarose—ethidium bromide gel.

The transgenes with the expected size (for PpPLC-1: 2.3 kb fragment; PpPLC-2: 2.2 kb fragment; Pp14-3-3P-1: 0.9 kb fragment; Pp14-3-3P-2: 0.9 kb fragment; PpCBP-1: 1.8 kb fragment) were successfully amplified from the T1 transgenic lines and positive control, but not from the wild-type C24. This result indicates that the T1 transgenic plants contain at least one copy of the transgenes. There was no indication of existence of either identical or very similar in untransformed Arabidopsis thaliana which can be amplified in this method in the wild-type plants.

Example 9

Detection of the PLC-1, PLC-2, 14-3-3P-1, 14-3-3P-2 and CBP-1 Transgene mRNA in Transgenic *Arabidopsis* Lines Transgene expression was detected using RT-PCR. Total RNA was isolated from stress-treated plants using a procedure adapted from (Verwoerd et al., 1989 NAR 17:2362). Leaf samples (50-100 mg) were collected and ground to a fine powder in liquid nitrogen. Ground tissue was resuspended in 500 μl of a 80° C., 1:1 mixture, of phenol to extraction buffer (100 mM LiCl, 100 mM Tris pH8, 10 mM EDTA, 1% SDS), followed by brief vortexing to mix. After the addition of 250 μl of chloroform, each sample was vortexed briefly. Samples were then centrifuged for 5 minutes at 12,000×g. The upper aqueous phase was removed to a fresh eppendorf tube. RNA was precipitated by adding $\frac{1}{10}^{th}$ volume 3M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 μl DEPC treated water. To remove contaminating DNA from the samples, each was treated with RNase-free DNase (Roche) according to the manufacturer's recommendations. cDNA was synthesized from total RNA using the $1^{st}$ Strand cDNA synthesis kit (Boehringer Mannheim) following manufacturer's recommendations.

PCR amplification of a gene-specific fragment from the synthesized cDNA was performed using Taq DNA polymerase (Roche) and gene-specific primers as shown below in the following reaction: 1× PCR buffer, 1.5 mM MgCl$_2$, 0.2 μM each primer, 0.2 μM dNTPs, 1 unit polymerase, 5 μl cDNA from synthesis reaction. Amplification was performed under the following conditions: Predenaturation, 94° C., 3 minutes; denaturation, 94° C., 30 seconds; annealing, 62° C., 30 seconds; extension, 72° C., 2 minute, 30 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. These results indicated that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 7.

half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 μM acetosyringone. Bacteria cultures are incubated in this pre-induction medium for 2 hours at room temperature before use. The axis of soybean zygotic seed embryos at approximately 15% moisture content are imbibed for 2 hours at room temperature with the pre-induced *Agrobacterium* suspension culture. The embryos are removed from the imbibition culture and are transferred to Petri dishes containing solid MS medium supplemented with 2% sucrose and incubated for 2 days, in the dark at room temperature. Alternatively, the embryos are placed on top of moistened

TABLE 11

Primers used for the amplification of respective transgene mRNA in PCR using RNA isolated from transgenic *Arabidopsis thaliana* plants as template

| Gene | 5' primer | 3' primer |
| --- | --- | --- |
| PpPLC-1 | 5'CCAGCTTAGCAGCGAC AGTAGCGACGT3' (SEQ ID NO:36) | 5'CAGTCTGTCTTCCACGGTAG TTCCT3' (SEQ ID NO:37) |
| PpPLC-2 | 5'GGCCATGGAGAACAGG AATCTGGTGG3' (SEQ ID NO:38) | 5'GCTCCGTAGTTCCAAGCCAG AGTAG3' (SEQ ID NO:39) |
| Pp14-3-3P-1 | Same primers used for the full length RT-PCR (see Table 1) | Same primers used for the full length RT-PCR (see Table 1) |
| Pp14-3-3P-2 | Same primers used for the full length RT-PCR (see Table 1) | Same primers used for the full length RT-PCR (see Table 1) |
| PpCBP-1 | 5'GACACTGATGAGAGTG GCAAGCTGAG3' (SEQ ID NO:40) | 5'GACTCGATGCTTCAACGAGA GGCAG3' (SEQ ID NO:41) |

Example 10

Engineering Stress-Tolerant Soybean Plants by Over-Expressing the PLC-1, PLC-2, 14-3-3P-1, 14-3-3P-2 and CBP-1 Gene The constructs pBPSSY009, pBPSJYW009, pBPSJYW018, pBPSSY031 and pBPSLVM182 are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated during 4 weeks at 25° C., under 150 μmol m$^{-2}$sec$^{-1}$ and 12 hours photoperiod. Once the seedlings produce roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 μmol m$^{-2}$sec$^{-1}$ light intensity and 12 hours photoperiod for about 80 days.

The transgenic plants are then screened for their improved drought, salt and/or cold tolerance according to the screening method described in Example 7 to demonstrate that transgene expression confers stress tolerance.

Example 11

Engineering Stress-Tolerant Rapeseed/Canola Plants by Over-Expressing the PLC-1, PLC-2, 14-3-3P-1, 14-3-3P-2 and CBP-1 Genes The constructs pBPSSY009, pBPSJYW009, pBPSJYW018, pBPSSY031 and pBPSLVM182 are used to transform rapeseed/canola as described below.

The method of plant transformation described herein is also applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period, the seeds lose approx. 85% of its water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved stress tolerance according to the screening method described in Example 7 to demonstrate that transgene expression confers drought tolerance.

Example 12

Engineering Stress-Tolerant Corn Plants by Over-Expressing the PLC-1, PLC-2, 14-3-3P-1, 14-3-3P-2 or CBP-1 Genes The constructs pBPSSY009, pBPSJYW009, pBPSJYW018, pBPSSY031 and pBPSLVM182 are used to transform corn as described below.

Transformation of maize (*Zea Mays* L.) is performed with the method described by Ishida et al. 1996. Nature Biotech 14745-50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are then screened for their improved drought, salt and/or cold tolerance according to the screening method described in Example 7 to demonstrate that transgene expression confers stress tolerance.

Example 13

Engineering Stress-Tolerant Wheat Plants by Over-Expressing the PLC-1, PLC-2, 14-3-3P-1, 14-3-3P-2 and CBP-1 Genes The constructs pBPSSY009, pBPSJYW009, pBPSJYW018, pBPSSY031 and pBPSLVM182 are used to transform wheat as described below.

Transformation of wheat is performed with the method described by Ishida et al. 1996 Nature Biotech. 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7 demonstrating that transgene expression confers drought tolerance.

Example 14

Identification of Homologous and Heterologous Genes

Gene sequences can be used to identify homologous or heterologous genes from cDNA or genomic libraries. Homologous genes (e. g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by e. g. UV cross linking. Hybridization is carried out at high stringency conditions. In aqueous solution hybridization and washing is performed at an ionic strength of 1 M NaCl and a temperature of 68° C. Hybridization probes are generated by e. g. radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10-20 amino acids) can be carried out by using synthetic radio labeled oligonucleotide probes. Radio labeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide hybridization solution:

6×SSC 0.01 M sodium phosphate 1 mM EDTA (pH 8)

0.5% SDS

100 μg/ml denatured salmon sperm DNA 0.1% nonfat dried milk

During hybridization, temperature is lowered stepwise to 5-10° C. below the estimated oligonucleotide Tm or down to room temperature followed by washing steps and autoradiography. Washing is performed with low stringency such as 3 washing steps using 4×SSC. Further details are described by Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons.

Example 15

Identification of Homologous Genes by Screening Expression Libraries with Antibodies cDNA clones can be used to produce recombinant protein for example in E. coli (e. g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994 BioTechniques 17:257-262. The antibody can than be used to screen expression cDNA libraries to identify homologous or heterologous genes via an immunological screening (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons).

Example 16

In Vivo Mutagenesis

In vivo mutagenesis of microorganisms can be performed by passage of plasmid (or other vector) DNA through E. coli or other microorganisms (e.g. Bacillus spp. or yeasts such as Saccharomyces cerevisiae) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: Escherichia coli and Salmonella, p. 2277-2294, ASM: Washington.) Such strains are well known to those skilled in the art. The use of such strains is illustrated, for example, in Greener, A. and Callahan, M. (1994) Strategies 7: 32-34. Transfer of mutated DNA molecules into plants is preferably done after selection and testing in microorganisms. Transgenic plants are generated according to various examples within the exemplification of this document.

Example 17

In Vitro Analysis of the Function of Physcomitrella Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N.C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkine-tik, $2^{nd}$ ed. VCH: Weinheim (ISBN 3527300325); Bergmeyer, H. U., Bergmeyer, J., Graβl, M., eds. (1983-1986) Methods of Enzymatic Analysis, $3^{rd}$ ed., vol. I-XII, Verlag Chemie: Weinheim; and Ullmann's Encyclopedia of Industrial Chemistry (1987) vol. A9, Enzymes. VCH: Weinheim, p. 352-363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) EMBO J. 14: 3895-3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B. Pores, Channels and Transporters, in Biomembranes, Molecular Structure and Function, pp. 85-137, 199-234 and 270-322, Springer: Heidelberg (1989).

Example 18

Purification of the Desired Product from Transformed Organisms

Recovery of the desired product from plant material (i.e., Physcomitrella patents or Arabidopsis thaliana), fungi, algae, ciliates, C. glutamicum cells, or other bacterial cells transformed with the nucleic acid sequences described herein, or the supernatant of the above-described cultures can be performed by various methods well known in the art. If the desired product is not secreted from the cells, can be harvested from the culture by low-speed centrifugation, the cells can be lysed by standard techniques, such as mechanical force or sonification. Organs of plants can be separated mechanically from other tissue or organs. Following homogenization cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986). Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994 *Appl. Environ. Microbiol.* 60:133-140; Malaldhova et al., 1996 *Biotekhnologiya* 11:27-32; and Schmidt et al., 1998 *Bioprocess Engineer.* 19:67-70. Ulmann's Encyclopedia of Industrial Chemistry, (1996) vol. A27, VCH: Weinheim, p. 89-90, p. 521-540, p. 540-547, p. 559-566, 575-581 and p. 581-587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

```
Nucleotide sequence of the partial PLC-1 from
Physcomitrella patens
                                        (SEQ ID NO:1)
GCACGAGTCCAAGAAGGGGGATTTGGCGCAGGATCTATTGGGGGATGTGT
TCTCGACTTACAGCGAGAATGGGAAGCTGGACGCCGAGGGGTTGCTGAAG
TTCTTGCAGACAGAGCAAGGGGATAGCAAGTCCTCTCTAGATGACGCCAA
GCACCTAGTGGAGTTGATTCGGAATGAGAGACATAAGTCGAAATTCCCTG
GGTTCATCGTCAGCTCGGACCTGTCGAAGGGTGATTTTAAAAACTATGTA
CTGAGCCCGGATTTGAATGGGGTTCTTGAAAGCACTGTGCATCAAGACAT
GACGCAGCCGTTATCGCACTACTTCATATTCACTGGTCACAACTCGTACT
TGACGGGTAACCAGCTTAGCAGCGACAGTAGCGACGTTCCCATTGCTGCT
GCACTGCAACGTGGCGTGCGGGTGGTGGAACTGGATTTGTGGCCTGACGA
TAAAGGCGGCATCAAGGTCACTCACGGGAACACACTCACCAGTCCAGTTG
CTTTCGAGAAGTGCATAAAAGCCATCAAGGCCAACGCGTTCGTCTCCTCG
AAATATCCTGTAGTTATCACTCTTGAGGATCATCTTTCAAGTCCTTTACA
GGCCCTTGCTGCAGAGACTTTGACGAACATTTTGGGAGAGGACTTGTACT
ATCCACCCTCATCCGATGGGTTTAAAGAACTGCCTTCTCCGGAATCATTG
AAAGGGAAAATTCTAATATCTACCAAACCGCCGAAAGAATACCTTGAAGC
CGCTGTCGCA Nucleotide sequence of the partial PLC2 from
Physcomitrella patens
                                        (SEQ ID NO:2)
CGGCACCAGGCGGCATGAAGGTCACACACGGAAACACACTTACCAATCCG
GTGTCGTTCCAAAAGTGTGTCACAGCCATCAAGAATAACGCCTTCTTCAC
CTCGGAGTACCCAGTTTGCGTTACTATTGAGGATCATCTTACAAGCGAAT
TACAGGGCCATGCTGCAGAGATTTTAGAGCAAATTCTCGGAGACGCCCTG
TATTATCCACCCACAACTGATGCATTAGTGGAGTTTCCTTCACCGGAGTC
ACTGAAGAGGAAGATCATAATCTCCACCAAACCGCCGAAGGAGTATCTCG
AAGCATGTTCCACGCAGAAATTGGCCATGGAGAACAGGAATCTGGTGGAG
GAGCTCGAGAAGGAAGACAAATTGGAGCAGACCACATTCGCTCCCCTTGA
AGAGAACCACATCCTGGGAGAAAATACACCATCGCTGCGTAAGGAAGTCG
AGGTTTTAAGCCAAAAGGAAATGTCAACACCAAGCTGAGCTTAACTCTAG
AAAGTCCCTCCTGGACCTCGGGGAAGCAACCATCCACAAGGTATAGCAAA
GAGCAACGATGGCAATGACAACCCTAAAACATTTCAAGTATGCCCGGTTC
ATCAACATCCGGCTAGCAAACACGCAACGGGGACATCGTGGCGCTCGCAC
TGCCAGTCGATGGATCAGAACGGATCAGCGGCGATCNATGAAAAGGGGAA
TGCCGA Nucleotide sequence of the partial 14-3-3P-1 from
Physcomitrella patens
                                        (SEQ ID NO:3)
TTTTTTTTTAATTGTAAACCGCACAGCCCGGACACAAAACCATCCCACTG
CACGAGTCAGATATAACCGTACATGATGTTTATAATGCATTGTTCATTTT
AATATTAAAATCTTAGCATTCCTCATCCTAGCCAACGAAGGAAAGAAAAA
AGAGAAAAGAAAAGGACAAAAGAGGAAATCTATGAACAGCCAGTCTCTAC
GCAGAACAAAATAGGCAAGACATGTCATACAACCGCCAGCACGGAACTAC
ACTACGTCTCGCCCCGGCCTACCACCAATCAATTGAGGCTCTTTCCGAAT
CCACCCCATCAGAAAAGACTTGATTGTCGTGATCACTCCGCTTCCTCCGG
TCTCATGTCATCTCCCTTTCCCTGGTCGTCGCCTACATCGTCCTGGACAT
CTGACGTCCATAAAGTCAGATTATCTCTAAGTAGTTGCATGATCAATGTG
CTGTCCTTGTACGACTCCTCACTCAATGTGTCCAATTCGGCAATTGCCTC
GTCGAATGCTTGCTTCGCCAAATGGCATGCCCGCTCAGGGGAGTTCAAAA
TCTCATAATAGAAGACAGAGAAGTTCAAGGCCAGTCCCAGCCGAATCGGA
TGAGTTGGCGCCAAGTCTGTCACTTGCTGTATTAGATGCAGCCTGGTAGG
CCTTCAAAGATTGGTCAGCAGCTTCTTTTCTCTCAGCCCCAGTTTTGAAC
TCCGCCAGGTACCGATAGTAATCTCCCTTCATTTTATAGTAGAACACAGT
GGACTCTCCCGTGCTGGACGAAGGAATCAAATGTCCGTCGATGATAGACA
GGATATCATTGCAGATCTTCGACAGCTCCTCCTCCACCTTGTGTCTGTAG
TCCTTGATGCGTTTAACATTCTGTTCGTTACCTTTGCTCTCCTCCTTCTG
TTCGATGGATGACATGATCCGCCATGACGCCCTCCGGGCTCCGATGACAT
TCTTATAACCCACGGACAGAGATTTCGCTCCTCTACTGTCAGCTCCACA
TCAAGCTTGGCAACCTTCTTCATCGATTCTCCACCATCTCATCGTAACGCTC
CGCCTGCTCGGCGAGCTTGGCCATGTACACATAGCTCTCGCGCTCCTTCT
CCGTACTCATCTTGGCCTAGCACACTCGTCCACGACAGTCCGAAATAGCA
GTATCGCGCACCGTCCCCCGAGCACAAACCAAGCGCAGAACGGCAACACA
```

```
                                        -continued
CTATGCAATGTAAAGGAAACGCAGACACAAGAGGAGACGGAAAAAACAAT
AGAGGCAGGAAGAGAGTGGGAGAGAAGAAGAGACGGGGGAGCGGGGCGATGGA
GGAGCACGGTGAGCTGGTGC Nucleotide sequence of the partial 14-3-3P-2 from
Physcomitrella patens
                                        (SEQ ID NO:4)
GCACGAGCACTGTTACATCGTCGTAGATCTGGTCAGATACCANAACCGGC
GAGAAGCATGCAACACAAGAAAACCTGGAGATGTAATGGTTATGCCGATA
GGGTTTCATTTAAAACAATCTACATAACCCAGTGCTAATTGTTCTGGGAA
GTCGAGCACATATCCGTACCAGCCTCAACTTAGTCGCCTGGACATGAGTT
TCTATTCTAAGTTCTAGTGGTCATCANCATCTTCGACCTTGGAATCCTTT
CCTTCTTCACCAATGNCGTCCTGCATATCTGAAGTCCATAAGGTAAGGTT
ATCCCGGAGCAGCTGCATAATGAGAGTACTGTCTTTGTAGGATTCCTCTC
CTAAGGTATCTAACTCAGAGATAGCTTCATCAAAAGCCTGCTTGGCAAGA
TGGCATGCTCGGTCTGGAGAAACCAAAATTTCGTAGTAAAAGACAGAAAA
ATTCAAAGCCAATCCCAATCTGATCTCGTGCC Nucleotide sequence of the partial CBP-1 from
Physcomitrella patens
                                        (SEQ ID NO:5)
GCACCAGGTTTTAGTAACAGATGGGAAATACTGCAAGAGCGTTTGGTTGT
TGAAAGGGCCTACAGTTGTAAACTAGGCGATCACAAGTGCATTGCTTCAT
TGAGCTTTCGCATGGACTCAATCCAGCTATTGATCTCAATCTTTGTTTTT
TCTAAAACATTTTTTCACACAGATGAGCCGGTAGTAGTGTCAGTACTAGA
CGGCTCAGCAATTAAGGCTTTGCTAGAAGATGAAGATGATTTTGCGATGG
TTGCCGAGGATCTGTTTGAGAAGTTAGACACTGATGAGAGTGGCAAGCTG
AGCAGCAAAGAGCTTCGACCTGCCATTATGCAGCTGGGCGTTGAGCAGGG
TGTCCCTCCTGCCGCAGCTACTACTGAAGCGGAGGAATTGGTTACCAAGT
TGATCAACAAGTACGGCCAGGGAACCGAGGAGCTTGGACAAGCTCAATTT
GCTGCATTATTGCAAGATGTCCTTCAGGATATGCCGAGTCTCTTGCAGA
GAAACCTATCACAATTGTACGAGATGTGAAAATGCTCAACGGCTCTCATT
TGCGAAAGATGCTTGGCTGATGAGAAGGCATTCAAAGGAAATGGCAGATA
ACATGTTTTAATTGACCTCAGATGTCAACAAAAGATCAACGCTTGAGCAA
GTGAAATCAGACCATTATTTGAACAACAAACTGAGCGTGGGGGTCTACCT
CCCGTGGTGATTCGGCACAAANAATATTGACGAGTTTCAGGCGTGNTCCA
CAAACATGGGNAGTGAAGCCGNTTTGGATCGGCANACCCCGCGGTTTGGG
AACNNGGGGTC Nucleotide sequence of the full-length PLC-1 from
Physcomitrella patens
                                        (SEQ ID NO:6)
ATCCCGGGAATCGTCGGGTGACATTCCTGTTCCTACTGCTGTTTGGCCCA
TTCGTCCACTCGGCCCATCTCCACTGACTTCCCCAATTGAGATCAGATGG
TCTTGTAAGGCAGAGAGCGAGCGAGAGAGAGAGAGAGAGAGAGAGAGA
TTGGGAGTTGAGGCGAAGGGGAGGTGTCGGAGGGGATTTATTGTGCCGTA
GCTGGGTTTGCAAAAATGTGTTCTATTCCGTTCGGTCGGAAGAAGTCCAA
GAAGGGGGATTTGGCGCAGGATCTGTTGGGGGATGTGTTCTCGACTTACA
GCGAGAATGGGAAGCTGGACGCCGAGGGGTTGCTGAAGTTCTTGCAGACA
GAGCAAGGGGATAGCAAGTCCTCTCTAGATGACGCCAAGCATTTAGTGGA
GTTGATTCGGAATGAGAGACATAAGTCGAAATTCCCTGGGTTCATCGTCA
GCTCGGACCTGTCGAAGGGTGATTTTAAAAACTATGTACTGAGCCCGGAT
TTGAATGGGGTTCTTGAAAGCACTGTGCATCAAGACATGACGCAGCCGTT
ATCGCACTACTTCATATTCACTGGTCACAACTCGTACTTGACGGGTAACC
AGCTTAGCAGCGACAGTAGCGACGTTCCCATTGCTGCTGCAACGT
GGCGTGCGGGTGGTGAACTGGATTTGTGGCCTGACGATAAAGGCGGCAT
CAAGGTCACTCACGGGAACACACTCACCAGTCCAGTTGCTTTCGAGAAGT
GCATAAAAGCCATCAAGGCCAACGCGTTCGTCTCCTCGAAATATCCTGTA
GTTATCACTCTTGAGGATCATCTTTCAAGTCCTTTACAGGCCCTTGCTGC
AGAGACTTTGACGAACATTTTGGGAGAGGACTTGTACTATCCACCCTCAT
CCGATGGGTTTAAAGAACTGCCTTCTCCGGAATCATTGAAAGGGAAATT
CTAATATCTACCAAACCGCCGAAAGAATACCTTGAAGCCGCTGTCGCACA
GAAGTCGGCGTTGAAAGATGAAAAGATTTTGAATGAGTTCAAGAAGGCAG
ATAAGTTGCAGGAGCAGTCAACTGCTCCTGTTAAAAGCCCCGTTGAGAAA
AAGATTGCAGTTCCACCATCAGAAGACAAAATCCATTTCCGAAGAGAA
GGACTTGAGTGAAAAAGTTGGAAATTTACGTGTTGATTCAGAGGGTGAAT
CAGCTGATCCTGCCCCTGCAAGTTCCCCCGACGGTAAGAAAGCAACATTG
ACAGCGGATAGTGAAAGTGACGATGACGACAATAAGAAGAATCCTGAGTA
TGCTGGCTTATCACTATCCACCAATCGAAGCCTTCGAAAGGAACTACCG
TGGAAGACAGACTGAAAGTTGAAGGGACAGTGGTACGGATTAGTCTTTCA
GAGACTAAGCTGGAGAAGGTCACTGAAGAGTTTCCTGAACTTGTGGTCAA
GTTCACGCAGAGGAACATTCTACGTGTGTATCCTGCTGGTAACCGAGTAA
ACTCGTCCAACTATGATCCTACTGCGGCTTGGATTCACGGAGCTCAAATG
GTGGCTCAAAATATGCAAGGTTATGGCAAAGAGCTCTGGCAAGCCCACGG
CAAGTTCAGGGGAAATGGTGGCTGTGGATACATCCTTAAGCCAAAGTATC
TATTGGAAGATTTGCCCAATGGTAAACCTTTTAACCCTTCAGGACAAAGC
GTTCCCCAAATACCATTTCGACCTTTTCTCGCCTCCAGATTTCTTCACTA
GGCTGCTTGTGACTGGAGTGCCTGCCGATGTGGCAAAGTGGAAAACTTCC
GTTATAGATGACGTTTGGGAACCCCACTGGAACGAGGATCACGAGTTTTA
CCTTAAATGCCCTGAACTTGCACTGCTCCGAATTGAAGTTAGAGATCACG
```

-continued

ACGAGGAAAGTCAAGATGAGTTCGAAGGGCAGGCGTGCCTTCCAATGCAT
GAAATTAAAGACGGCTATCGATGCGTGCAGATGTATGACAAAAAGGGCAG
TGTGTTGAAGGGCGTGAAAATGTTGTTCCATTTTCAAAAACGTTCGTTTT
CTCCGGTCCAGTAATTCATCGTTTTCAAAAACATTTCTGTCTCAATCCTG
CAACGAGTAATTTTAGAGAAGGAAGGCTAACGCACTCGAGATGTCTGAAA
GGTGAAGAGTTGGAGGGAAGAAGGGTAGCTCGCTGTATCACCGAGCTCTA
GTGAACTTCAGGTGTCATTCTTTGAGGGCAGCTCATCTTTCTCATGCATG
TGGAACGCTGAGGTGTTGGTTAACGC

Nucleotide sequence of the full-length PLC-2 from
*Physcomitrella patens*

(SEQ ID NO:7)
ATCCCGGGCTTCGGGAGTTTAAGAGGATGTCACGGCGTGGGAAGACGAGG
CGGTGATGCAGGTTTGGGTGGAGCTTAAGGTTGACGGAGTGTAAGGGATC
GGCTCGTCACTGGGTTTGCAAAATGTGTTCCATAGCATGTTGTCGAAGTG
GAACCCCGAAAGGGGATCCGGAGCAAGACCTGGTGGGGAGGTGTTCACA
ATATACAGCGAGAATGAGAGGATGAGTGCGGAGGGGTTGCTGAAATTCTT
GCATACAGAGCAAGGGGATGTCGACTTCACCCTTGATGACGCCAAGCAGA
TCATGGAGCGCATTCGCAAGGACTGGAAGAAATCCTTCGGACTCGCCTCT
ATCAACTCAGACTTGTCGAAGGAGGCTTTTCGGAAGTACTTGATGAATCC
CGACTTGAATGGCGTCTTACACAACGTTGTTCACCAAGACATGACGCAGC
CGATGTCGCACTATTTCATATTCACGGGCCATAACTCGTACCTGACCGGC
AACCAGCTGAGCAGCGACAGCAGCGACACACCCATCGCTGCGGCACTGCG
GCGCGGCGTGCGGGTTGTGGAATTGGACTTGTGGCCTGATGACAAAGGCG
GCATGAAGGTCACACACGGAAACACACTTACCAATCCGGTGTCGTTCCAA
AAGTGTGTCACAGCCATCAAGAATAACGCCTTCTTCACCTCGGAGTACCC
AGTTTGCGTTACTATTGAGGATCATCTTACAAGCGAATTACAGGGCCATG
CTGCAGAGATTTTAGAGCAAATTCTCGGAGACGCCCTGTATTATCCACCC
ACAACTGATGCATTAGTGGAGTTTCCTTCACCGGAGTCACTGAAGAGGAA
GATCATAATCTCCACCAAACCGCCGAAGGAGTATCTCGAAGCATGTTCCA
CGCAGAAATTGGCCATGGAGAACAGGAATCTGGTGGAGGAGCTTGAGAAG
GAAGACAAATTGGAGCAGACCACATTCGCTCCCCTTGAAGAGAACCACAT
CCTGGGAGAAAATACACCCATCGCTGCGTAAGGAAGTCGAGGTTTAAGCC
AAAAGGAAATGTCAACACCAGCTGAGCTTAACTCTAGAGGTCCCTCAGC
CTCGGGGAAGCAACATCCACAAGGTATAGCAAGAGCAACGATGGCAATGA
CAACCCTAAACATTTCAAGTATGCCCGGCTCATCACAATCCGGCTAGCAA
AGCACGCAAAGGGGACATCGATGGAGCATCGACTGCAAGTCGATGAATCA
GTGAAACGGATCAGTCTGTCGGAATCGAAGCTGGAAAGATGGTGGAAA
GTGGCCCGAAGCTCTGGTCAAATTCACGCAGAAGAACATTTTACGTGTGT
ATCCTGCTGCTAATCGTGTAAACTCCTCCAACTTCTGCCCTACTCTGGCT
TGGAACTACGGAGCTCAAATGGTGGCTCAAACATGCAGGGCTATGGTAA
AGAGCTTTGGCAGGCATTTGGCAAGTTCAAGGGAAATGGGGGATGTGGGT
ATGTTTTGAAGCCACAGTATCTGTTGAAAACTTGCCTTCTGGTGTGCCT
TTCAACCCCACATCACCCAGAAACACAACCCTAATTCTCAAGATTAAAGT
TATGACTACCTTGGGATGGGACAAGGCCTTTTCCAAACGCCATTTTGACC
TATTCTCACCTCCAGATTTCTTCACTAGGGTGATTGTGGTGGGAGTGCCT
GCTGACGAGGCCAAGTGGAAGACATCGTGGTGGACAATTCATGGGCACC
CCATTGGAATGAGGACCATGAGTTTGCCCTAAAATGCCCTGAGCTCGCAC
TACTTCGCATCGAGGTCCGAGACCATGATGATGATAGCAAAGATGAGTTT
GAAGGGCAGACATGCCTTCCCATCCATGAAGTCCGGGATGGGTATCGGTG
CATGCAAATGTACGACAAGAAGGGCAATGTACTGAAAGGCGTGCTGATGT
TGTTTCATTTTCAAAAGTGCAAATGCACCTTTCAAGACACAGCTCCTATA
TCCTCTTAAACTCAACCCGCCCACACATGGCCCCATTATCAATTACTAAT
GCTGCTTTTTATGTTGCCATTGTCATATAATTGTTGGTTTGTGGGGGGA
AGACTGACCAGTTTAGTGTGTGCACCCAAGGTTAACGCC

Nucleotide sequence of full-length 14-3-3P-1 from
*Physcomitrella patens*

(SEQ ID NO:8)
ATCCCGGGCGGACTGTCGTGGACGATGTGCTAGGCCAAGATGAGTACGGA
GAAGGAGCGCGAGAGCTATGTGTACATGGCCAAGCTCGCCGAGCAGGCGG
AGCGTTACGATGAGATGGTGGAATCGATGAAGAAGGTTGCCAAGCTTGAT
GTGGAGCTGACAGTAGAGGAGCGAAATCTCTTGTCCGTGGGTTATAAGAA
TGTCATCGGAGCCCGGAGGGCGTCATGCGGATCATGTGATCCATCGAAC
AGAAGGAGGAGAGCAAAGGTAACGAACAGAATGTTAAACGCATCAAGGAC
TACAGACACAAGGTGGAGGAGGAGCTGTCGAAGATCTGCAATGATATCCT
GTCTATCATCGACGGACACCTGATTCCGTCGTCCAGCACGGGAGAGTCCA
CTGTGTTCTACTATAAAATGAAGGGAGATTACTATCGGTACCTGGCCGAG
TTCAAGACCGGGAATGAGAGGAAAGAGGCCGCTGACCAATCTTTGAAGGC
ATACCAGGCTGCATCCAGCACTGCAGTGACGGACCTGGCACCGACGCATC
CTATCCGACTGGGATTAGCTTTGAACTTCTCGGTCTTTTATTATGAAATT
TTGAACTCTCCTGGAGAGCATGCCATTTGGCGAAACAAGCATTTGACGA
GGCGATTGCTGAGTTGGATACGTTAAGTGAGGAGTCGTACAAGGACAGCA
CATTGATCATGCAGCTACTTAGAGATAATCTGACCCTGTGGACATCTGAC
CTTCAGGACGAGGGAGGTGACGACCAGGGAAAGGGAGATGATATGAGGCC
CGAGGAGGCTGAGTGATGACGATTAGGTCTTTTATGTGGAGACGAATTTG
CAAATCACTTCACTCAATTGGTGGTGGGCCGGGGCAAGAAGATGTGCAGT
TGCGTGCCGAGCTCGC

Nucleotide sequence of full-length 14-3-3P-2 from
*Physcomitrella patens*

(SEQ ID NO:9)
GCGTTAACTTCACAATGACGGAGCTACGAGAGGAAAATGTGTACATGGCT
AAGCTCGCCGAGCAGGCGGGAGCGGTACGATGAGATGGTGGAAGCCATGGA
GAATGTGGTAAAGGCGGTGGAGAACGAGGAGCTGACCGTGGAGGAGCCGGA
ACCTGTTGTCGGTGGCGTTTAAGAACGTGATTGGTGCGAGGAGGGCGTCG
TGGCGGATCATCTCTTCCATCGAGCAGAAGGAAGAGGCCAAGGGGTCTGA
GGAGCACGTCGCTGCTATTAAGGAGTACCGATCCAAAGTAGAGGCTGAGT
TGAGCACCATCTGTGACACTATATTGAAGCTTTTGGACTCGCACCTGATC
CCGTCCTCCACCTCGGGGGAGTCGAAGGTTTTTTACTTGAAAATGAAGGG
AGACTATCACAGGTACCTGGCTGAGTTCAAAGCCGGCGCTGAGAGAAAAG
AGGCAGCTGAGGCTACATTGCACGCGTACAAGCATGCACAAGACATTTCA
ACGACAGAGTTGGCGTCCACACATCCTATCAGATTGGGATTGGCTTTGAA
TTTTTCTGTCTTTTACTACGAAATTTTGGTTTCTCCAGACCGAGCATGCC
ATCTTGCCAAGCAGGCTTTTGATGAAGCTATCTCTGAGTTAGATACCTTA
GGAGAGGAATCCTACAAAGACAGTACTCTCATTATGCAGCTGCTCCGGGA
TAACCTTACCTTATGGACTTCAGATATGCAGGACGACATTGGTGAAGAA
GGAAAGGATTCCAAGGTCGAAGATGCTGATGACCACTAGAACTTAGAAT
AGAAACTCATGTCCAGGCGACTAAGTTGAGGCTGGAGCTCGC

Nucleotide sequence of the full-length CBP-1 from
*Physcomitrella patens*

(SEQ ID NO:10)
ATCCCGGGTCAGCTCGTGGAAGTGTTGCAGCAGCGCGGACGGGCAGGATC
GGACATTTTGAGATTTTTGACAGGGCTATCAGAGGTGTTCAGAAGGGACG
ACAAAGACCAGCATGTCAACAGAGGGAGGACTGCATGTTCTTGATGGATC
TCAGATCAGAAATGCATTACCCGATCTTCAATCGAGGACAGTTTTTCTA
AGAATGATGAAGGGTCGAAAGGGTATCTGACACCATCTGAGATGCGGCAG
GCTGCGGAAGCAGAAGCAGCCGCTGCTTCTCTTAGGTGTCCAACTTTCCTC
AAAGATTTTTGAAAATGCTGCATCAAAACTTCCAACTGAAGATTCTGCAG
AGATCACGGAGGACGTGTTTTCCAGTACTCTGCAGAGTTATCTAACAGCA
ATTGCTGATGCTTTAGAAGATGAGCCGGTAGTAGTGTCAGTACTAGACGG
CTCAGCAATTAAGGCTTTGCTAGAAGATGAAGATGATTTTGCGATGGTTC
CCGAGGATCTGTTTGAGAAGTTAGACACTGATGAGAGTGGCAAGCTGAGC
AGCAAAGAGCTTGACCTGCCATTATGCAGCTGGGCGTTGAGCAGGGTGT
CCCTCCTGCCGCAGCTACTACTGAAGCGGAGGAATTGGTTACCAAGTTGA
TCAACAAGTACGGCCAGGGAACCGAGGACGTTGGACAAGCTCAATTTGCT
GCATTATTGCAAGATGTCCTTCAGGATATGGCCGAGTCTCTTGCAGAGAA
ACCTATCACAATTGTACGAGATGTGAAAATGCTCAACGGCTCTCATTTGC
GAAAGATGCTGGCTGATGAGAAGGCATTCAAGGAAATGGCAGATAACATG
TTTAATGACCTAGATGTCAACAAAGATCAACGCTTGAGCAAGGCTGAAAT
CAGACCATTATTTGAACAACAAACTGCAGCGTGGGGTCTACCTCCCGTTG
GTGATTCGGACACAGAAGAACTATTTGACGAGGTTTTCAAGGCCGTTGAC
TCAGACAAAAGTGGGGAAGTTGAAAAGCCTGAGTTTGCAGTTCTTGTCAA
GACTCTCCTTGCGGATTTTGCGGAAACGTTGCGGCTCAACCCAATACTAG
TGGAGATAGAAACTGCCTCTCGTTGAAGCATCGAGTCATAGTTCTGGGGG
AGCGATGTTTTCTAAAGTCGTAGTCCATTTTTGGATAAGATGACTTTGCA
CCCAGAGTTCTTGTGAAACGTGACACCAGGTATGATGAAGGCTTGATGAT
ATTTTAGAGTGACAATTTTATGTGGCTAGAGGCTCATGAGGTCGTGAGAT
CGAAGTGGAAATGATTTTGTGAAAGCTACTTCGACCTGGGTAGCTTTTCTA
AGCTAGGATAGTTATATGAAAAAGATAATTAAACTTCAAGCGGATCAATA
TAGCTCACAGAATCCATTCTTCGTTTCTGTTTCCTGAGAACCCACCAATG
TCCAAGTTACAAAACTCCGTGGGAGAAACAGACGTGCAGTGCATGCATAA
GGTTGGTGTGATTGTTGCGTAGCTGATGTTTCTGGATGACTTGAATAGAA
TCAAGTGCATAGATAGTCAATTGTCTCACACAAGATCTTCGAACAATCCA
CCAACCGGCGTTGCCAGTCGTGCGGAGGGCACGTTGGTGGGACGGACTA
GCGGTGCGACGCGTGTAGAGAATGCATTGGCGGCTGCAGATTAGACAGTT
GTTCGCATCCGTTGTAGGATAGATCGTTAGGATACTCGACTCTTACCTGT
GTTCGAATTCCGGCATCGGAAGCCCCCGAGTGAAAATTGGACGAGCTCGC

Deduced amino acid sequence of PLC-1 from
*Physcomitrella patens*

(SEQ ID NO:11)
MCSIPFGRKKSKKGDLAQDLLGDVFSTYSENGKLDAEGLLKFLQTEQGDS
KSSLDDAKHLVELIRNERHKSKFPGFIVSSDLSKGDFKNYVLSPDLNGVL
ESTVHQDMTQPLSHYFTFTGTINSYLTGNQLSSDSSDVPIAAALQRGVRV
VELDLWPDDKGGIKVTHGNTLTSPVAFEKCTKAIKANAFVSSKYPVVITL
EDHLSSPLQALAAETLTNILGEDLYYPPSSDGFKELPSPESLKGKILIST
KPPKEYLEAAVAQKSALKDEKTLNEFKKADKLQEQSTAPVKSPVEKKIAV
PPSEKTKSISEEKDLSEKVGNLRVDSEGESADPAPASSPDGKKATLTADS
ESDDDDNKKNPEYARLITIHQSKPSKGTTVEDRLKVEGTVVRISLSETKL
EKVTEEFPELVVKFTQRNTLRMCSTPFGRKKSKKGDLAQDLLGDVFSTYS

-continued

ENGKLDAEGLLKFLQTEQGDSKSSLDDAKIILVELTRNIERHKSKFPGFI
VSSDLSKGDFKNYVLSPDLNGVLESTVHQDMTQPLSHYFTETGHNSYLTG
NQLSSDSSDVPIAAALQRGVRVVELDLWPDDKGGTKVTHGNTLTSPVAFE
KCTKATKANAFVSSKYPVVITLEDHLSSPLQALAAETLTNILGEDLYYPP
SSDGFKELPSPESLKGKILISTKPPKEYLEAAVAQKSALKDEKTLNEFKK
ADKLQEQSTAPVKSPVEKKIAVPPSEKTKSISEEKDLSEKVGNLRVDSEG
ESADPAPASSPDGKKATLTADSESDDDDNKKNPEYARLITTHQSKPSKGT
TVEDRLKVEGTVVRISLSETKLEKVTEEFPELVVKFTQRNTLRVYPAGNR
VNSSNYDPTAAWIHGAQMVAQNMQGYGKELWQAHGKFRGNGGCGYILKPK
YLLEDLPNGKPFNPSAPGDTKMILKVKVMTTMGWDKAFPKYHFDLFSPPD
FFTRLLVTGVPADVAKWKTSVIDDVWEPHWNEDHEFYLKCPELALLRIEV
RDHDEESQDEFEGQACLPMHEIKDGYRCVQMYDKKGSVLKGVKMLFHFQK
RSFSPVQ

Deduced amino acid sequence of PLC-2 from Physcomitrella patens (SEQ ID NO:12)

MCSIACCRSGTPKGDPEQDLVGEVFTIYSENIERMSAEGLLKFLHTEQGD
VDFTLDDAKQTMERIRRDWKKSFGLASINSDLSKEAFRKYLMNPDLNGVL
TINVVHQDMTQPMSHYFIFTGHNSYLTGNQLSSDSSDTPIAAALRRGVRV
VELDLWPDDKGGMKVTHGNTLTNPVSFQKCVTATKNNAFFTSEYPVCVTI
EDHLTSELQGHAAETLEQILGDALYYPPTTDALVEFPSPESLKRKIIIST
KPPKEYLEACSTQKLAMENIRNLVEELEKEDKLEQTTFAPLEENHILGEN
TPSLRREVEVLSQKEMSTPAELNSRSPSDLGEATSTRYSKSNDGNDNPKH
FKYARLITIRLAKHAKGTSMEITRLQVDESVKRISLSESKLEKVVEKWPE
ALVKETQKNILRVYPAANRVNSSNFCPTLAWNYGAQMVAQNMQGYGKELW
QAFGKFKGNGGCGYVLKPQYLLENLPSGVPFNPTSPRNTTLILKIKVMTT
LGWDKAFSKRHFDLFSPPDFFTRVIVVGVPADEAKWKTSVVDNSWAPHWN
IEDHEFALKCPELALLRTEVRDHDDDSKDEFEGQTCLPIFTEVRDGYRCM
QMYDKKGNVLKGVLMLFHFQKCKCTFQDTAPISS

Deduced amino acid sequence of 14-3-3P-1 from Physcomitrella patens (SEQ ID NO:13)

MSTEKERESYVYMAIKLAEQAERYDEMVESMKKVAKLDVELTVEERNLLS
VGYKNVIGARRASWRIMSSTEQKEESKGNEQNVKRTKDYRHIKVEEELSK
ICNDTLSIIDGHLIPSSSTGESTVFYYKMKGDYYRYLAEFKTGNERKEAA
DQSLKAYQAASSTAVTDLAPTHPIRLGLALNFSVFYYEILNSPERACHLA
KQAFDEAIAELDTLSEESYKDSTLIMQLLRDNLTLWTSDLQDEGGDDQGK
GDDMRIPEEAE

Deduced amino acid sequence of 14-3-3P-2 from Physcomitrella patens (SEQ ID NO:14)

MTELREENVYMAKLAEQAERYDEMVEAMENVVKAVENEELTVEERNLLSV
AFKNVIGARRASWRITSSTEQKEEAKGSEEHVAAIKEYRSKVEAELSTIC
DTTLKLLDSHLIPSSTSGESKVFYLKMKGDYHRYLAEFKAGAERKEAAEA
TLHAYKHAQDISTTELASTHPIRLGLALNFSVFYYEILVSPDRACHLAKQ
AFDEAISELDTLGEESYKDSTLIMQLLRDNLTLWTSDMQDDIGEEGKDSK
VEDADDH

Deduced amino acid sequence of CBP-1 from Physcomitrella patens (SEQ ID NO:15)

MSTEGGLHVLDGSQTRNALPDLQSRNSFSKNDEGSKGYLTPSEMRQAAEA
EAAALLLGVQLSSKTFENAASKLPTEDSAEITEDVFSSTLQSYLTAIADA
LEDEPVVVSVLDGSAIKALLEDEDDFAMVAEDLFEKLDTDESGKLSSKEL
RPATMQLGVEQGVPPAAATTEAEELVTKLINKYGQGTEELGQAQFAALLQ
DVLQDMAESLAEKPITIVRDVKMLNGSHLRKMLADEKAFKEMADNMFNDL
DVNKDQRLSKAETRPLFEQQTAAWGLPPVGDSDTEELFDEVFKAVDSDKS
GEVEKIPEFAVLVKTLLADFAETLRLNPTLVETETASR

We claim:

1. A transgenic plant cell transformed with an expression cassette comprising an isolated polynucleotide encoding a full-length 14-3-3 polypeptide having a sequence comprising amino acids 1 to 258 of SEQ ID NO:13.

2. The plant cell of claim 1, wherein the polynucleotide has a sequence comprising nucleotides 1 to 916 of SEQ ID NO:8.

3. A transgenic plant transformed with an expression cassette comprising an isolated polynucleotide encoding a full-length 14-3-3 polypeptide having a sequence comprising amino acids 1 to 258 of SEQ ID NO:13.

4. The plant of claim 3, wherein the polynucleotide has a sequence comprising nucleotides 1 to 916 of SEQ ID NO:8.

5. The plant of claim 3, further described as a monocot.

6. The plant of claim 3, further described as a dicot.

7. The plant of claim 3, wherein the plant is selected from the group consisting of maize, wheat, rye, oat, triticale, rice, barley, soybean, peanut, cotton, rapeseed, canola, manihot, pepper, sunflower, tagetes, potato, tobacco, eggplant, tomato, Vicia species, pea, alfalfa, coffee, cacao, tea, Salix species, oil palm, coconut, perennial grasses, and a forage crop plant.

8. A seed which is true breeding for a transgene comprising a polynucleotide encoding a full-length 14-3-3 polypeptide having a sequence comprising amino acids 1 to 258 of SEQ ID NO:13.

9. The seed of claim 8, wherein the polynucleotide has a sequence comprising nucleotides 1 to 916 of SEQ ID NO:8.

10. An isolated polynucleotide having a sequence comprising nucleotides 1 to 916 of SEQ ID NO:8.

11. An isolated polynucleotide encoding a polypeptide having a sequence comprising amino acids 1 to 258 of SEQ ID NO:13.

12. A method of producing a drought-tolerant transgenic plant, the method comprising the steps of:
- a) transforming a plant cell with an expression cassette comprising a polynucleotide encoding a full-length 14-3-3 polypeptide having a sequence comprising amino acids 1 to 258 of SEQ ID NO:13;
- b) growing the transformed plant cell to generate transgenic plants; and
- c) screening the transgenic plants generated in step b) to identify a transgenic plant that expresses the polypeptide and exhibits increased tolerance to drought stress as compared to a wild type variety of the plant.

13. The method of claim 12, wherein the polynucleotide has a sequence comprising nucleotides 1 to 916 of SEQ ID NO:8.

14. The plant of claim 7, which is maize.

15. The plant of claim 7, which is rice.

16. The plant of claim 7, which is soybean.

17. The plant of claim 7, which is cotton.

18. The plant of claim 7, which is rapeseed or canola.